United States Patent
Wilhelm Schmidt et al.

(10) Patent No.: US 11,480,583 B2
(45) Date of Patent: Oct. 25, 2022

(54) METHOD FOR THE DIAGNOSIS AND TREATMENT OF ESSENTIAL PRIMARY HYPERTENSION

(71) Applicants: Universiteit Maastricht, Maastricht (NL); Academisch Ziekenhuis Maastricht, Maastricht (NL)

(72) Inventors: Harald Horst Heinz Wilhelm Schmidt, Aachen (DE); Mahmoud Hassan Mahmoud Elbatrik, Maastricht (NL); Hermann Alois Martin Mucke, Vienna (AT)

(73) Assignees: Universitet Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 17/552,578

(22) Filed: Dec. 16, 2021

(65) Prior Publication Data

US 2022/0128574 A1    Apr. 28, 2022

Related U.S. Application Data

(63) Continuation of application No. PCT/EP2021/063686, filed on May 21, 2021.

(30) Foreign Application Priority Data

May 25, 2020  (EP) .................... 20176348

(51) Int. Cl.
  *G01N 33/53*   (2006.01)
  *G01N 33/68*   (2006.01)
  *A61K 31/498*  (2006.01)

(52) U.S. Cl.
  CPC ........ *G01N 33/6893* (2013.01); *A61K 31/498* (2013.01); *G01N 2800/321* (2013.01)

(58) Field of Classification Search
  CPC ......... G01N 33/6893; G01N 2800/321; G01N 2470/00; G01N 2470/04; G01N 2470/06; G01N 2470/10; G01N 2470/12; A61K 31/498; A61P 9/12
  See application file for complete search history.

(56) References Cited

FOREIGN PATENT DOCUMENTS

WO    2004/017955 A1    3/2004

OTHER PUBLICATIONS

McRae et al (Journal of Chiropractic medicine 2009;8.14-24).*
Touyz et al (Antioxidants and Redox Signaling,2019; vol. 30 No. 7 pp. 1027-1040).*
Novus Elisa NOX5 (2017;retrieved from https://www.novusbio.com/products/nox5-elisa-kit_nbp2-76749).*
Amabile et al (European Heart journal 2014;35,2972-2979).*
Gielis et al. (Free radical Biology and Medicine 50;2011;765-776).*
Elbatreek et al., "NOX5-induced uncoupling of endothelial NO synthase is a causal mechanism and theragnostic target of an age-related hypertension endotype", PLOS Biology, https://doi.org/10.1371/journal.pbio.3000885 Nov. 10, 2020.
Touyz et al., "NOX5: Molecular biology and pathophysiology", Experimental Physiology 2019;104:605-616, wileyonlinelibrary.com/journal/eph.
Bai et al., "Metabolomic Study for Essential Hypertension Patients Based on Dried Blood Spot Mass Spectrometry Approach", pp. 777-785, IUBMB Life.
Khalaf et al., "The Effects of Oral I-Arginine and L-Citrulline Supplementation on Blood Pressure", Nutrients 2019,11,1679; doi:10.3390/nu11071679, www.mdpi.com/journal/nutrients.
Casas et al., "Calcium-depierdent blood-brain barrier breakdown by NOX5 limits postreperfusion benefit in stroke", J Clin Invest. 2019;129(4):1772-1778 https:/./doi.org/10,1172/JCI124283.
Shere et al., "Circulating blood biomarkers in essential hypertension: a literature review", Journal of Laboratory and Precision Medicine, 2017, jlpm.amegroups.com, J Lab Precis Med 2017;2:99.
Carey et al.,"Resistant Hypertension: Detection, Evaluation, and Management: A Scientific Statement From the American Heart Association", Hypertension. Nov. 2018; 72(5): e53-e90. doi:10.1161/HYP.0000000000000084.
Simao Do Carmo et al., "NOX5 as a therapeutic target in cerebral ischemic injury", The Journal of Clinical Investigation, jci.org, vol. 129, No. 4, Apr. 2019,pp. 1530-1532.

(Continued)

*Primary Examiner* — Carmencita M Belei
(74) *Attorney, Agent, or Firm* — N.V. Nederlandsch Octrooibureau

(57) ABSTRACT

The invention is in the field of molecular diagnosis of medical diseases and their treatment. More in particular, it provides methods and means for detecting hypertension, more in particular essential primary hypertension, even more in particular NOX5-dependent hypertension. The invention also provides methods for the treatment of hypertension, in particular essential primary hypertension, more in particular NOX5-dependent hypertension. The invention also provides theragnostics, wherein therapy is combined with diagnosis, more in particular wherein the level of NOX5 is determined in a sample from a subject and wherein the subject is treated with NOX5 inhibitors or compounds that decrease the levels of NOX5 if the NOX5 levels are above a certain threshold value. Further, the invention also provides theragnostics, wherein diagnosis is combined with therapy, more in particular wherein the (plasma) level of NOX5 is determined in a sample from a subject and wherein the subject is treated with NOX5 inhibitors or compounds that reverse the result of NOX5 activity in the subject, when the determined NOX5 level is exceeding a predetermined threshold level. Finally, the invention relates to an animal model suitable for developing diagnostic methods and therapeutic treatments for NOX5-dependent hypertension.

7 Claims, 26 Drawing Sheets

(56) References Cited

OTHER PUBLICATIONS

Figure 1A:
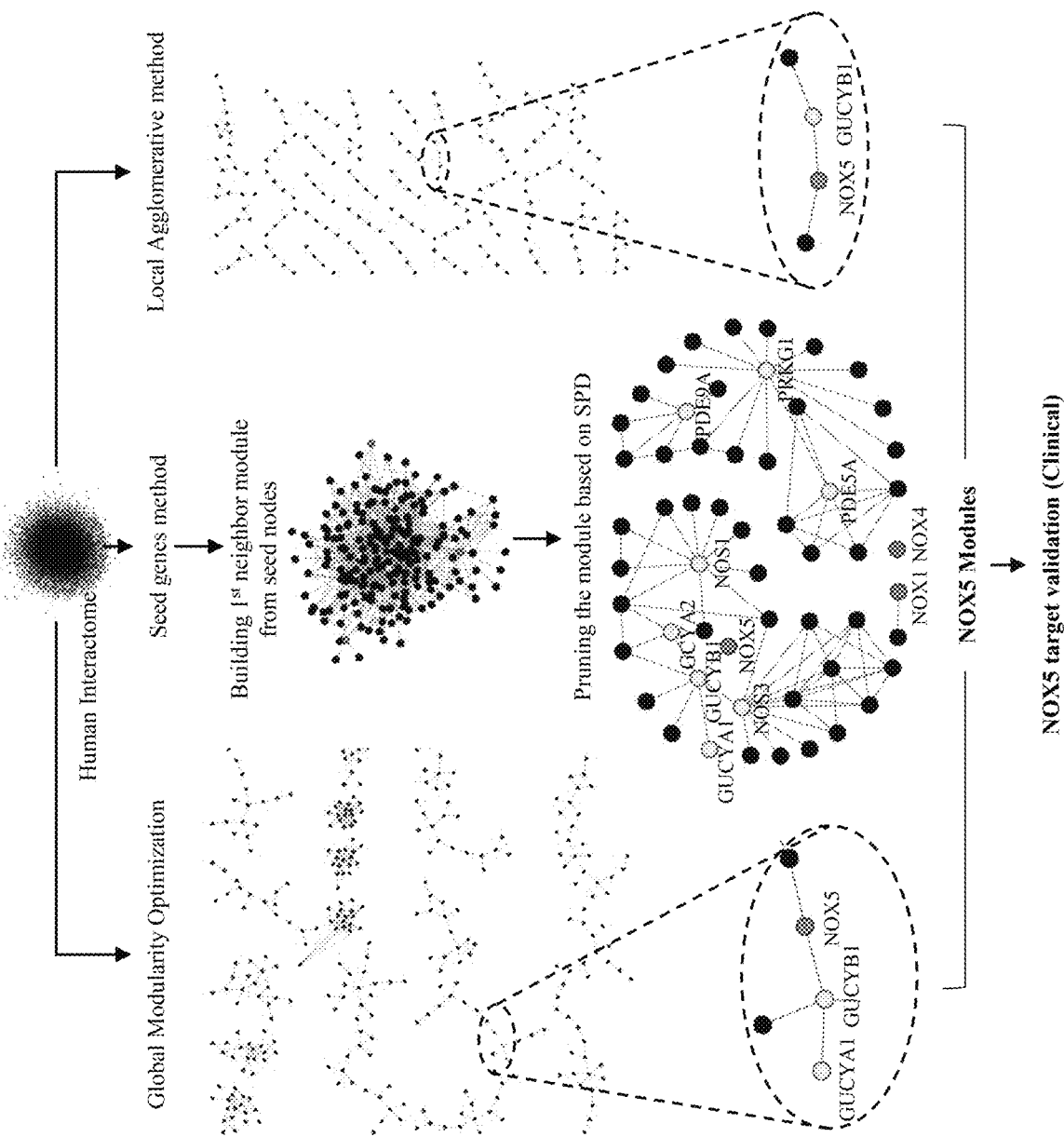

Furmanik et al., "Reactive Oxygen-Forming Nox5 Links Vascular Smooth Muscle Cell Phenotypic Switching and Extracellular Vesicle-Mediated Vascular Calcification", Circulation Research. 2020;127:911-927. DOI: 10.1161/CIRCRESAHA.119.316159, pp. 911-927.
Dao et al., "Isoform-selective NADPH oxidase inhibitor panel for pharmacological target validation", Free Radical Biology and Medicine 148 (2020) pp. 60-69, https://doi.org/10.1016/j.freeradbiomed.2019.12.038.
Dao et al., "Isoform-selective NADPH oxidase inhibitor panel for pharmacological target validation".
Casas et al., "Calcium-dependent blood-brain barrier breakdown by NOX5 limits post-reperfusion benefit in stroke", supplement.

\* cited by examiner

NOX5 Validation (preclinical)

METHOD FOR THE DIAGNOSIS AND TREATMENT OF ESSENTIAL PRIMARY HYPERTENSION

FIELD OF THE INVENTION

The invention is in the field of molecular diagnosis of medical diseases and their treatment. More in particular, it provides methods and means for detecting hypertension, more in particular essential primary hypertension, even more in particular NOX5-dependent hypertension. The invention also provides methods for the treatment of hypertension, in particular essential primary hypertension, more in particular NOX5-dependent hypertension. The invention also provides theragnostics, wherein therapy is combined with diagnosis, more in particular wherein the level of NOX5 is determined in a sample from a subject and wherein the subject is treated with NOX5 inhibitors or compounds that decrease the levels of NOX5 if the NOX5 levels are above a certain threshold value. Further, the invention also provides theragnostics, wherein diagnosis is combined with therapy, more in particular wherein the (plasma) level of NOX5 is determined in a sample from a subject and wherein the subject is treated with NOX5 inhibitors or compounds that reverse the result of NOX5 activity in the subject, when the determined NOX5 level is exceeding a predetermined threshold level. Finally, the invention relates to an animal model suitable for developing diagnostic methods and therapeutic treatments for NOX5-dependent hypertension.

BACKGROUND OF THE INVENTION

Hypertension is of major medical relevance as a risk factor for myocardial infarction, stroke and other chronic conditions and death [1]. With the exception of 5% of patients with secondary hypertension (due to renal artery stenosis, adrenal adenomas, pheochromocytomas and numerous single gene mutations involving renal transporters [2]), in the remaining 95% of all cases the cause of hypertension is not known. In these cases of so-called 'essential primary hypertension', treatments have to focus on symptomatic vasodilatory drug therapy and lifestyle management. Even this symptomatic antihypertensive therapy is sometimes ineffective, i.e. in treatment-resistant hypertension, and requires high number to treat with many patients still experiencing adverse outcomes such as stroke and myocardial infarction [3]. Resistant hypertension (RH) is defined by the American Heart Association [104] as: above-goal elevated blood pressure (BP) in a patient despite the concurrent use of three anti-hypertensive drug classes, commonly including a long-acting calcium channel blocker, a blocker of the renin-angiotensin system (angiotensin-converting enzyme inhibitor or angiotensin receptor blocker), and a diuretic. The antihypertensive drugs should be administered at maximum or maximally tolerated daily doses. RH also includes patients whose BP achieves target values on more than four anti-hypertensive medications. The diagnosis of RH requires assurance of anti-hypertensive medication adherence and exclusion of the "white-coat effect" (office BP above goal but out-of-office BP at or below target).

One molecular mechanism of hypertension that has been suggested for decades is oxidative stress, i.e. an unphysiological production of reactive oxygen species (ROS), which in blood vessels interferes with vasodilation by the endothelium-derived relaxing factor, nitric oxide (NO) [4]. No hypertension-relevant cellular source of ROS, however, has been identified to either prove this hypothesis or exploit it for a mechanism-based or even curative clinical therapy.

Recent genome-wide association studies (GWAS) [5] in search for hypertension risk genes point towards NADPH oxidases (NOX), the only known enzyme family dedicated to ROS formation, in particular the genes Nox4 and Nox5. This matches preclinical studies, excluding other vascular NOX isoforms i.e. NOX1 and NOX2 with respect to causing hypertension, unless animals are infused with pro-hypertensive agents [6-8]. With respect to NOX4, this isoform is widely expressed, but appears irrelevant for blood pressure or hypertension [9] but is rather vaso-protective [10]. With respect to NOX5, this enzyme is physiologically expressed in vascular endothelial cells of human blood vessels and may be associated with diabetic nephropathy [11-13]; mice expressing human NOX5 in vascular smooth muscle cells are, however, normotensive [14]. Thus, the role of NOX5 in hypertension remains as yet unclear.

In moving away from single targets, network medicine [15] predicts that for most in particular complex diseases not a single protein but protein modules, i.e. sub-graphs of the interactome, are in fact relevant [16-18]. Therefore, we set out to reinvestigate the association of NOX with hypertension and NO-dependent vasodilation using three complementing unbiased in-silico approaches and to validate any prediction both in mice and, if possible, also human patient samples.

SUMMARY OF THE INVENTION

The invention relates to a novel method for diagnosing essential arterial hypertension in a subject, in particular NOX5-dependent hypertension in a subject, wherein the level of NADPH oxidase 5 (NOX5) is determined in a fluid or tissue sample from the subject, and wherein it is concluded that the subject has essential arterial hypertension, in particular NOX5-dependent hypertension, if the level of NOX5 is above a predetermined threshold level.

The invention also relates to a method for detection of a hypertension endotype in a human patient suffering from essential arterial hypertension, wherein said endotype is defined by an increased level of circulating NADPH oxidase 5 protein (NOX5) compared to the level of circulating NOX5 in a human subject not suffering from hypertension, the method comprising the steps of:
  (a) obtaining a fluid sample from the human patient who suffers from essential arterial hypertension, selected from the group comprising plasma, blood and serum, wherein the fluid sample comprises circulating endothelial microparticles;
  (b) isolating the endothelial microparticles from the fluid sample provided in step (a); and
  (c) measuring NOX5 in the endothelial microparticles of step (b) using a protein detection assay and determining the concentration of NOX5 in the fluid sample in pg NOX5 per ml fluid sample, wherein it is concluded that the human patient suffers from the hypertension endotype if the concentration of NOX5 as determined in step (c) is at least 160 pg NOX5 per ml of the fluid sample.

In one embodiment, the invention therefore relates to a novel method for diagnosing a hypertension endotype in a subject wherein the level of NOX5 is determined in a fluid or tissue sample from the subject, preferably plasma sample, and wherein it is concluded that the subject has the hypertension endotype if the level of NOX5 is above a predetermined threshold level. The threshold level can be defined as the amount of NOX5 protein (enzyme) per volume, such as pg NOX5 per ml plasma of the hypertension endotype patient. The threshold level can also be defined as the NOX5 enzyme activity per volume, such as I.U. enzyme activity per ml plasma of the patient suffering from the endotype. This method identifies the subjects with a disease entity (endotype) that was previously a disease entity generally called treatment-resistant hypertension. Those cases of resistant hypertension patients suffering from the endotype as now defined by the inventors may now effectively be treated with NOX5 inhibitors or with compounds selected from the group consisting of sepiapterin, L-citrulline, L-arginine, tetrahydrobiopterin and folic acid. Those cases may now effectively be treated with NOX5 inhibitor setanaxib (2-(2-Chlorophenyl)-4-[3-(di-methylamino)phenyl]-5-methyl-1H-pyrazolo[4,3-c]pyridine-3,6-dione) or ML090 (5,12-dihydroquinoxalino(2,3-B)quinoxaline), with molecular structure (I):

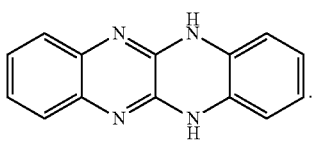

Structure (I)

Further NOX5 inhibitors suitable for inhibiting NOX5 in the patients suffering from the hypertension endotype are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from NOX5-dependent hypertension are for example perphenazine, ML171 and VAS2870.

The invention also relates to a method for detection of a hypertension endotype in a human patient suffering from essential arterial hypertension, wherein said endotype is defined by an increased level of circulating NADPH oxidase 5 protein (NOX5) compared to the level of circulating NOX5 in a human subject not suffering from hypertension, the method comprising the steps of:
(a) obtaining a plasma sample from the human patient who suffers from essential arterial hypertension; and
(b) measuring NOX5 in the plasma sample of step (a) using a protein detection assay and determining the concentration of NOX5 in the plasma sample in pg NOX5 per ml plasma,
wherein it is concluded that the human patient suffers from the hypertension endotype if the concentration of NOX5 as determined in step (b) is at least 160 pg NOX5 per ml of the plasma sample. Alternatively, the threshold level for the NOX5 is defined in enzyme activity per ml plasma.

Further, the invention relates to a method for the detection of a hypertension endotype in a human patient suffering from essential arterial hypertension, wherein said endotype is hypertension characterized by being
  accompanied by renal vascular leakage as established by the occurrence of microalbuminuria; or
  associated with the risk for developing renal vascular leakage apparent as development of microalbuminuria,
the method comprising the steps of:
(a) obtaining a fluid sample from the human patient who suffers from essential arterial hypertension, selected from the group comprising plasma, blood and serum, wherein the fluid sample comprises circulating endothelial microparticles;
(b) isolating the endothelial microparticles from the fluid sample provided in step (a); and
(c) measuring NADPH oxidase 5 protein (NOX5) in the endothelial microparticles of step (b) using a protein detection assay and determining the concentration of NOX5 in the fluid sample in pg NOX5 per ml fluid sample,
wherein it is concluded that the human patient has the hypertension endotype if the concentration of NOX5 is at least 160 pg NOX5 per ml of the fluid sample. Alternatively, the threshold level for the NOX5 is defined in enzyme activity per ml plasma.

The invention further relates to a compound selected from the group consisting of sepiapterin, L-citrulline, L-arginine, tetrahydrobiopterin, folic acid and a NOX5 inhibitor, in particular a NOX5 inhibitor based on quinoxaline such as NOX5 inhibitor 5,12-dihydroquinoxalino(2,3-B)quinoxaline (ML090), for use in the treatment of a subject with essential arterial hypertension, in particular with NOX5-dependent hypertension. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from NOX5-dependent hypertension are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870. The invention relates to a method for treating NADPH oxidase 5 (NOX5)-dependent hypertension comprising administering one or more of the compounds sepiapterin, folic acid, L-citrulline, L-arginine and tetrahydrobiopterin to a human patient suffering from essential arterial hypertension, wherein the human patient has an NOX5 plasma concentration of at least 160 pg NOX5 per ml plasma. In particular, comprising administering sepiapterin.

The invention relates to a method for treating NADPH oxidase 5 (NOX5)-dependent hypertension comprising administering an NOX5 inhibitor to a human patient suffering from essential arterial hypertension, wherein the human patient has an NOX5 plasma concentration of at least 160 pg NOX5 per ml plasma. In particular, comprising administering NOX5 inhibitor 5,12-dihydroquinoxalino(2,3-B)quinoxaline (ML090) to a human patient suffering from essential arterial hypertension, wherein the human patient has an NOX5 plasma concentration of at least 160 pg NOX5 per ml plasma. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from NOX5-dependent hypertension are for example perphenazine, ML171 and VAS2870.

In addition, the invention relates to administering an effective amount of one or more of sepiapterin, folic acid, L-citrulline, L-arginine and tetrahydrobiopterin to a human patient to treat NADPH oxidase 5 (NOX5)-dependent hypertension. In particular administering sepiapterin.

The invention also relates to administering an effective amount of an NOX5 inhibitor, in particular 5,12-dihydroquinoxalino(2,3-B)quinoxaline (ML090), to a human patient to treat NADPH oxidase 5 (NOX5)-dependent hypertension.

The invention further relates to a compound selected from the group consisting of sepiapterin, L-citrulline, L-arginine, tetrahydrobiopterin, folic acid and a NOX5 inhibitor, in particular a NOX5 inhibitor based on quinoxaline such as NOX5 inhibitor 5,12-dihydroquinoxalino(2,3-B)quinoxaline (ML090), for use in the treatment of a subject with essential arterial hypertension, in particular with NOX5-dependent hypertension. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the NOX5-dependent hypertension are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

In a further embodiment, the invention relates to the use of an aged NOX5 knock-in an animal model to discover and develop therapeutics and diagnostics for the use in NOX5- and uncoupled NOS-dependent (essential arterial) hypertension.

The invention also relates to the use of a mouse with knocked-in human Nox5 gene to discover and develop therapeutics and methods for detection, for the use in NOX5-dependent hypertension in a subject.

LEGEND TO THE FIGURES

Figure 1B:
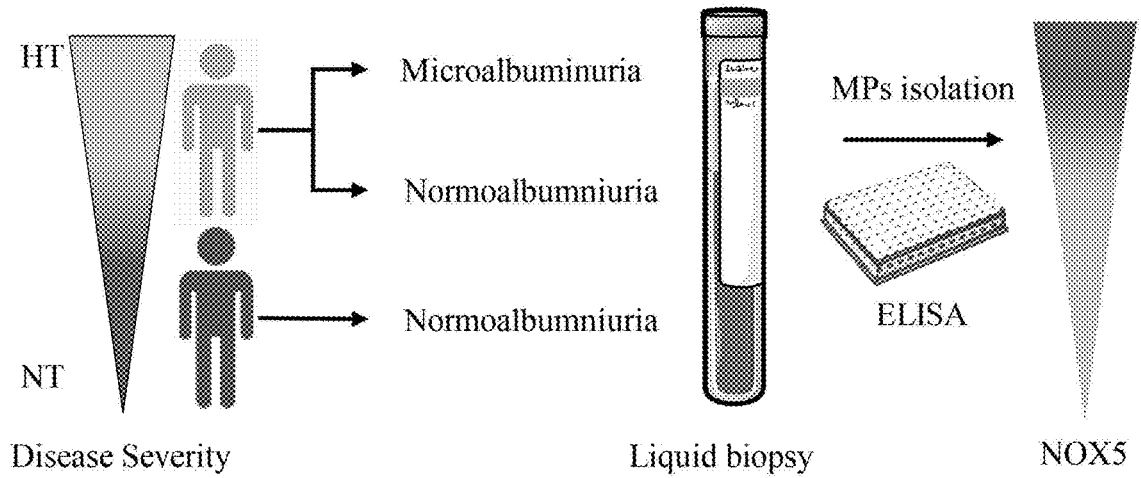
Figure 1C:
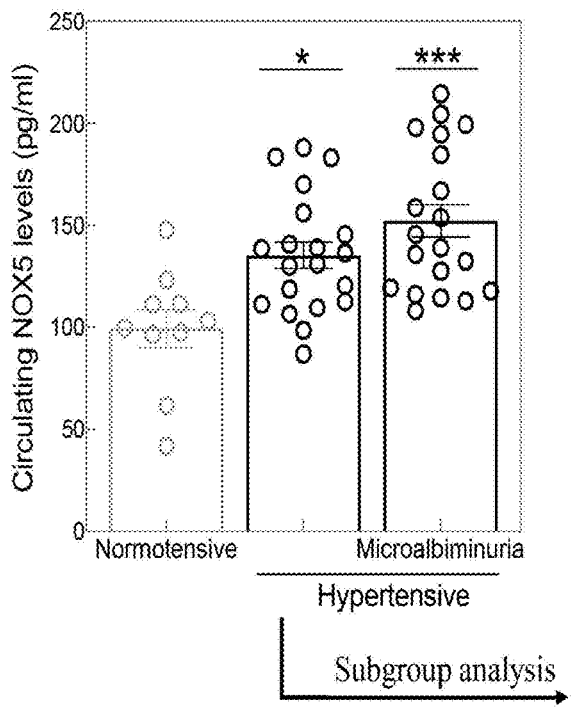
Figure 1D:
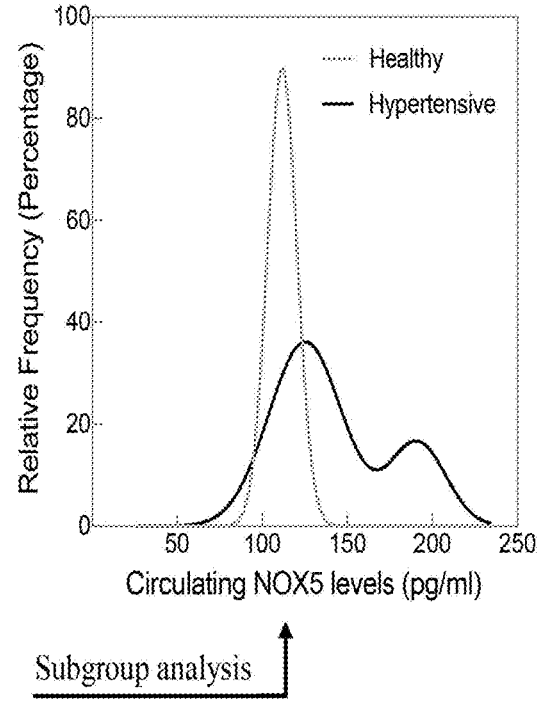

FIG. 1A-D. Identification of NOX5 as direct neighbour of endothelial NO-cGMP signalling and clinical validation in hypertension. FIG. 1A. NOX module was constructed by $1^{st}$ neighbour subnetwork pruned based on SPD (the middle panel) where NOX isoforms (gray nodes) and NO-cGMP related proteins (light-gray nodes) were used as seed nodes. The resulting NOX module was confirmed with two disease module identification methods, global modularity optimization (the left panel) and the agglomerative local method (the right panel). All the methods identified NOX5 as the closest link to NO-cGMP signalling and excluded NOX1-4 and all other known ROS sources (not shown). FIG. 1B. NOX5 levels in endothelial microparticles (MPs) isolated from plasma of normo-tensive (NT), normo-albuminuric subjects and hypertensive (HT) normo-albuminuric and micro-albuminuric patients were measured by ELISA. FIG. 1C. NOX5 levels were increased in hypertensive patients with normo-albuminuria (n=20) compared to normotensive subjects (n=10). NOX5 levels were even higher in hypertensive patients with microalbuminuria (n=20). Comparison between groups was done by one-way ANOVA followed by Tukey's multiple comparisons test. FIG. 1D. Subgroup analysis of all hypertensive patients shows bimodal distribution (p=0.0007, two-tailed F-test, adjusted r-squared=0.9973). All data are represented as mean±S.E.M. of n independent experiments *P<0.05, ***P<0.001.

Figure 2A:
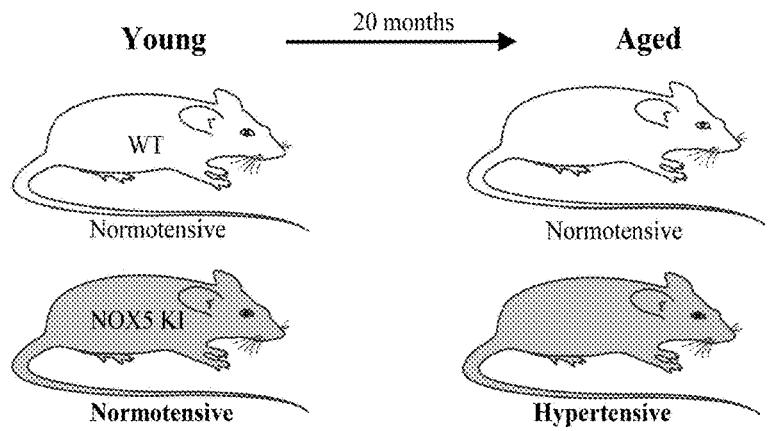
Figure 2B:
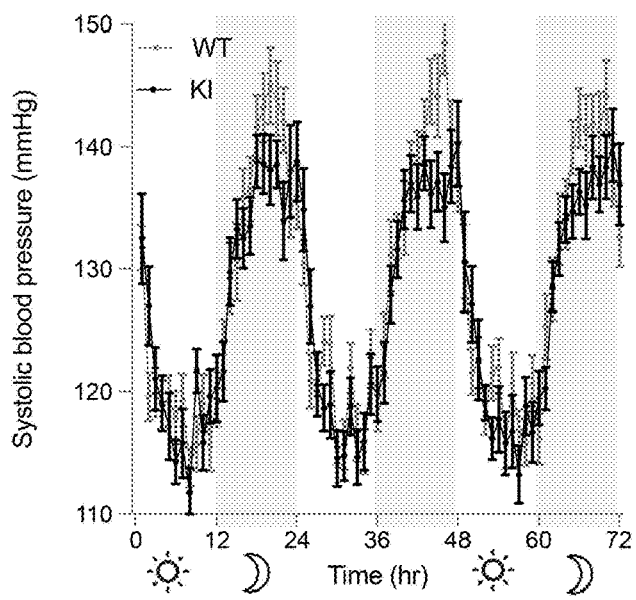
Figure 2C:
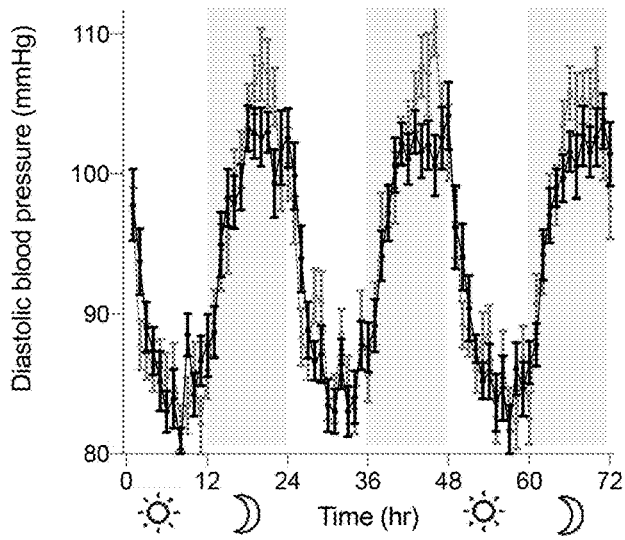
Figure 2D:
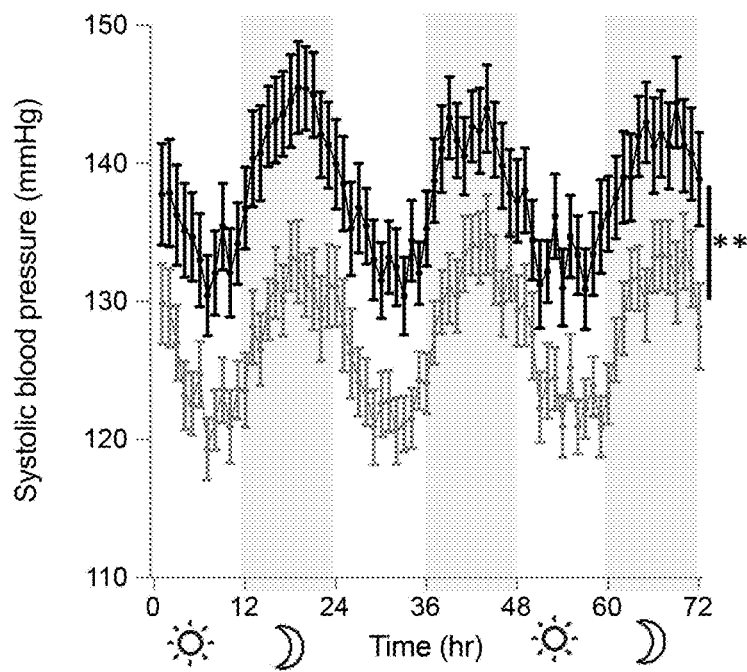
Figure 2E:
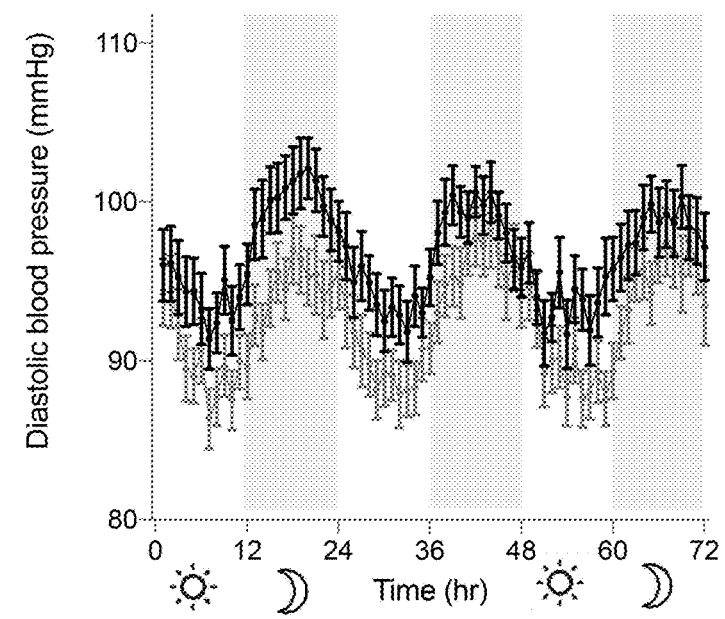

FIG. 2A-E. Preclinical validation of NOX5 in hypertension. FIG. 2A. Both young WT and NOX5 KI mice were normo-tensive however only KI mice become hypertensive upon ageing. FIG. 2B and FIG. 2C. There was no significant difference in systolic (B) and diastolic (C) blood pressure between young WT (n=19) and KI (n=20). FIG. 2D and FIG. 2E. Aged KI mice (n=33) had higher systolic (FIG. 2D) but similar diastolic (FIG. 2E) blood pressure compared to WT (n=31). Telemetry data were analyzed by two-way repeated measures ANOVA followed by Sidak's multiple comparisons test. All data are represented as mean±S.E.M. of n individual animals **P<0.01.

Figure 3A:
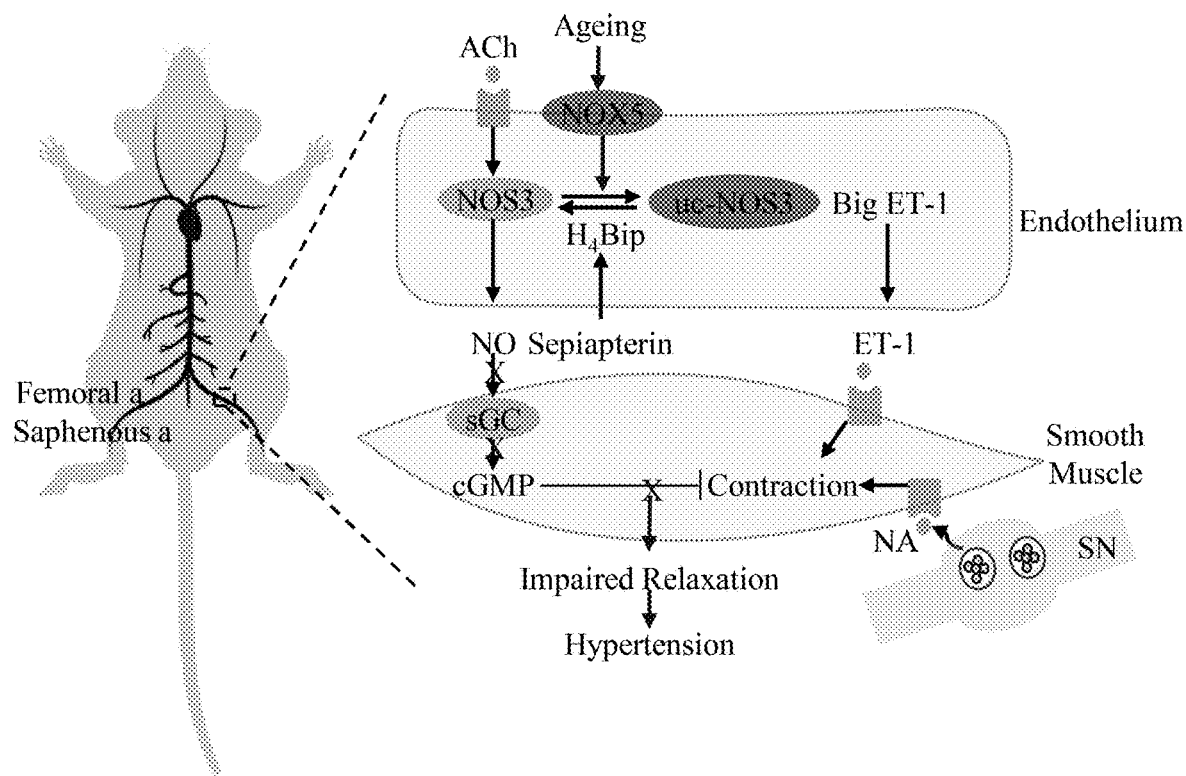
Figure 3B:
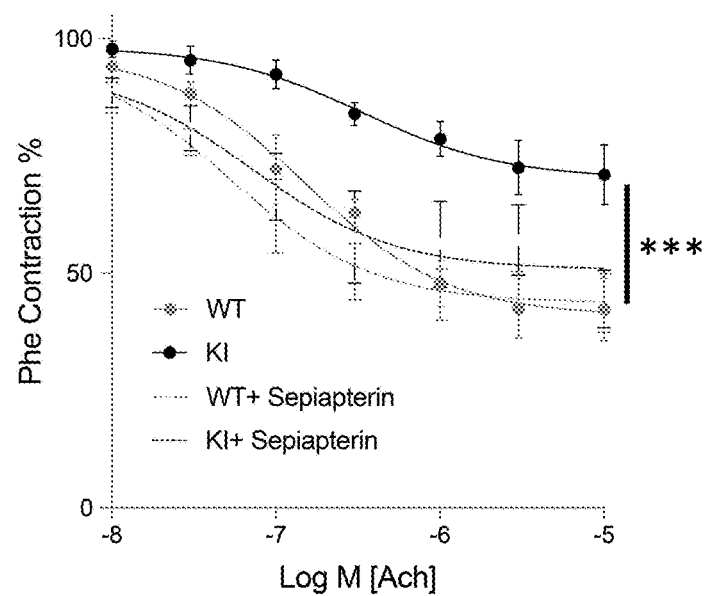
Figure 3C:
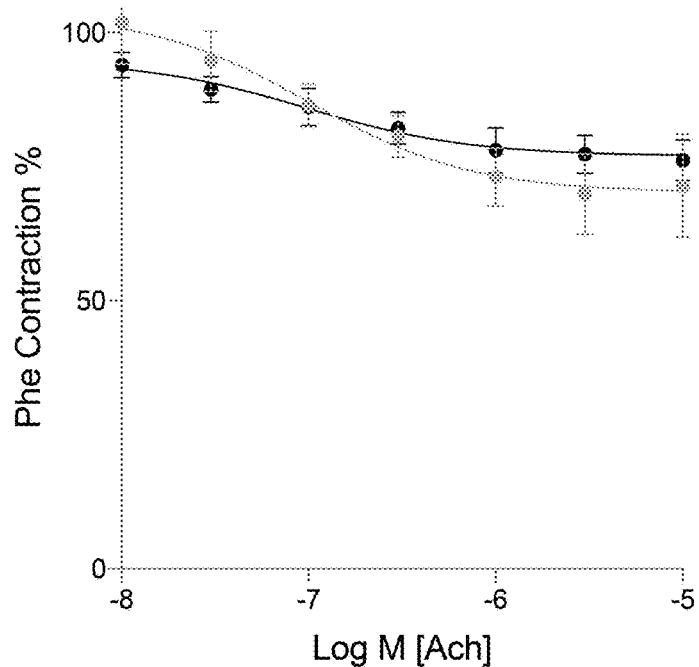

FIG. 3A-C. Endothelial NOX5 induces endothelial dysfunction and hypertension by uncoupling NOS.

FIG. 3A. Femoral arteries of aged KI mice (n=9) pre-contracted with phenylephrine (Phe) had less responsiveness to acetylcholine (Ach)-induced relaxation compared to WT (n=9) while pre-treatment with sepiapterin (100 μM) improved relaxation in KI (n=4) which was not different from WT (n=3).

FIG. 3B. Saphenous arteries of aged KI mice (n=9) pre-contracted with Phe showed no difference in Ach-induced relaxation compared to WT (n=8). Myograph data were analyzed by two-way ANOVA followed by Sidak's multiple comparisons test.

FIG. 3C. Schematic representation of NOX5-induced age-dependent hypertension. In ageing, endothelial NOX5 is activated and interferes with normal NO-cGMP signalling which results in impaired vascular smooth muscle relaxations and raised blood pressure.

Abbreviations: EC, endothelial cell; ET-1, endothelin-1; H4Bip, tetrahydrobiopterin; NA, noradrenaline; NOS3, endothelial nitric oxide synthase; SMC, smooth muscle cell; sGC, soluble guanylate cyclase; SN, sympathetic nerve. All data are represented as mean±S.E.M. of n individual animals ***P<0.001.

Figure 4:
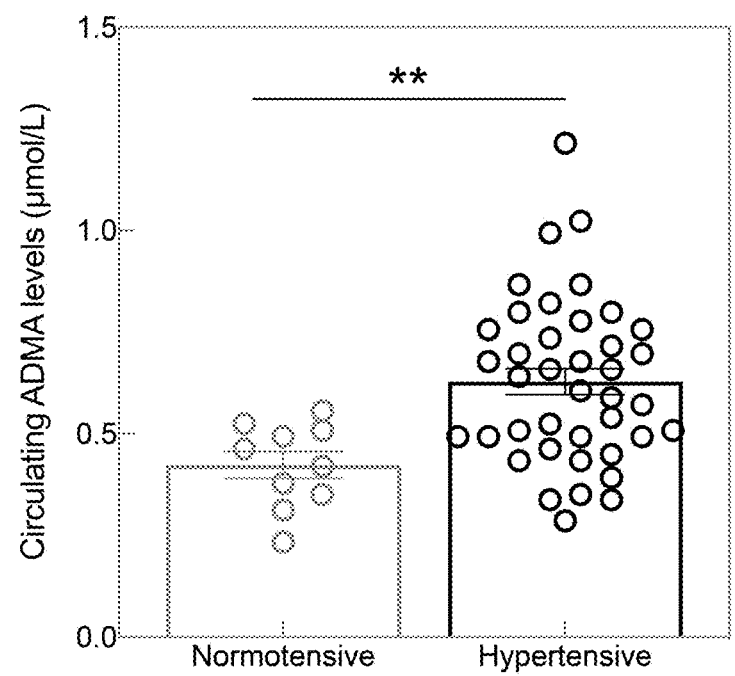

FIG. 4: Plasma ADMA levels in healthy and hypertensive subjects. ADMA levels were significantly higher in hypertensive patients (n=40) compared to healthy subjects (n=10). Comparison between the two groups was done by two-tailed unpaired T-test. All data are represented as mean±S.E.M, **P<0.01.

Figure 5A:
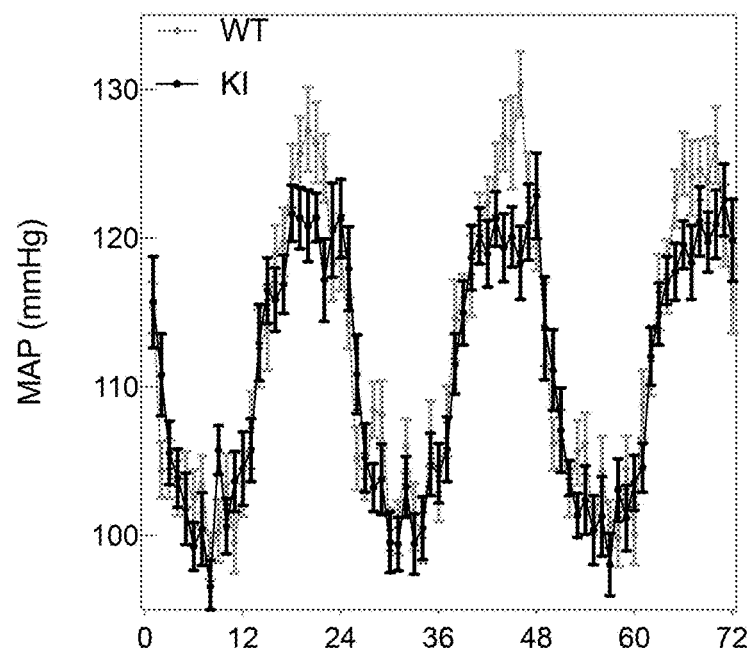
Figure 5B:
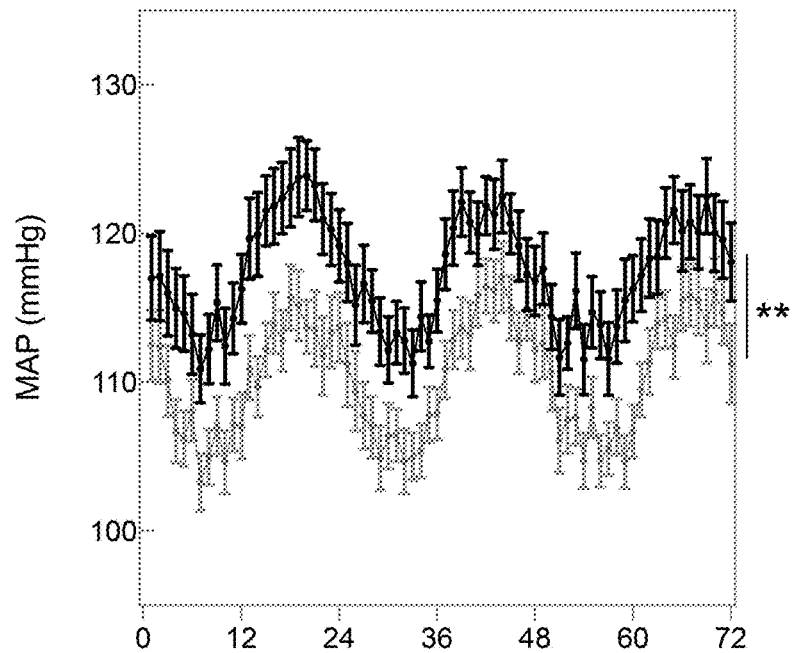
Figure 6A:
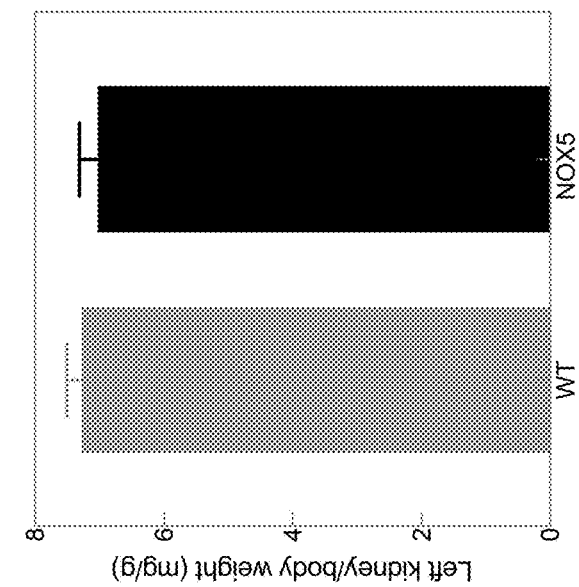
Figure 6B:
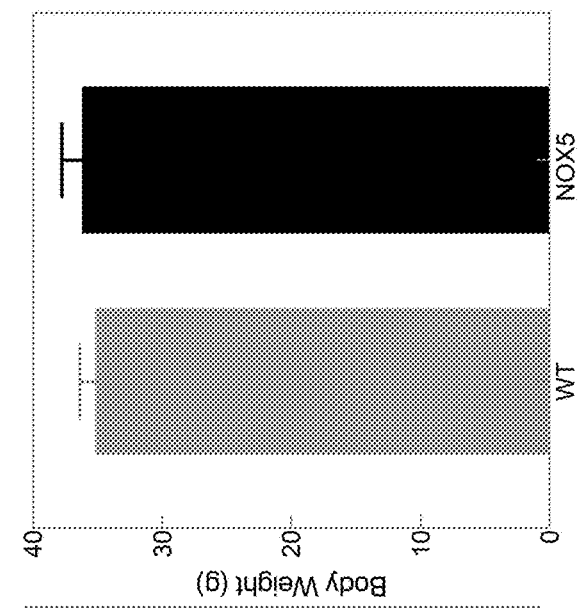
Figure 6C:
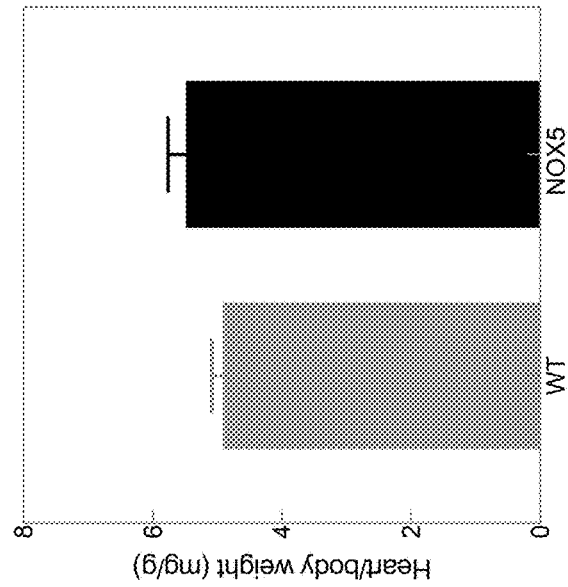
Figure 6E:
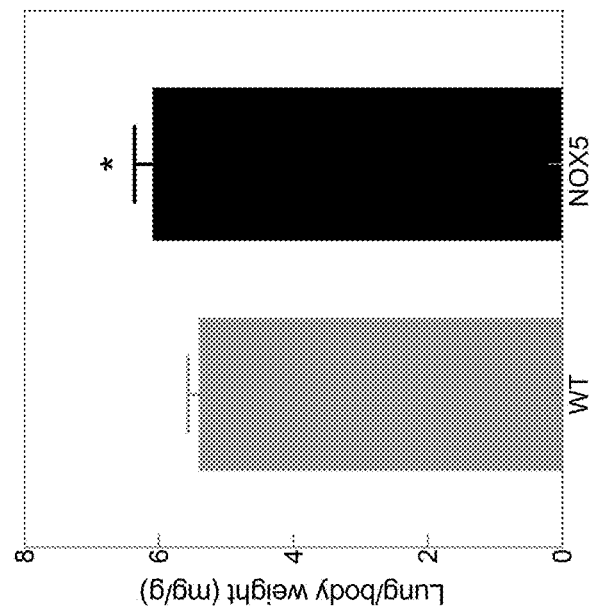
Figure 6D:
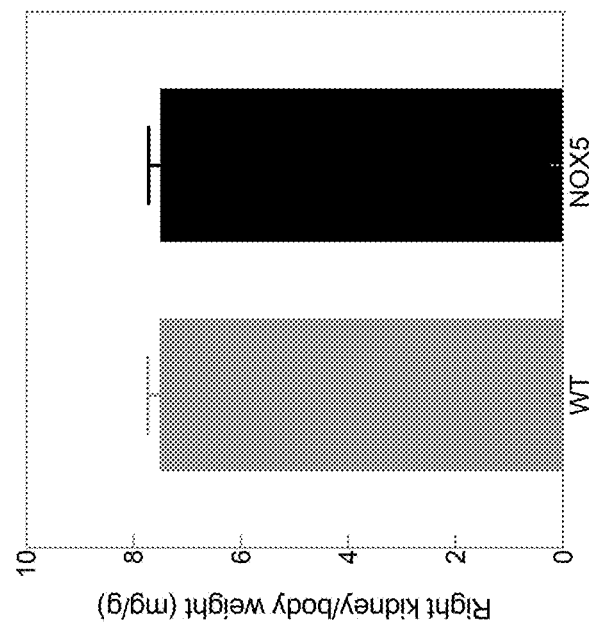

FIG. 5A-B: Mean arterial pressure (MAP) in young and aged WT and KI mice. FIG. 5A. There was no significant difference in MAP between young WT (n=19) and KI (n=20). FIG. 5B. Aged KI mice (n=33) had higher MAP compared to WT (n=31). Telemetry data were analyzed by two-way repeated measures ANOVA followed by Sidak's multiple comparisons test. All data are represented as mean±S.E.M. of n individual animals **P<0.01.

FIG. 6A-E: Body and organs weights in aged WT and KI mice. FIG. 6A, FIG. 6B, FIG. 6C, FIG. 6D and FIG. 6E. There was no difference in body, heart and kidneys weights between WT (n=24) and KI mice (n=20), however lung/body weight ratio was higher in KI mice. Comparison between groups were done by two-tailed unpaired T-test. All data are represented as mean±S.E.M. of n individual animals *P<0.05.

Figure 7A:
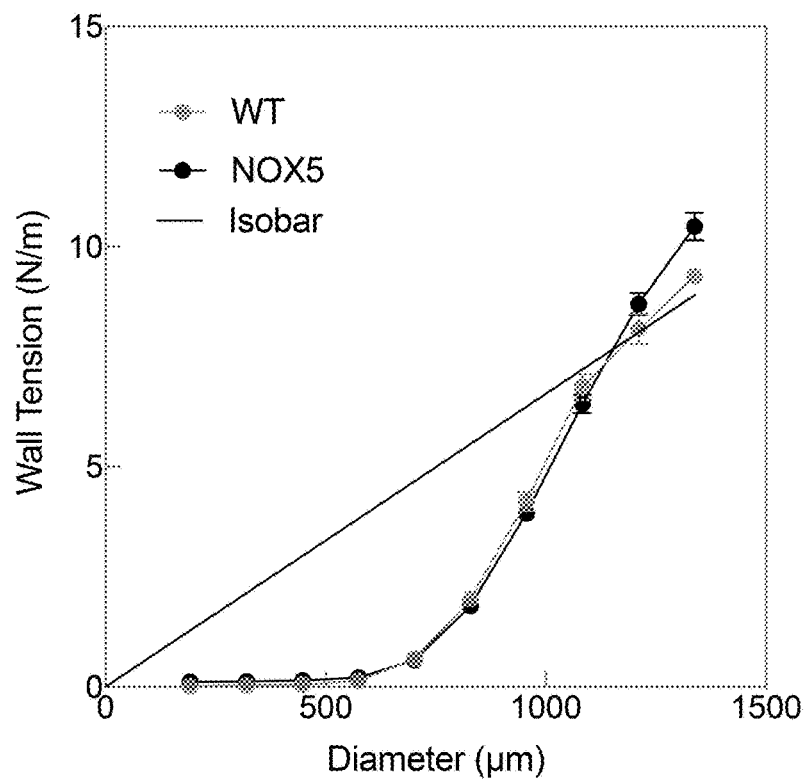
Figure 7B:
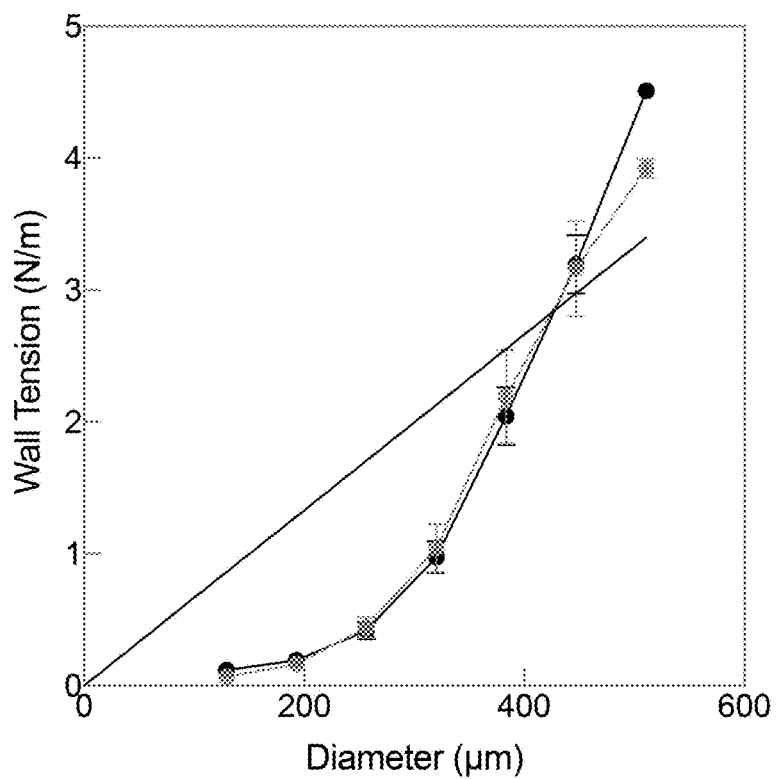
Figure 7C:
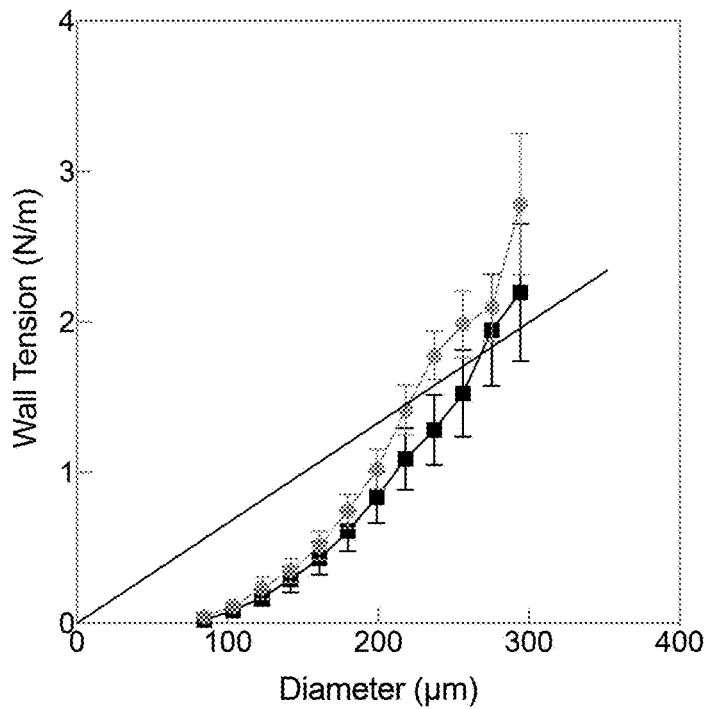

FIG. 7A-C: Arterial stiffness in aged WT and KI mice. FIG. 7A, FIG. 7B and FIG. 7C. The relation between resting wall tension and arterial lumen diameter did not differ between KI (n=9) and WT (n=9) mice in thoracic aortae (FIG. 7A), femoral arteries (FIG. 7B) and saphenous arteries (FIG. 7C). All data are represented as mean±S.E.M. of n individual animals.

Figure 8A:
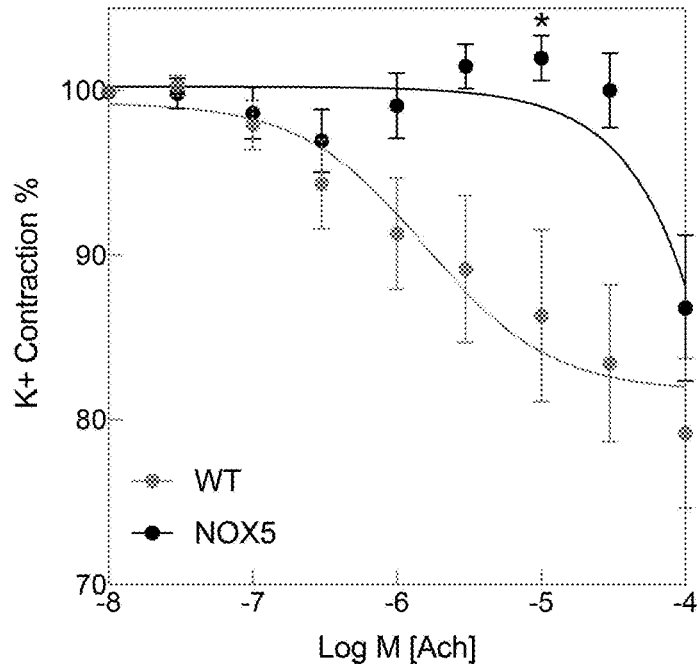
Figure 8B:
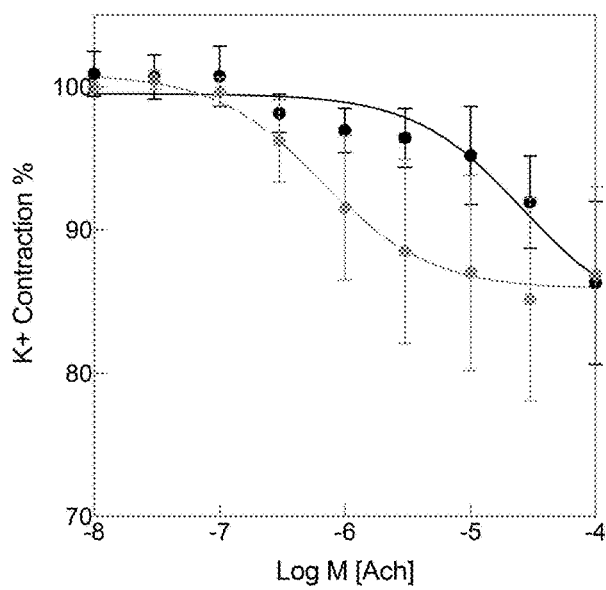
Figure 8C:
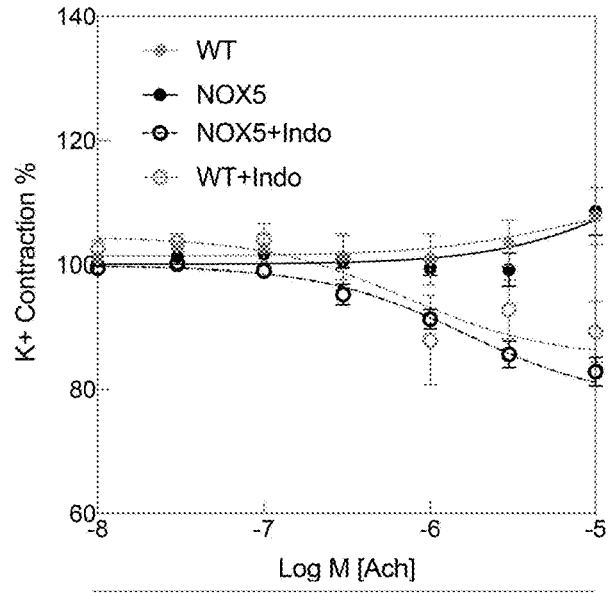
Figure 8D:
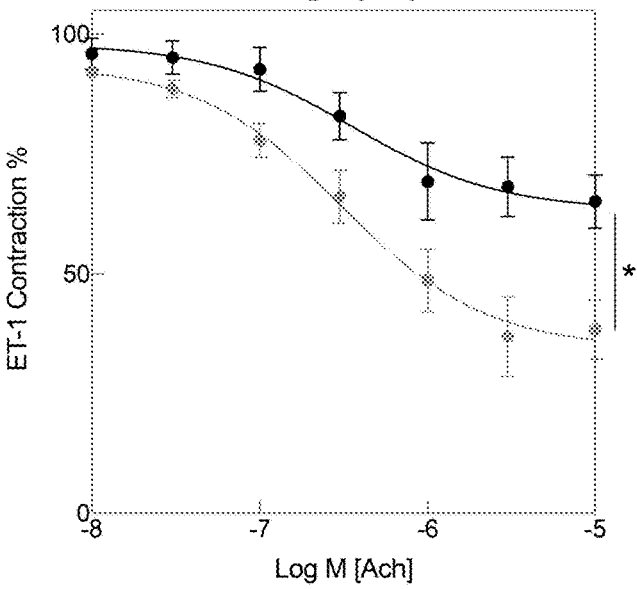
Figure 8E:
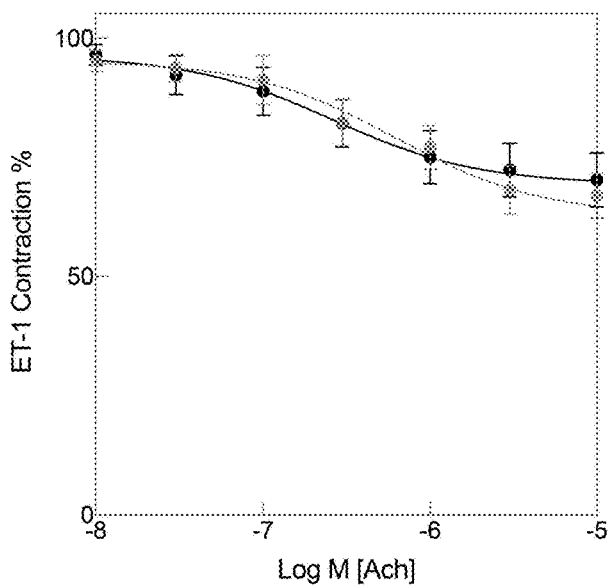
Figure 8F:
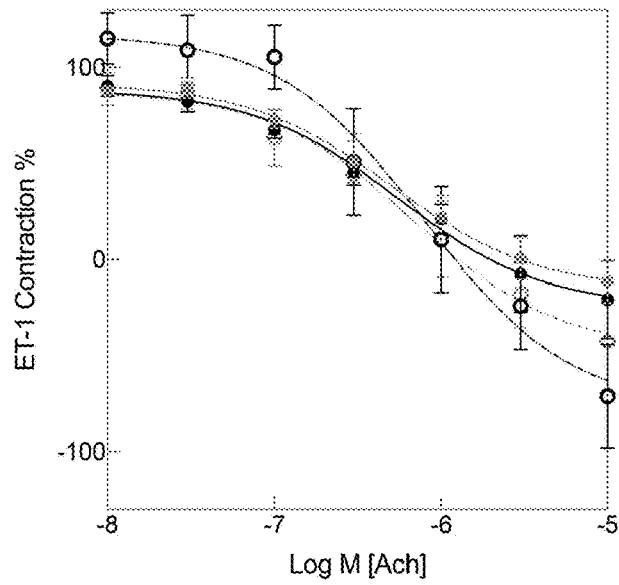
Figure 8G:
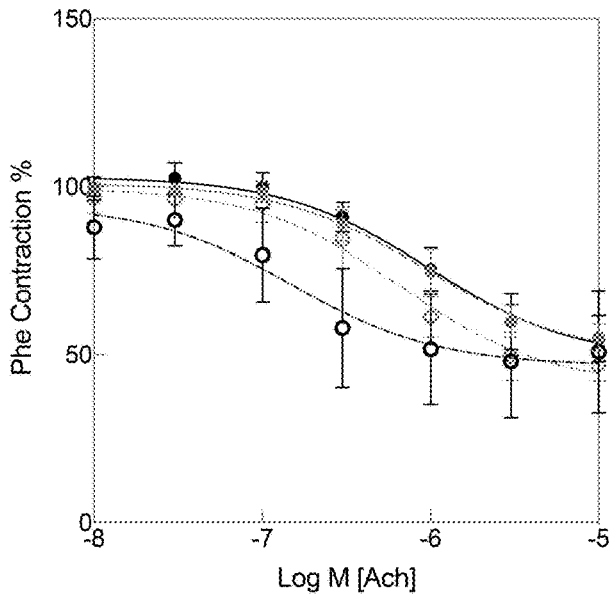

FIG. 8A-J: Acetylcholine (Ach)-induced relaxations in arteries of aged WT and KI mice. FIG. 8A, FIG. 8B and FIG. 8C. Ach-induced relaxations were impaired in femoral arteries (FIG. 8A) of aged KI mice (n=9) compared to WT (n=8-9) but not in saphenous arteries (FIG. 8B) and thoracic aortae (with/without indomethacin) (FIG. 8C) pre-contracted with K. D-F. Ach-induced relaxations were impaired in femoral arteries (FIG. 8D) of aged KI mice (n=9) compared to WT (n=8-9) but not in saphenous arteries (FIG. 8E) and thoracic aortae with/without indomethacin (FIG. 8F) pre-contracted with Endothelin-1. FIG. 8G. There was no difference in Ach-induced relaxations in thoracic aortae (with/without indomethacin) pre-contracted with phenylephrine between WT (n=9) and KI mice (n=9).

Figure 8H:
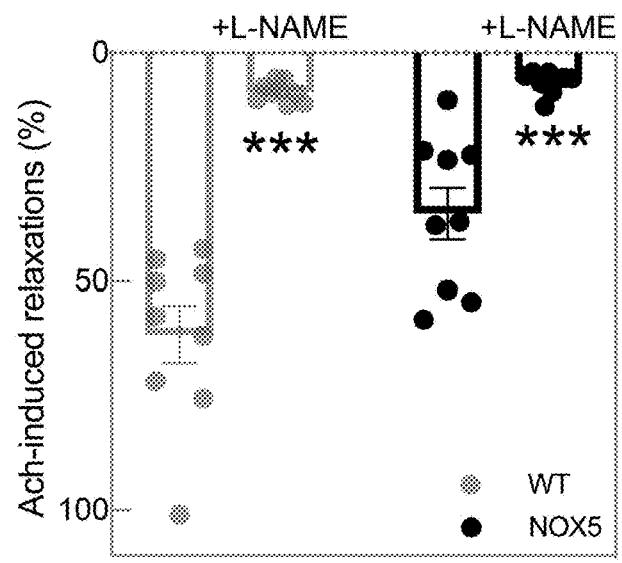
Figure 8I:
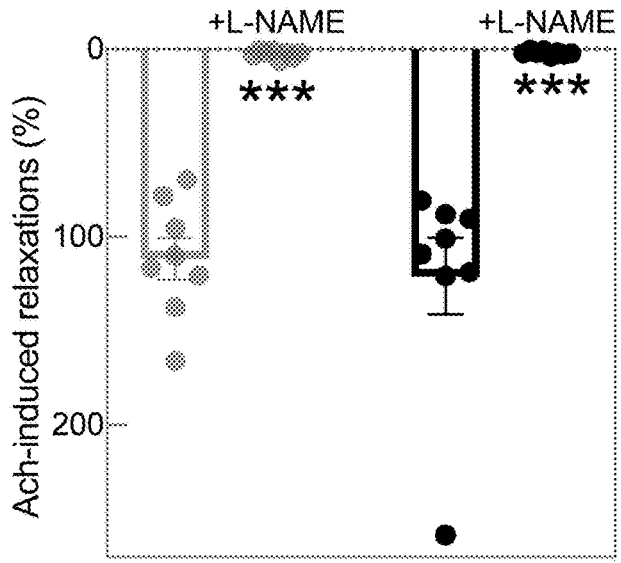
Figure 8J:
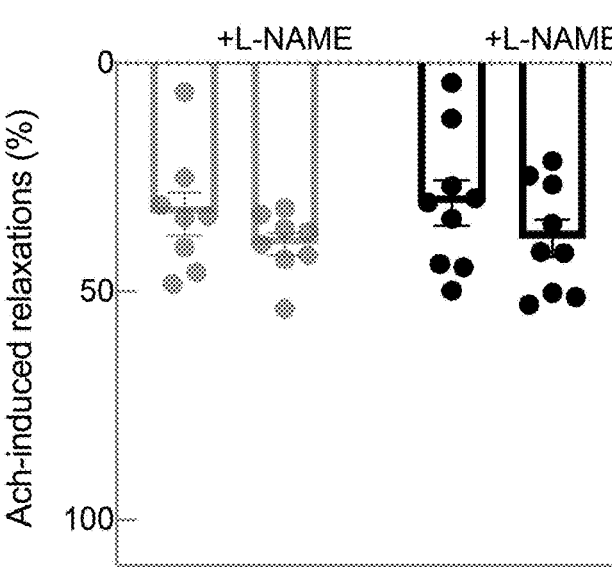

FIG. 8H, FIG. 8I and FIG. 8J. Ach-induced relaxations in arteries made to contract with Endothelin-1 were reversed by 100 μM L-NAME in femoral arteries (FIG. 8H) and thoracic aortae (FIG. 8I), but not saphenous arteries (FIG. 8J) of both aged KI mice (n=8-9) and WT (n=8-9). Myograph data were analyzed by two-way ANOVA followed by Sidak's multiple comparisons test. All data are represented as mean±S.E.M. of n individual animals *$P<0.05$.

Figure 9:
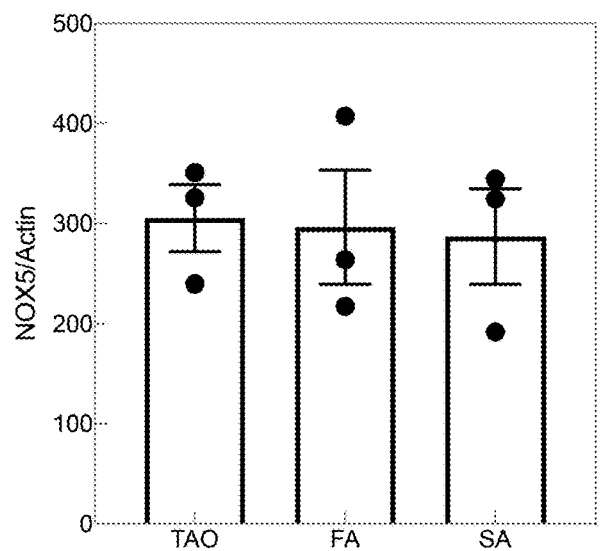
Figure 10A:
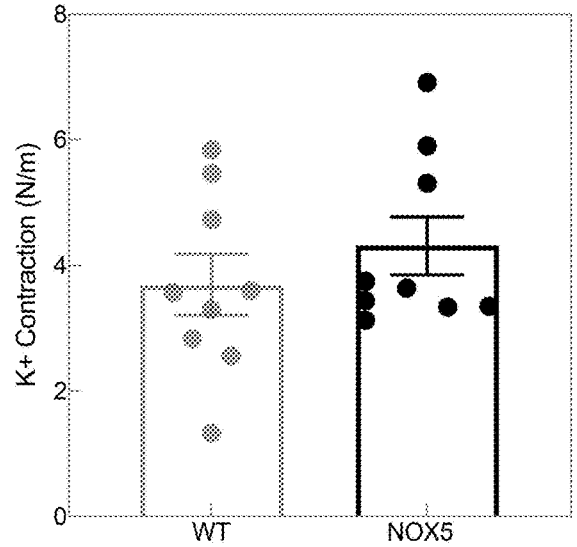
Figure 10B:
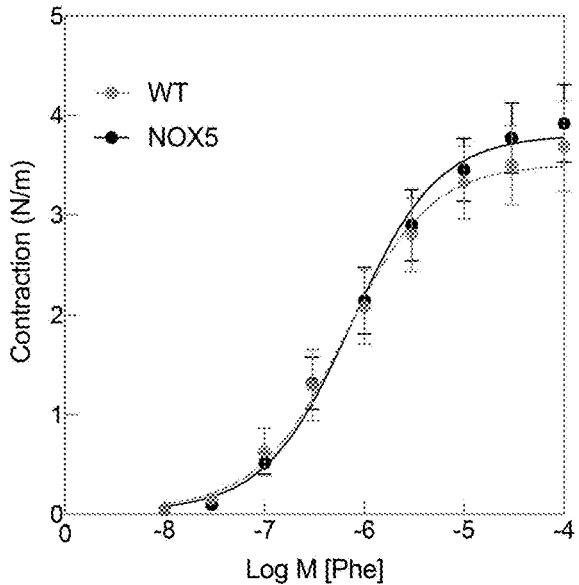
Figure 10C:
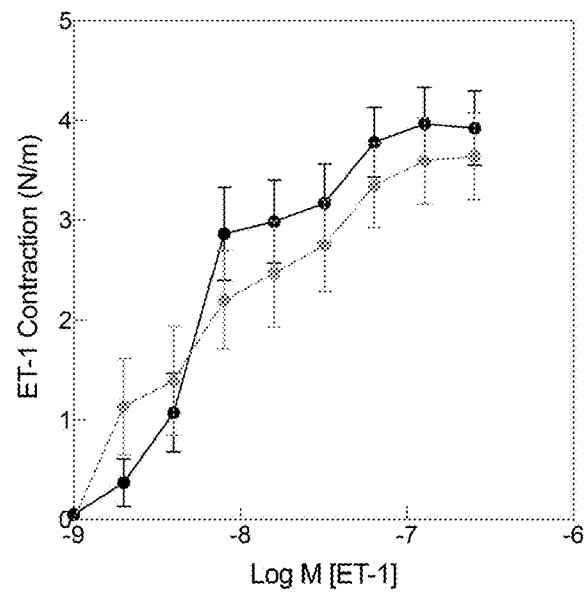
Figure 10D:
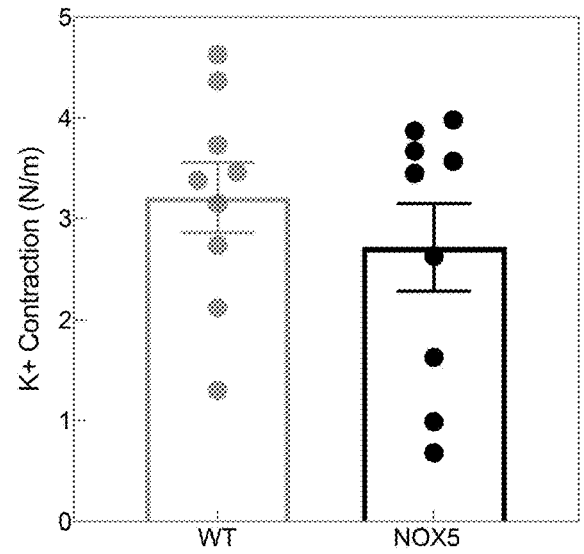
Figure 10E:
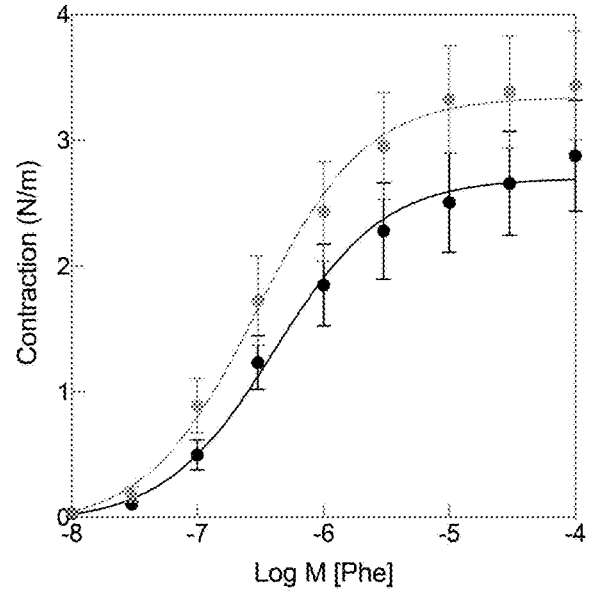
Figure 10F:
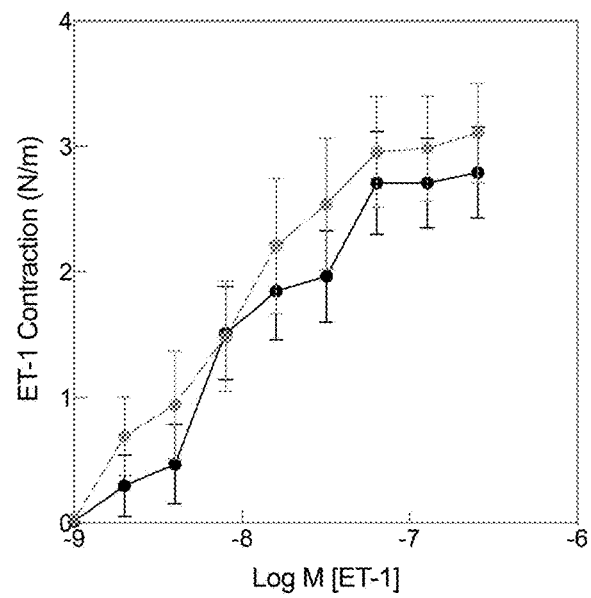
Figure 10G:
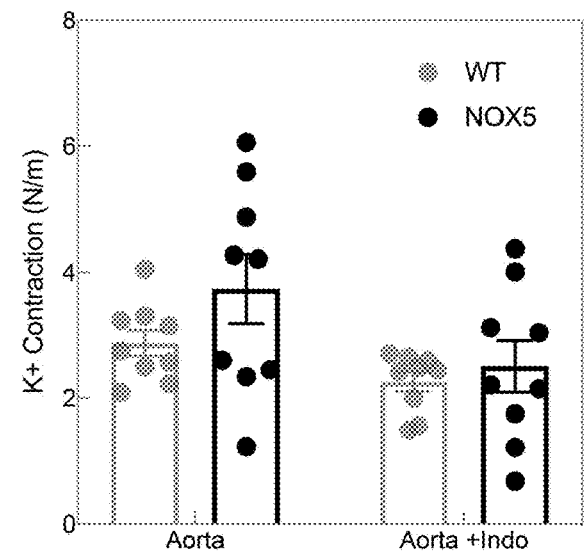
Figure 10H:
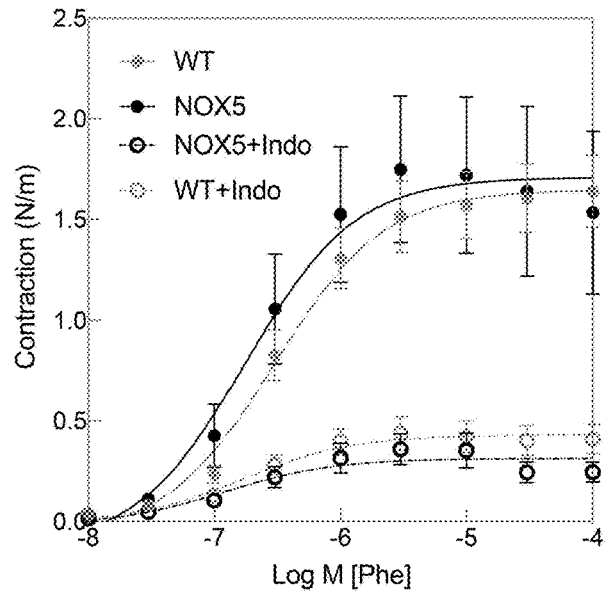
Figure 10I:
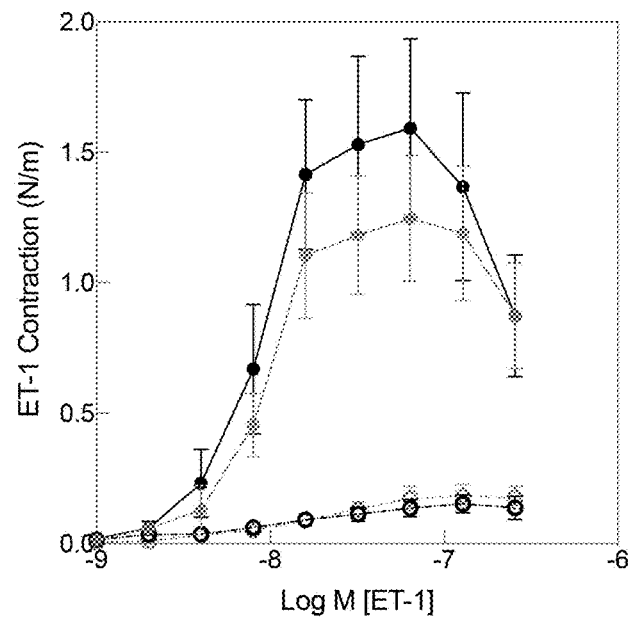

FIG. 9: qPCR of NOX5 in thoracic aortae (TAO), femoral arteries (FA) and saphenous arteries (SA) of aged KI mice. There was no difference in NOX5 gene expression between the three vessel types (n=3, each in duplicates). Comparison were done by one-way ANOVA. All data are represented as mean±S.E.M. of n individual animals.

FIG. 10A-I: Contractile responses in arteries of aged WT and KI mice. There was no difference in contractile responses to $K^+$, phenylephrine and endothelin-1 in femoral arteries (FIG. 10A, FIG. 10B and FIG. 10C), saphenous arteries (FIG. 10D, FIG. 10E and FIG. 10F) and thoracic aortae (with/without indomethacin) (FIG. 10G, FIG. 10H and FIG. 10I) between WT (n=8-9) and KI mice (n=9). Comparison between 2 groups in contractile responses to $K^+$ was done by two-tailed T-test. Other myograph data were analyzed by two-way ANOVA followed by Sidak's multiple comparisons test. All data are represented as mean±S.E.M. of n individual animals.

Figure 11A:
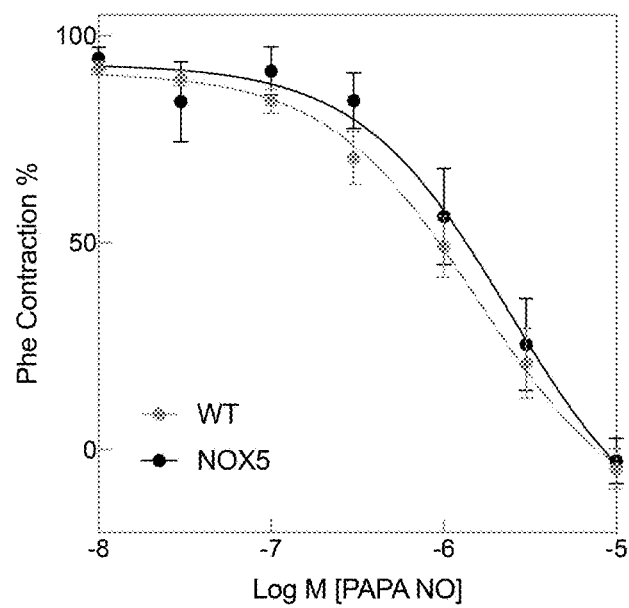
Figure 11B:
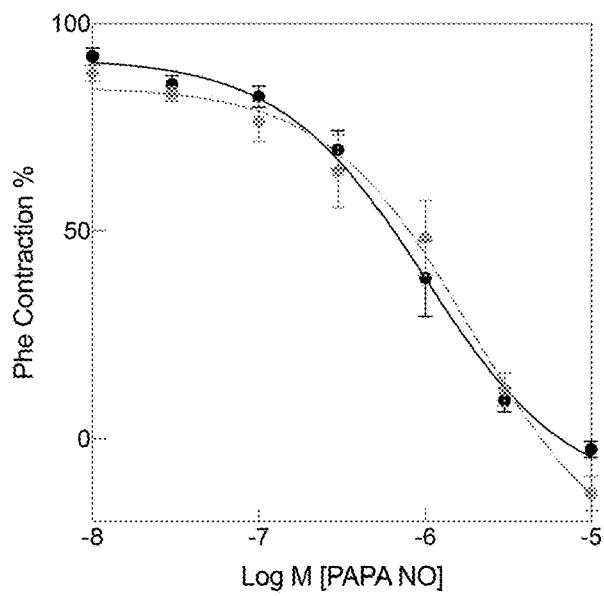
Figure 11C:
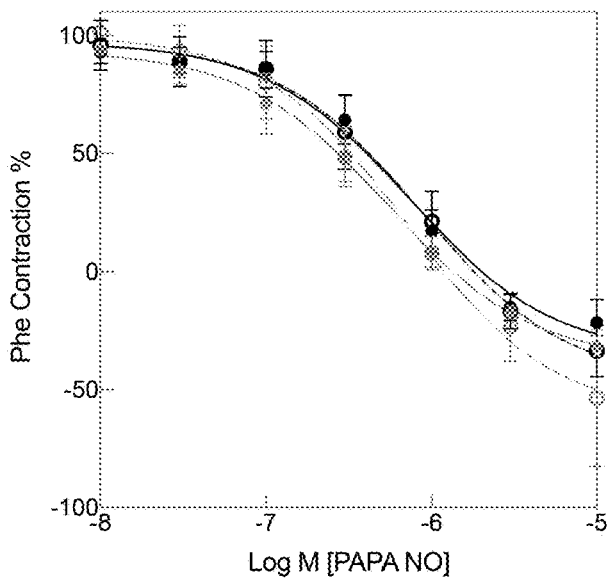

FIG. 11A-D: Endothelium-independent relaxations in arteries of aged WT and KI mice. FIG. 11A, FIG. 11B and FIG. 11C. Relaxations induced by the NO donor, PAPA NO (0.01-10 μM), in femoral arteries (FIG. 11A), saphenous arteries (FIG. 11B) and thoracic aortae (with/without indomethacin) (FIG. 11C) did not differ between WT (n=8-9) and KI mice (n=9).

Figure 11D:
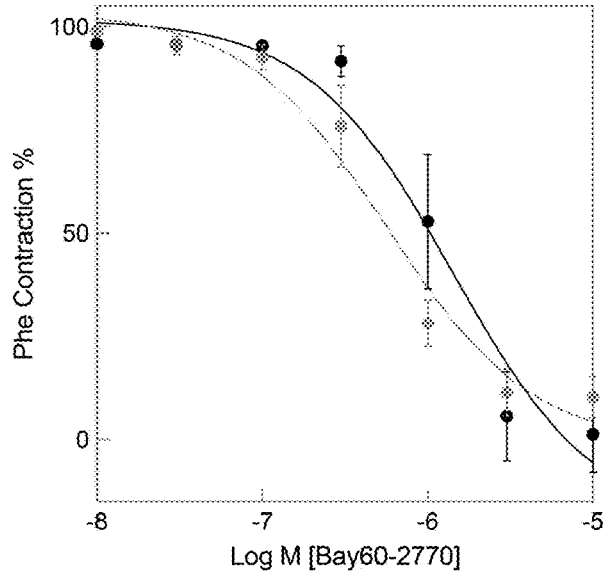

FIG. 11D. Relaxations induced by the apo-sGC activator, Bay60-2770 (0.01-10 μM), in femoral arteries did not differ between WT (n=4) and KI mice (n=4). Myograph data were analyzed by two-way ANOVA followed by Sidak's multiple comparisons test. All data are represented as mean±S.E.M. of n individual animals.

Figure 12A:
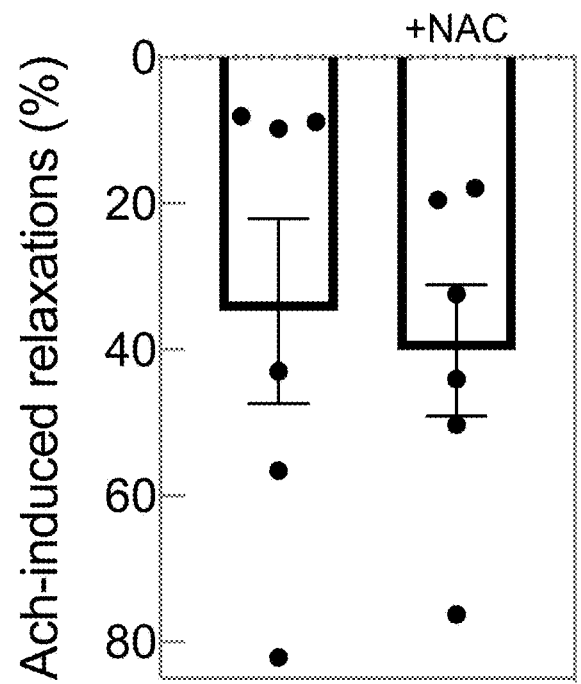
Figure 12B:
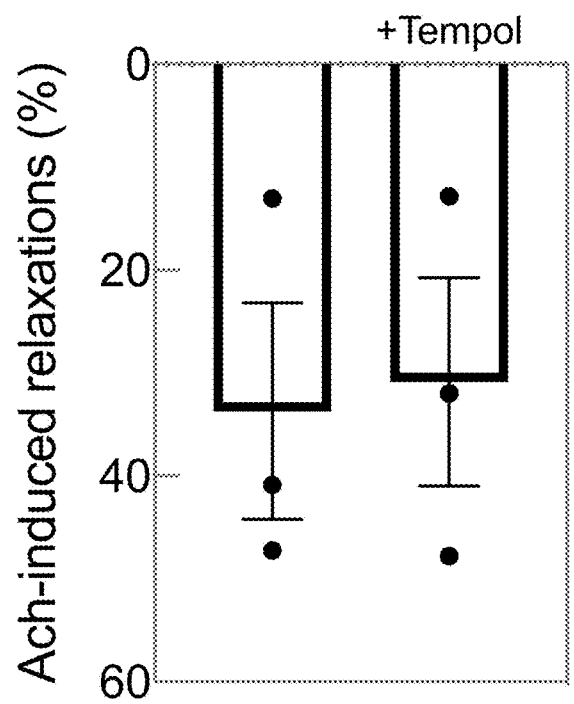

FIG. 12A-B. Acetylcholine (Ach)-induced relaxations in femoral arteries of aged KI mice treated with antioxidants. In segments of femoral artery (n=3-6) made to contract with 10 μM phenylephrine, relaxing effects of Ach (10 μM) were not reversed by 10 μM N-acetylcysteine (NAC) (FIG. 12A) or 100 μM tempol (FIG. 12B). Comparison between groups were done by two-tailed unpaired T-test. All data are represented as mean±S.E.M. of n individual animals.

Figure 13A:
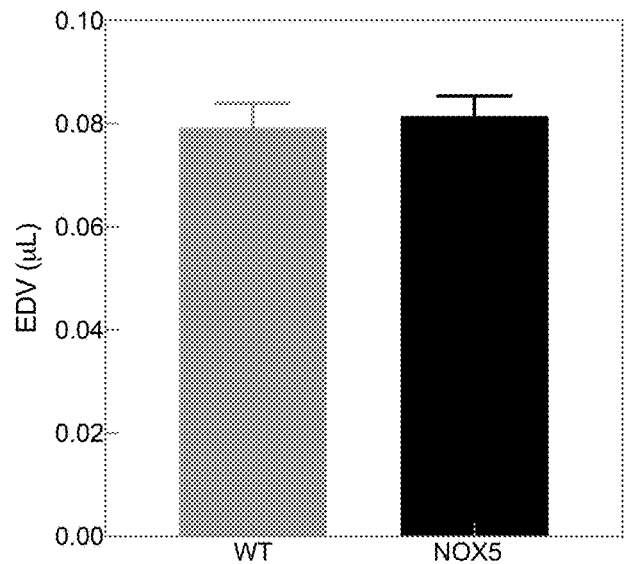
Figure 13B:
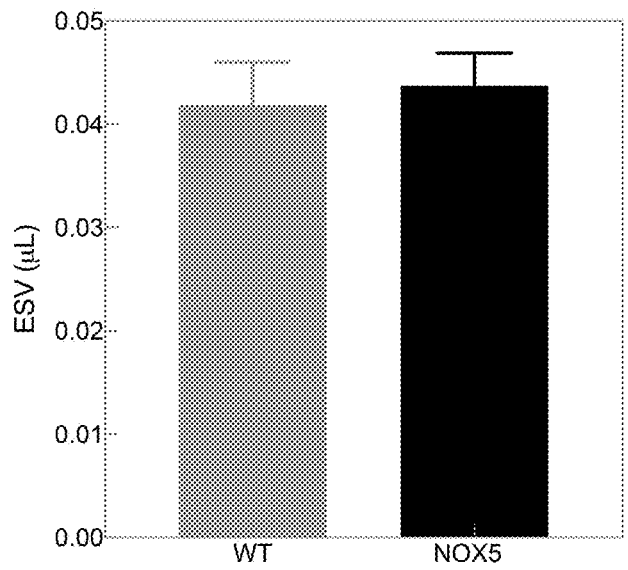
Figure 13C:
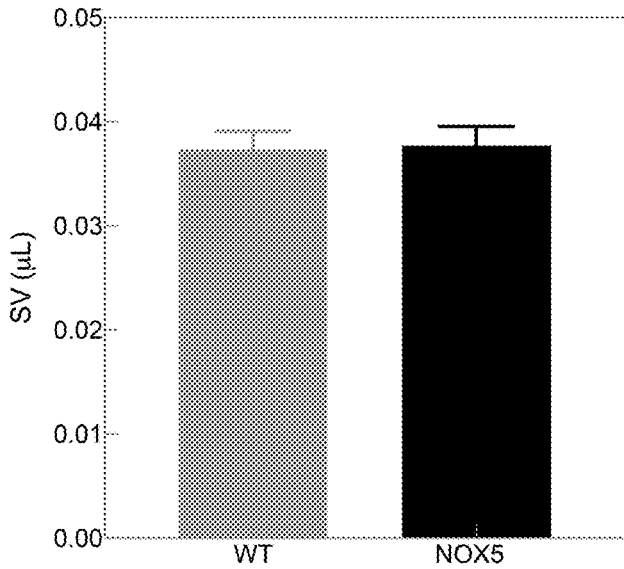
Figure 13D:
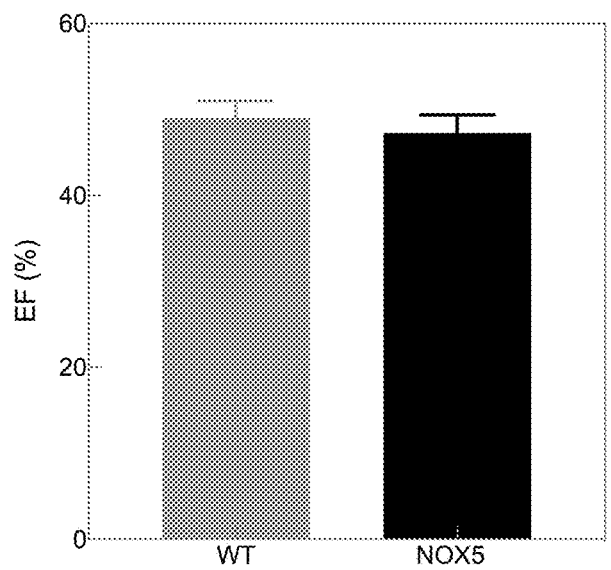
Figure 13E:
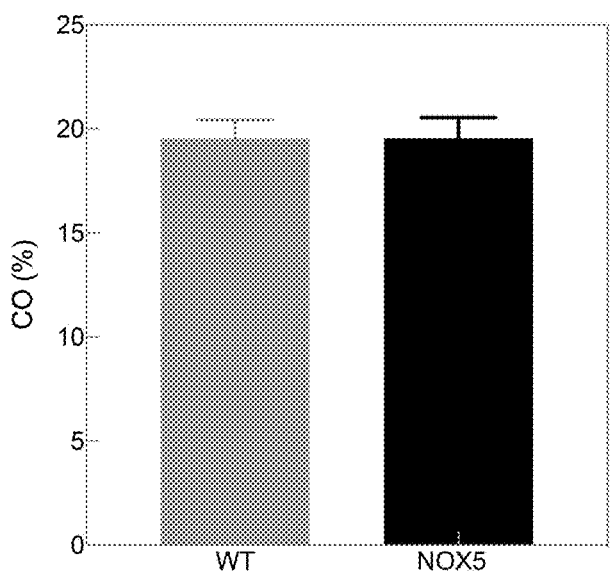
Figure 13F:
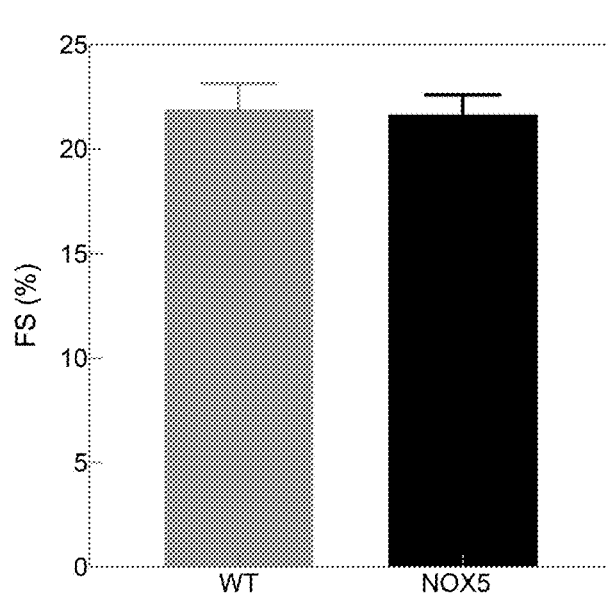
Figure 13G:
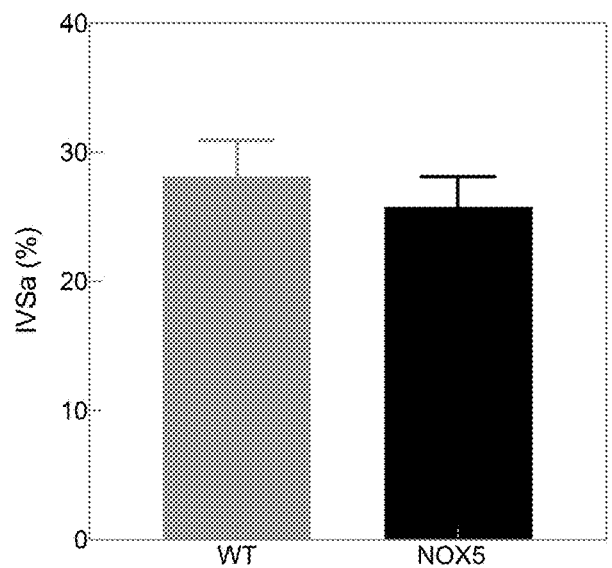
Figure 13H:
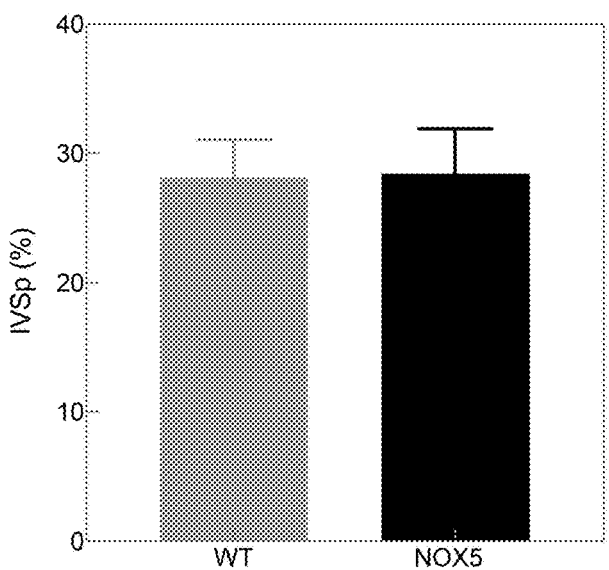
Figure 13I:
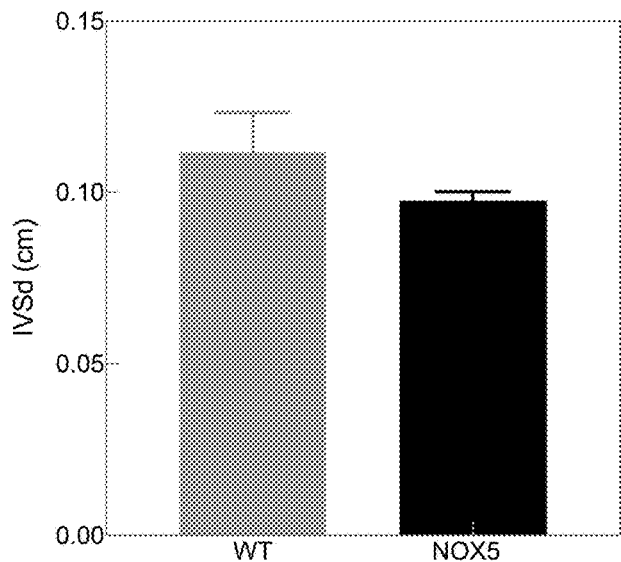
Figure 13J:
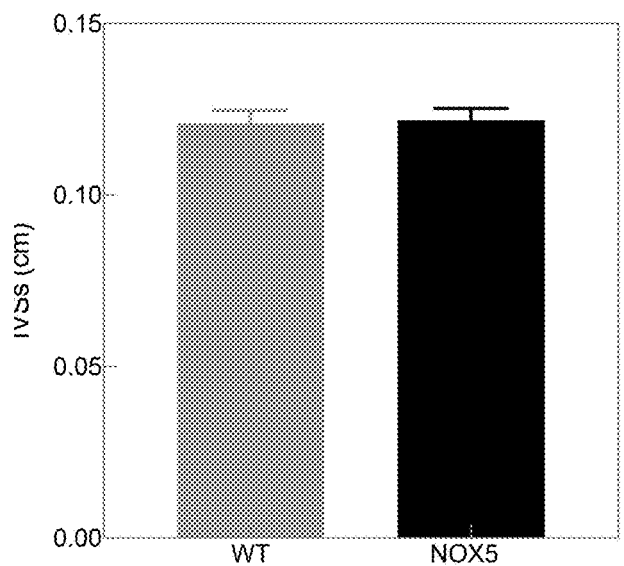
Figure 13K:
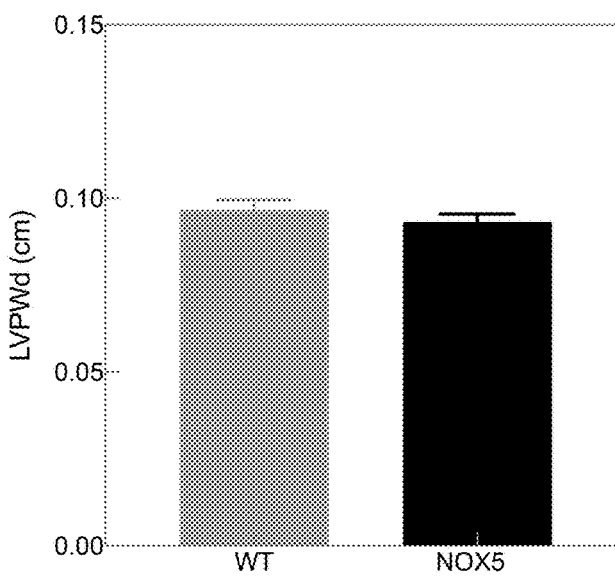
Figure 13L:
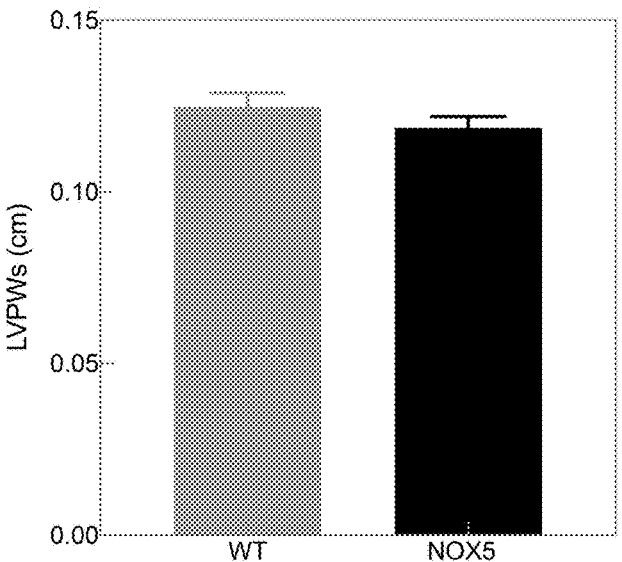
Figure 13M:
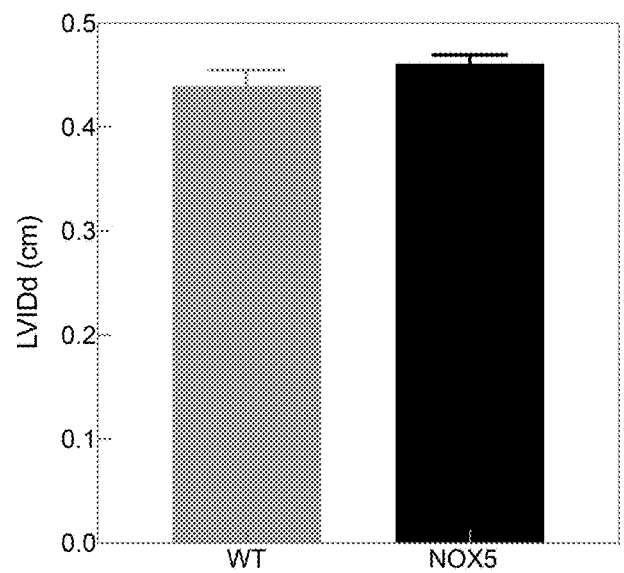
Figure 13N:
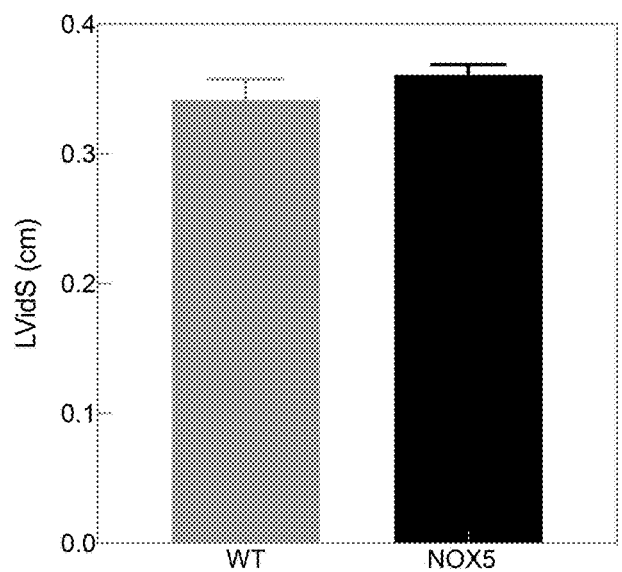

FIG. 13A-N: Echocardiography in aged WT and KI mice. There were no differences in all parameters (FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M and FIG. 13N) between WT (n=28) and KI mice (n=29). Comparison between groups were done by two-tailed unpaired T-test. All data are represented as mean±S.E.M. of n individual animals.

Figure 14A:
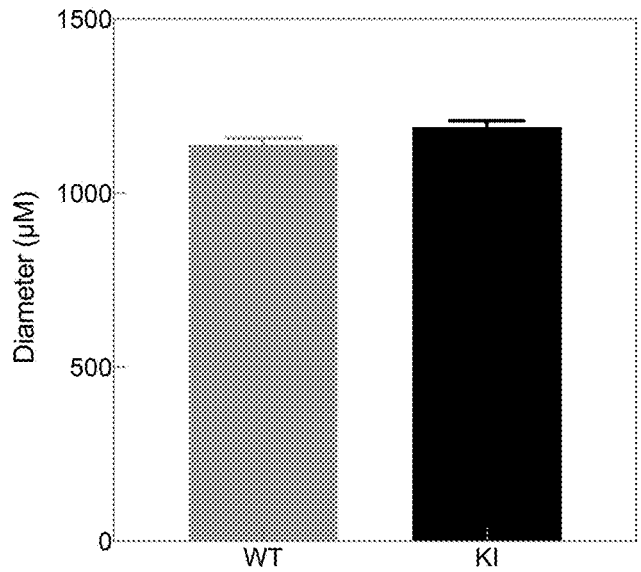
Figure 14B:
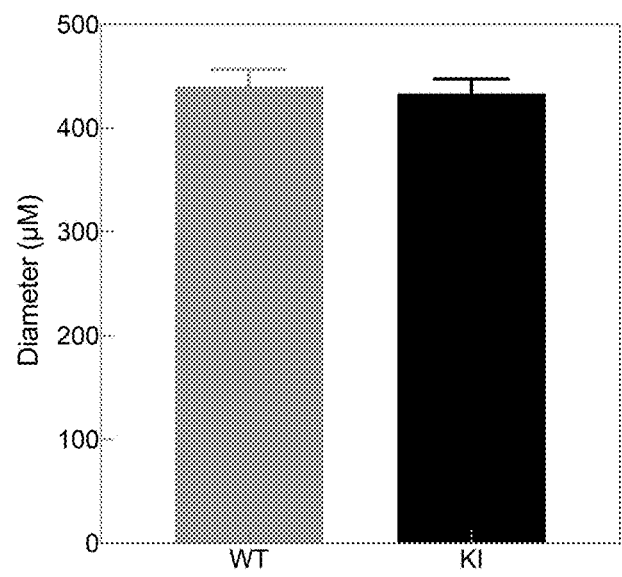
Figure 14C:
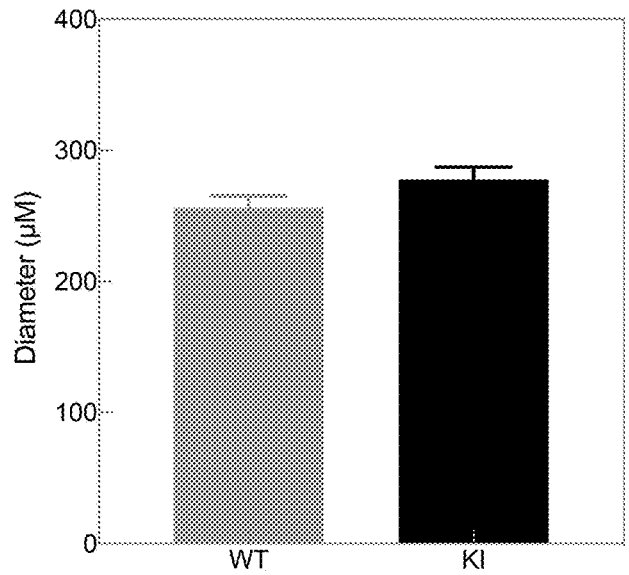

FIG. 14A-C: Arteries diameter in aged WT and KI mice. There were no differences in diameters of thoracic aortae (FIG. 14A), femoral arteries (FIG. 14B) and saphenous arteries (FIG. 14C), with or without indomethacin between WT (n=9) and KI mice (n=9). Comparison between groups were done by two-tailed unpaired T-test. All data are represented as mean±S.E.M. of n individual animals.

DETAILED DESCRIPTION OF THE INVENTION

To explore the possible link between NOX isoforms and hypertension and NO-dependent vasodilation, we constructed a pruned molecular subnetwork from the first neighbours of NOX family members and nitric oxide-cyclic GMP related proteins as seed nodes in the experimentally validated interactome obtained from the IID [19] interactome database. These included NOX1, NOX3, NOX4, NOX5, NOS1, NOS3, GUCYA1, GUCYA2, GUCYB1, PDE5A, PDE9A and PRKG1, but not NOX2 and NOS2.

The resulting subnetwork was further pruned according to the subnetwork-participation-degree (SPD) to correct for hub nodes (i.e. proteins that occurred mainly because of their high number of interactions in the whole network). This resulted in a disease module consisting of several connected components, which revealed that all NOX isoforms but NOX5 were excluded as close neighbour of endothelial NO-cyclic GMP signalling. NOX5 fell into the same connected component with the genes encoding the NO receptor, GUCYA1, GUCYA2 and GUCYB1, and with endothelial NOS (NOS3) (FIG. 1A). From IID, this connection is based on a physical interaction suggested by high-throughput affinity chromatography [20].

To cross-check our in-silico findings of a NOX disease module, we employed two additional computational network module identification methods, global modularity optimization and agglomerative local search, both of which have been top-performers in the recent Module Identification DREAM Challenge [21]. In brief, the global modularity optimization approach combines multiple module detection algorithms to avoid suboptimal partitions resulting from individual algorithms [22]. The agglomerative local method uses the SPICi algorithm [23] to optimize local density of modules around seed nodes. With all three in-silico methods we reached the same conclusion: Exclusion of all NOX genes, except NOX5, as a direct neighbour of endothelial nitric oxide-cyclic GMP signalling (FIG. 1A).

To test this causal endothelial NOX5 hypothesis for human hypertension, we enrolled consecutive outpatients with essential primary hypertension and a baseline estimated glomerular filtration rate (eGFR)≥30 mL/min/1.73 m². Study subjects were divided into 3 groups, healthy (n=10), hypertensive patients with normo-albuminuria (n=20) and hypertensive patients with moderately increased albuminuria (previously termed microalbuminuria) (n=20). The baseline characteristics of the patients are listed in Table 1. To measure NOX5 protein levels, circulating endothelial microparticles, i.e. membrane vesicles that are released from endothelial cells upon cellular activation or cell death and carry endothelial proteins [24], were isolated from plasma of the participants (FIG. 1B). We observed higher NOX5 protein levels in endothelial microparticles of hypertensive versus normotensive subjects and within hypertensive subjects, patients with microalbuminuria showed even higher NOX5 protein levels (FIG. 1C). These data suggest that NOX5 levels are associated with hypertension and correlate with disease severity. Hypertension is rather an umbrella term that may involve different molecular mechanisms all resulting in a similar phenotype, i.e. elevated blood pressure. NOX5-dependent hypertension may be such an endotype but apply only to a subset of patients [25-27]. We, therefore, performed a subgroup analysis of all hypertensive patients and, indeed, NOX5 levels showed a bimodal distribution (FIG. 1D). Based on this, approximately every fourth hypertensive patient would fall into a high NOX5 mechanotype, which according to the PPI interaction would cause NO-cGMP signalling dysfunction. In addition, we determined plasma ADMA levels, a biomarker of NOS uncoupling and endothelial dysfunction [28]. We found that ADMA levels were significantly increased in hypertensive patients compared to healthy subjects (FIG. 4), which is in agreement with previous findings [29, 30].

TABLE 1

Baseline characteristics in healthy subjects and hypertensive patients

|  | Healthy subjects (n = 10) | HTN patients without albuminuria (n = 20) | HTN patients with microalbuminuria (n = 20) | p value |
|---|---|---|---|---|
| Age (yrs) | 44 ± 4 | 56 ± 3 | 60 ± 3 | 0.012 |
| Men | 7 (70%) | 12 (60%) | 13 (65%) | 0.859 |
| Diabetes | 0 (0%) | 3 (15%) | 6 (30%) | 0.118 |
| BMI | 24.1 ± 0.94 | 26.1 ± 0.76 | 26.9 ± 0.73 | 0.096 |
| Smoking | 0 (0%) | 7 (35%) | 9 (32%) | 0.042 |
| T. Chol | 178 ± 11 | 193 ± 9 | 199 ± 8 | 0.358 |
| Triglycaride | 158 ± 42 | 146 ± 19 | 214 ± 27 | 0.139 |
| HDL | 50 ± 3 | 47 ± 3 | 41 ± 2 | 0.081 |
| LDL | 97 ± 11 | 117 ± 8 | 115 ± 9 | 0.360 |
| Fasting glucose | 96 ± 6 | 104 ± 8 | 120 ± 7 | 0.107 |
| Serum Cr | 0.81 ± 0.07 | 0.91 ± 0.05 | 1.01 ± 0.07 | 0.144 |
| Uric acid | 6.2 ± 0.53 | 6.1 ± 0.31 | 6.5 ± 0.29 | 0.656 |
| GFR | 87.0 ± 5.69 | 83.2 ± 3.57 | 79.3 ± 5.52 | 0.606 |
| FRS | 5.2 ± 1.73 | 8.2 ± 1.78 | 10.9 ± 1.9 | 0.168 |
| ACR | 0.008 ± 0.0009 | 0.010 ± 0.0001 | 0.059 ± 0.0008 | <0.001 |
| hsCRP | 0.56 ± 0.33 | 0.25 ± 0.03 | 0.52 ± 0.09 | 0.188 |
| Adiponectin | 16.0 ± 2.75 | 20.4 ± 3.08 | 18.5 ± 2.99 | 0.671 |
| NT-pro-BNP | 75.1 ± 11.95 | 80.9 ± 8.79 | 95.8 ± 16.9 | 0.572 |
| Medications | | | | |
| ACE-I | 0 (0%) | 4 (20%) | 1 (5%) | 0.143 |
| ARB | 0 (0%) | 14 (70%) | 16 (80%) | <0.001 |
| Beta-blocker | 0 (0%) | 2 (10%) | 9 (45%) | 0.005 |
| Thiazides | 0 (0%) | 6 (30%) | 8 (40%) | 0.069 |
| Statin | 1 (10%) | 3 (15%) | 7 (35%) | 0.185 |

Values are mean ± SEM or number (%).
HTN, hypertension;
BMI, body mass index;
T. Chol, total cholesterol (mg/dL);
HDL, high-density lipoprotein (mg/dL);
LDL, low-density lipoprotein (mg/dL);
Cr, creatinine (mg/dL);
GFR, glomerular filtration rate (mL/min/1.73 m2/year);
FRS, Framingham risk score (%);
ACR, albumin/creatinine ratio;
hsCRP, high-sensitivity C-reactive protein (mg/dL);
T-pro-BNP, N terminal pro-brain natriuetic peptide (pg/mL);
ACE-I, angiotensin-converting enzyme inhibitor;
ARB, angiotensin II receptor blocker;
CCB, calcium channel blocker.

In Table 1, the triglycerides are displayed in mg/dL; glucose levels are in mg/dL; uric acid is in mg/dL; adiponectin is in mg/dL.

We tested the possible role of NOX5 in endothelial NO-cGMP signalling dysfunction and hypertension in mice. Mice, however, lack the Nox5 gene. We therefore analyzed a knock-in mouse model expressing human Nox5 in its physiological endothelial cell location [31] (FIG. 2A). In young (9-15 weeks old) NOX5 KI mice of both genders (n=19-20), systolic blood pressure, diastolic blood pressure and mean arterial pressure (MAP) were, however, not different from age- and sex-matched wild type (WT) mice (FIGS. 2B, 2C and FIG. 5A). Upon aging (68-87 weeks), though, systolic blood pressure and mean arterial pressure were significantly elevated throughout the day in KI (n=33) compared to age- and sex-matched WT mice (n=31) (FIG. 2D and FIG. 5B). Diastolic blood pressure remained unmodified (FIG. 2E) as was heart to body weight ratio (FIG. 6A) indicating that there was no cardiac hypertrophy in KI mice, which is in line with the late (age-dependent) development of hypertension. In addition, cardiac hypertrophy does not necessarily exist with hypertension. For example, other hypertensive animal models such as eNOS knock-out (KO) mice do not have cardiac hypertrophy [32, 33]. This is also in agreement with clinical observations that not all hypertensive patients (sub-groups) have cardiac hypertrophy [34-36]. Notably there was no difference in blood pressure between male and female mice within the groups.

Taken together, our observations indicate that in mice, expression of NOX5 in the endothelium leads, upon aging, to a selective elevation of systolic arterial blood pressure. Having established the potential of NOX5 to induce a hypertensive phenotype, we proceeded to test the mechanistic link to vascular NO-cGMP signalling as suggested from the in-silico network analysis.

In thoracic aorta, femoral artery and saphenous artery isolated from aged knock-in (KI) and wild-type (WT) mice of both genders (n=9), we analyzed the structural, smooth muscle and endothelial vasomotor properties. Collectively, these blood vessels cover the entire range of large elastic conduit, muscular conduit and small muscular resistance-sized arteries, respectively. In thoracic aorta, femoral artery and saphenous artery of the aged animals, the relation between resting wall tension and arterial lumen diameter did not differ between KI and WT mice (FIG. 7 A-C). It is therefore unlikely that the blood pressure phenotype of the KI mice resulted from stiffening or inward remodelling of the conduit or resistance arteries. This is in agreement with previous studies that structural stiffening of arteries is not a general in rodent models of essential hypertension [37-40]. Also, clinical data especially from aged hypertensive patients is in line with this finding [41-44].

To test the effect of endothelial NOX5 on endothelium-dependent, NO-cGMP mediated relaxation, arterial segments were pre-contracted by either depolarization ($K^+$), α1-adrenergic activation (phenylephrine), or endothelin-1; vaso-relaxation was then induced by acetylcholine (Ach) the classical endothelium-derived relaxing factor stimulant [45]. In femoral arteries, irrespective whether pre-contracted with $K^+$, phenylephrine or endothelin-1, the amplitudes of Ach-induced relaxing responses were significantly smaller in KI compared to WT mice (FIGS. 3A, 8A and 8D). Conversely, in saphenous artery (FIGS. 3B, 8B and 8E) and thoracic aorta (FIGS. 8C, 8F and 8G), Ach-induced relaxing responses did not differ between KI and WT mice. When comparing ours to previous studies, the Ach-induced relaxation of saphenous arteries of both mice groups seemed attenuated [46-48]. There are two possible explanations for this discrepancy. First, we have used very old mice and other studies used young mice [46-48]. Second, we have used mice with mixed genetic background (80% 129I5v and 20% C57B16) and previous data showed that endothelium-dependent-relaxation is smaller in 129/Sv versus C57B16 mice [49].

In segments of thoracic aorta and femoral artery contracted with 256 nM endothelin-1, the relaxing effects of Ach were reversed by 100 μM L-NAME (a pharmacological inhibitor of NO synthases) and this did not differ significantly between preparations of KI and WT mice (FIGS. 8H and 8I). In the saphenous arteries of both types of mice, L-NAME did not modify the relaxing effects of Ach (FIG. 8J). This is in line with our earlier findings indicating that in these resistance-sized arteries Ach-induced relaxation is mediated by endothelium-dependent hyperpolarization but not NO [46-48].

To check whether this caliber specific effect on vasomotor function was due to differential expression of NOX5 along the systemic arterial tree, we measured NOX5 gene expression by quantitative PCR. There was, however, no difference in NOX5 gene expression between thoracic aorta, femoral arteries and saphenous arteries of NOX5 KI mice (FIG. 9). These data suggest an ageing-dependent dysfunction of endothelial NO-cGMP signalling due to NOX5 and that this effect is not uniformly distributed along the systemic arterial tree.

We next tested whether, alternatively, chronic changes in the underlying arterial smooth muscle layer could have contributed to the observed blood pressure and vasomotor phenotypes in aged NOX5 KI mice. Contractile responses to $K^+$ and the sensitivity and maximal responsiveness to phenylephrine and endothelin-1 did, however, not differ between KI and WT mice in all arterial segments (FIGS. 10 A-I). Also, the blunting of agonist-induced contractile responses by indomethacin was similar in the thoracic aorta of the KI and WT mice (FIG. 10 G-I).

To test which component of NO-cGMP signalling was most likely affected, we tested an uncoupling effect on endothelial NO synthase [50] or an oxidative damage of the NO receptor, soluble guanylate cyclase yielding oxidized or heme-free apo-sGC [51, 52]. To test for sGC/apo-sGC, relaxing responses to the NO donor compound and sGC stimulator, PAPA/NO (0.01-10 µM) [53], and to the aposGC activator, BAY 60-2770 (0.01-10 µM) [51], were analyzed. Neither the PAPA/NO (FIGS. 13 A-C) nor the BAY 60-2770 response (FIG. 11 D) differed between WT and KI mice. These observations suggested that sGC was not dysfunctional in aged NOX5 KI mice.

Uncoupling of endothelial NOS is considered a major cause of endothelial dysfunction characterized by decreased NO formation and increased superoxide production and occurs mainly when ROS oxidize the NOS cofactor tetrahydrobiopterin (H4Bip) [54]. When we incubated femoral arteries of aged NOX5 KI mice, pre-contracted with phenylephrine, with the H4Bip precursor sepiapterin (100 µM), Ach-induced relaxations were greatly improved and became indistinguishable from those in WT (FIG. 3A). Also, femoral arteries of aged NOX5 KI mice showed higher superoxide formation (as indicated by DHE staining) than WT and this increase was inhibited by pre-treatment with the NOS inhibitor, L-NAME.

We also tested whether the impaired Ach-induced relaxation in femoral arteries of NOX5KI mice could be reversed by adding antioxidants to the bath medium. Neither 10 µM N-acetylcysteine nor 100 µM tempol, however, were effective (FIG. 12). Collectively, these data suggest that endothelial NOX5 induces endothelial dysfunction by uncoupling of endothelial NOS leading to impaired endothelium-dependent relaxation of muscular conduit arteries and thus systolic hypertension (FIG. 3C).

In summary, based on human genetic, human clinical, and genetic preclinical mechanistic validation, we here report the first identified causal molecular mechanism of human systolic hypertension associated with ageing. This endotype affects approximately one in four patients and molecularly consists of a NOX5-induced uncoupling of endothelial NO synthase followed by an impaired endothelium-dependent vasodilation in muscular conduit arteries. Detection of elevated levels of NOX5 in circulating microparticles appears to serve as a mechanism-based liquid biopsy marker to stratify patients for therapeutic intervention. Based on our in vivo validation such an intervention may include the $H_4Bip$ precursor and NOS recoupling agent, sepiapterin and a NOX5 inhibitor [55-58].

Here we used a KI mouse model which expresses human NOX5 in endothelial cells and white blood cells mimicking, to a large extent, the physiological pattern of NOX5 expression in humans [31]. Expression of human NOX5 in mice led with ageing to severe systolic hypertension. This was not due to stiffening, structural remodelling or increased sensitivity to vasoconstrictor stimuli in the systemic arterial tree. It rather resulted from a regionally selective and specific attenuation of NO-mediated endothelium-dependent relaxation in medium-sized muscular conduit arteries via uncoupling of NOS.

Collectively, our data warrant clinical proof-of-concept trials aiming at a theragnostic [59] strategy in carefully stratified hypertensive patients based on the detection of elevated NOX5, ROS overproduction, e.g. by oxidatively modified proteins, and mechanism-based functional repair by a network pharmacology approach that inhibits NOX5 and recouples NOS. This is the first case of a molecular redefinition of the phenotypic disease definition, essential primary hypertension, and a first step towards precision medicine in a currently high number-needed-to-treat indication. This may be the case for about a fourth of all hypertensives.

The fact that NOX5 is also involved in a worse outcome in stroke [31], for which hypertension is a major risk factor [60], and correlates with atherosclerosis [61], this approach may not only lower blood pressure, but also two major consequences of hypertension, stroke and myocardial infarction.

On a broader scale, our present three-fold interactome-based approach for disease module discovery, pre-clinical and clinical validation appears to be applicable to a wide range of common or complex diseases. We here identify NOX5 as the missing link between ROS and impaired NO signalling. The full module consists of NOX5, NOS3, the different subunits of the NO receptor sGC and the phosphodiesterases, PDE5 and PDE9, as well as the cGMP dependent protein kinase, PKG1. Dysregulation of such a module may be best treated by multiple drugs targeting different protein components. In the present case, the WT mice mimic pharmacological NOX5 inhibition and the treatment with sepiapterin, NOS recoupling.

Disease module construction is a young research field at the interface of biomedicine and bioinformatics. We began with a seed gene-based approach, based on clinically validated proteins. NOX were suggested by GWAS in old [5] but not in younger patients [62] and are the only known enzyme family solely dedicated to ROS formation [63]. The NO-cGMP pathway is important for blood pressure regulation and its dysfunction a hallmark of hypertension[64]. Our approach yielded a module containing a sufficient set of NO-cGMP signalling components and, importantly, with Nox5 as sole ROS source. We confirmed our findings independently by two complementing in-silico network module detection approaches.

Endothelial microparticles are well established surrogate biomarkers associated with hypertension and its progression [65, 66]. They produce ROS, contain NOX, induce endothelial dysfunction and impair endothelium-dependent relaxation [67]. In human endothelial cells, angiotensin II, the target of clinically used angiotensin type 1 receptor blockers and angiotensin converting enzyme inhibitors, and the pro-hypertensive autacoid, endothelin-1, increase NOX5 expression (gene and protein) and activity [68]. In addition to its physiological vascular expression in endothelial cells, NOX5 is also increased (gene, protein, and activity) to higher levels in human renal proximal tubule cells of hypertensive patients [69], which may contribute to the observed correlation of NOX5, blood pressure and microalbuminuria. Induction of NOX5 in smooth muscle cells does not cause hypertension per se, but correlates with advanced atherosclerotic lesions and diseased coronary arteries show high NOX5 expression and activity [61]. Hypertension is rather an umbrella term for different blood pressure-elevating mechanisms. Some of these may be related to worse clinical outcome, some not. NOX5-dependent hypertension, however, appears to be disease-relevant as this molecular mechanism also leads to or aggravates hypertension-associated clinical outcomes, stroke [31], myocardial infarction [70] and renal failure [69, 71].

GWAS had delivered two NOX candidate genes, Nox4 and Nox5. Knocking out Nox4 is without a blood pressure phenotype [9, 72]; in many models, Nox4 was rather vasoprotective [10, 73, 74]. The enzymatic product of NOX4, $H_2O_2$, activates NOS [75] and is an alternative endothelium-derived relaxing factor in its own right [76-78]. This left Nox5 as candidate gene, which was confirmed by first neighbour analysis linked to NO-cGMP signalling. Unlike NOX4, NOX5 produces superoxide which can uncouple endothelial NO synthase in hypertension by oxidation of H4Bip [79, 80] in a sepiapterin-reversible manner [81]. The mechanistic validation of this role of NOX5 in hypertension was performed in a pre-clinical mouse KI model expressing NOX5, not present in the mouse genome, in the physiological cell type, endothelial cells where NOX5 is important for endothelial migration and angiogenesis [82]. In mice expressing NOX5 non-physiologically in smooth muscle cells, blood pressure is normal and angiotensin II-induced pressure effects are not augmented [14]. Of particular interest is the regionally selective effect of NOX5, which was reminiscent of the vascular heterogeneity in age-related endothelial dysfunction [83, 84]. It was present in muscular femoral conduit arteries but not in the small resistance-sized saphenous arteries of the KI mice and could, thus, selectively result in systolic hypertension with accompanying elevation of arterial pulse pressure. This effect was not reversed in our ex vivo experiments by antioxidants, presumably because NOS uncoupling was already established chronically in vivo by NOX5-derived superoxide. Preclinically, sepiapterin or H4Bip lower elevated blood pressure induced by NOS uncoupling [85, 86].

With respect to the clinical dimension of our findings, our observation that plasma ADMA levels were elevated in hypertensive patients speaks in favour of NOS uncoupling [29, 30]; yet a similar mechanistic link to NOX5 as we obtained pre-clinically in NOX5 KI mice would require the ex-vivo analysis of isolated human blood vessels or an interventional trial with sepiapterin. Indeed, sepiapterin analogues, i.e. folic acid and H4Bip, are clinically effective to reduce elevated blood pressure by improving endothelial function [88, 89]. Folic acid, either alone [90] or in combination with anti-hypertensives [91, 92], reduces the risk of cardiovascular and cerebrovascular events in hypertensive patients.

Overall, our findings using in-silico network approaches as well as further clinical and preclinical validation explain the long-observed correlation between oxidative stress, endothelial dysfunction and systolic hypertension. Humanized endothelial cell NOX5 KI mice represent the first mechanism-based animal model of human age-related hypertension and endothelial dysfunction. Therapeutically, NOX5 inhibition and NOS recoupling, ideally in combination with mechanistic biomarker stratification, e.g. based on endothelial microparticle liquid biopsies, represents a first-in-class mechanism-based approach for curative antihypertensive therapy obviating the need for symptomatic vasodilators.

In summary, hypertension is the most important cause of death and disability in the elderly. In nine of ten cases the molecular cause, however, remained unknown until now. This group is usually referred to as primary arterial hypertension.

We herein identify the mechanism behind at least a large fraction of the primary arterial hypertension cases, which were until now considered as treatment-resistant hypertension.

We identified this mechanism to involve impaired endothelium-dependent vasodilation through reactive oxygen (ROS) species. We found that ROS forming Nox genes associate with hypertension and we herein identify Nox5, not present in rodents, as sole neighbour to human vasodilatory endothelial nitric oxide (NO) signalling.

We found that in hypertensive subjects, endothelial microparticles contained higher levels of NOX5 with a bimodal distribution correlating with disease severity.

It appeared that the subjects with a high level of circulating NOX5 levels could effectively be treated with NOX5 inhibitors or with a compound selected from the group consisting of sepiapterin, L-citrulline, L-arginine, tetrahydrobiopterin and folic acid. An example of a suitable NOX5 inhibitor is ML090. Further examples of suitable NOX5 inhibitors are for example perphenazine, ML171, GKT-831 and VAS2870.

We found that mice expressing human NOX5 in endothelial cells, developed upon aging, severe systolic hypertension and impaired endothelium-dependent vasodilation due to uncoupled NO synthase. We conclude that NOX5-induced uncoupling of endothelial NO synthase is a causal mechanism and theragnostic target of an age-related hypertension endotype. We conclude that Nox5 knock-in mice represent the first mechanism-based animal model of hypertension.

In one embodiment, the invention therefore relates to a novel method for diagnosing essential arterial hypertension in a subject wherein the level of NADPH oxidase 5 (NOX5) is determined in a fluid or tissue sample from the subject, and wherein it is concluded that the subject has essential arterial hypertension if the level of NOX5 is above a predetermined threshold level. This method identifies the subjects with a disease entity that was previously called treatment-resistant hypertension. Those cases may now effectively be treated with NOX5 inhibitors or with compounds selected from the group consisting of sepiapterin, L-citrulline, L-arginine, tetrahydrobiopterin and folic acid. Those cases may now effectively be treated with NOX5 inhibitor setanaxib (2-(2-Chlorophenyl)-4-[3-(di-methylamino)phenyl]-5-methyl-1H-pyrazolo[4,3-c]pyridine-3,6-dione), ML171, VAS2870, perphenazine or ML090

(5,12-dihydroquinoxalino(2,3-B)quinoxaline), with molecular structure (I):

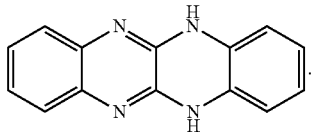

Structure (I)

In one embodiment, the invention therefore relates to a novel method for diagnosing a hypertension endotype in a subject wherein the level of NOX5 is determined in a fluid or tissue sample from the subject, preferably plasma sample, and wherein it is concluded that the subject has the hypertension endotype if the level of NOX5 is above a predetermined threshold level. The threshold level can be defined as the amount of NOX5 protein (enzyme) per volume, such as pg NOX5 per ml plasma of the hypertension endotype patient. The threshold level can also be defined as the NOX5 enzyme activity per volume, such as I.U. enzyme activity per ml plasma of the patient suffering from the endotype. This method identifies the subjects with a disease entity (endotype) that was previously a disease entity generally called treatment-resistant hypertension. Those cases of resistant hypertension patients suffering from the endotype as now defined by the inventors may now effectively be treated with NOX5 inhibitors or with compounds selected from the group consisting of sepiapterin, L-citrulline, L-arginine, tetrahydrobiopterin and folic acid. Those cases may now effectively be treated with NOX5 inhibitor setanaxib (2-(2-Chlorophenyl)-4-[3-(di-methylamino)phenyl]-5-methyl-1H-pyrazolo[4,3-c]pyridine-3,6-dione), ML171, VAS2870, perphenazine or ML090 (5,12-dihydroquinoxalino(2,3-B)quinoxaline), with molecular structure (I):

Structure (I)

Further NOX5 inhibitors suitable for inhibiting NOX5 in the patients suffering from the NOX5-dependent hypertension are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene.

An aspect of the invention relates to a method for detection of a hypertension endotype (NOX5-dependent hypertension) in a human patient suffering from essential arterial hypertension, wherein said endotype is defined by an increased level of circulating NADPH oxidase 5 protein (NOX5) compared to the level of circulating NOX5 in a human patient not suffering from hypertension, the method comprising the steps of:
(a) obtaining a fluid sample from the human patient who suffers from essential arterial hypertension, selected from the group comprising plasma, blood and serum, wherein the fluid sample comprises circulating endothelial microparticles;
(b) isolating the endothelial microparticles from the fluid sample provided in step (a); and
(c) measuring NOX5 in the endothelial microparticles of step (b) using a protein detection assay and determining the concentration of NOX5 in the fluid sample in pg NOX5 per ml fluid sample,
wherein it is concluded that the human patient suffers from the hypertension endotype (NOX5-dependent hypertension) if the concentration of NOX5 as determined in step (c) is at least 160 pg NOX5 per ml of the fluid sample. The threshold level can also be defined as the NOX5 enzyme activity per volume, such as I.U. enzyme activity per ml plasma of the patient suffering from the endotype.

Preferred is the method for detection of the hypertension endotype (NOX5-dependent hypertension) in a human patient suffering from essential arterial hypertension, wherein the fluid sample is a plasma sample.

The invention also relates to a method for detection of a hypertension endotype (NOX5-dependent hypertension) in a human patient suffering from essential arterial hypertension, wherein said endotype is defined by an increased level of circulating NADPH oxidase 5 protein (NOX5) compared to the level of circulating NOX5 in a human subject not suffering from hypertension, the method comprising the steps of:
(a) obtaining a plasma sample from the human patient who suffers from essential arterial hypertension; and
(b) measuring NOX5 in the plasma sample of step (a) using a protein detection assay and determining the concentration of NOX5 in the plasma sample in pg NOX5 per ml plasma,
wherein it is concluded that the human patient suffers from the hypertension endotype (NOX5-dependent hypertension) if the concentration of NOX5 as determined in step (b) is at least 160 pg NOX5 per ml of the plasma sample.

Particularly, in the method for detection of the hypertension endotype (NOX5-dependent hypertension) in a human patient suffering from essential arterial hypertension, the human patient suffers from hypertension as defined as a systolic blood pressure of at least 140 mmHg, a diastolic blood pressure of at least 90 mmHg, or use of an antihypertensive drug. More in particular, in the method for detection of the hypertension endotype in a human patient suffering from essential arterial hypertension, the human patient suffers from hypertension as defined as a systolic blood pressure of at least 135 mmHg, a diastolic blood pressure of at least 85 mmHg, or use of an antihypertensive drug, in the absence of diabetes and in the absence of other risk factors for myocardial infarction and stroke. Even more in particular, in the method for detection of the hypertension endotype in a human patient suffering from essential arterial hypertension, the human patient suffers from resistant hypertension according to the definition as provided by the American Heart Association [104] as: above-goal elevated blood pressure (BP) in a patient despite the concurrent use of three anti-hypertensive drug classes, commonly including a long-acting calcium channel blocker, a blocker of the renin-angiotensin system (angiotensin-converting enzyme inhibitor or angiotensin receptor blocker), and a diuretic. The antihypertensive drugs should be administered at maximum or maximally tolerated daily doses. RH also includes patients whose BP achieves target values on more than four anti-hypertensive medications. The diagnosis of RH requires assurance of anti-hypertensive medication adherence and exclusion of the "white-coat effect" (office BP above goal but out-of-office BP at or below target).

For the method for detection of the hypertension endotype (NOX5-dependent hypertension) in a human patient suffering from essential arterial hypertension, the human patient does not have a history or clinical evidence of any of: angina, myocardial infarction, congestive heart failure, peripheral vascular disease, inflammatory disease and any disease predisposing to vasculitis, and wherein the human patient does not have stage 4 or stage 5 chronic kidney disease.

An embodiment is the method for the detection of a hypertension endotype (NOX5-dependent hypertension) in a human patient suffering from essential arterial hypertension, wherein in step (c) the protein detection assay is an enzyme-linked immunosorbent assay.

An aspect of the invention relates to a method for the detection of a hypertension endotype (NOX5-dependent hypertension) in a human patient suffering from essential arterial hypertension, wherein said endotype is hypertension characterized by being
   accompanied by renal vascular leakage as established by the occurrence of microalbuminuria; or
   associated with the risk for developing renal vascular leakage apparent as development of microalbuminuria,
the method comprising the steps of:
   (a) obtaining a fluid sample from the human patient who suffers from essential arterial hypertension, selected from the group comprising plasma, blood and serum, wherein the fluid sample comprises circulating endothelial microparticles;
   (b) isolating the endothelial microparticles from the fluid sample provided in step (a); and
   (c) measuring NADPH oxidase 5 protein (NOX5) in the endothelial microparticles of step (b) using a protein detection assay and determining the concentration of NOX5 in the fluid sample in pg NOX5 per ml fluid sample,
wherein it is concluded that the human patient has the hypertension endotype (NOX5-dependent hypertension) if the concentration of NOX5 is at least 160 pg NOX5 per ml of the fluid sample. The threshold level can also be defined as the NOX5 enzyme activity per volume, such as I.U. enzyme activity per ml plasma of the patient suffering from the endotype.

For the method for the detection of a hypertension endotype (NOX5-dependent hypertension) in a human patient suffering from essential arterial hypertension, the human patient typically has a systolic arterial blood pressure of at least 140 mmHg and a diastolic arterial blood pressure of at least 90 mmHg at two days. More in particular, for the method for the detection of a hypertension endotype (NOX5-dependent hypertension) in a human patient suffering from essential arterial hypertension, the human patient typically has a systolic arterial blood pressure of at least 135 mmHg and a diastolic arterial blood pressure of at least 85 mmHg, in the absence of diabetes and in the absence of other risk factors for myocardial infarction and stroke. Even more in particular, the method is for the detection of the hypertension endotype (NOX5-dependent hypertension) in patients suffering from resistant hypertension. The resistant hypertension (RH) can be defined according to the definition as provided by the American Heart Association [104] as: above-goal elevated blood pressure (BP) in a patient despite the concurrent use of three anti-hypertensive drug classes, commonly including a long-acting calcium channel blocker, a blocker of the renin-angiotensin system (angiotensin-converting enzyme inhibitor or angiotensin receptor blocker), and a diuretic. The antihypertensive drugs should be administered at maximum or maximally tolerated daily doses. RH also includes patients whose BP achieves target values on more than four anti-hypertensive medications. The diagnosis of RH requires assurance of anti-hypertensive medication adherence and exclusion of the "white-coat effect" (office BP above goal but out-of-office BP at or below target).

An embodiment is the method for the detection of al hypertension endotype (NOX5-dependent hypertension) in a human patient suffering from essential arterial hypertension, wherein in step (a) the fluid sample is a plasma sample.

An embodiment is the method for the detection of a hypertension endotype (NOX5-dependent hypertension) in a human patient suffering from essential arterial hypertension, wherein in step (c) the protein detection assay is an enzyme-linked immunosorbent assay.

An aspect of the invention relates to a method for diagnosing occurrence of a hypertension endotype (NOX5-dependent hypertension) in a human patient suffering from essential arterial hypertension, wherein said endotype is hypertension characterized by being
   accompanied by renal vascular leakage as established by the occurrence of micro-albuminuria; or
   associated with the risk for developing renal vascular leakage apparent as development of micro-albuminuria,
the method comprising the steps of:
   (a) obtaining a fluid sample from the human patient who suffers from essential arterial hypertension, selected from the group comprising plasma, blood and serum, wherein the fluid sample comprises endothelial microparticles;
   (b) isolating the endothelial microparticles from the fluid sample provided in step (a); and
   (c) measuring NADPH oxidase 5 protein (NOX5) in the endothelial microparticles of step (b) using a protein detection assay and determining the concentration of NOX5 in the fluid sample in pg NOX5 per ml fluid sample,
wherein it is concluded that the human patient has the hypertension endotype (NOX5-dependent hypertension) if the concentration of NOX5 is at least 160 pg NOX5 per ml of the fluid sample. The threshold level can also be defined as the NOX5 enzyme activity per volume, such as I.U. enzyme activity per ml plasma of the patient suffering from the endotype (NOX5-dependent hypertension).

Typically, the endothelial microparticles are circulating endothelial microparticles.

An aspect of the invention relates to a method of diagnosing nicotinamide adenine dinucleotide phosphate (NAPDH) oxidase 5 (NOX5)-dependent hypertension in a patient by testing for the presence of an NOX5 concentration of at least 160 pg per ml in a plasma sample obtained from the patient who suffers from essential arterial hypertension. The threshold level can also be defined as the NOX5 enzyme activity per volume, such as I.U. enzyme activity per ml plasma of the patient suffering from the endotype.

An aspect of the invention relates to a method of diagnosing NOX5-dependent hypertension in a patient, comprising determining the level of NOX5 in a fluid or tissue sample from the patient, and wherein it is concluded that the patient has NOX5-dependent hypertension if the level of NOX5 is above 160 pg per ml. The threshold level can also be defined as the NOX5 enzyme activity per volume, such as I.U. enzyme activity per ml plasma of the patient suffering from the endotype (NOX5-dependent hypertension).

An embodiment is the method of diagnosing NOX5-dependent hypertension in a patient, wherein the fluid or tissue sample is a plasma sample.

An embodiment is the method of diagnosing NOX5-dependent hypertension in a patient comprising the steps of:
(a) isolating endothelial microparticles from the plasma sample; and
(b) measuring NOX5 in the endothelial microparticles of step (a) using a protein detection assay and determining the concentration of NOX5 in the plasma sample in pg NOX5 per ml plasma sample, wherein the human patient is diagnosed as suffering from NOX5-dependent hypertension if the concentration of NOX5 as determined in step (b) is at least 160 pg NOX5 per ml of the plasma sample. The threshold level can also be defined as the NOX5 enzyme activity per volume, such as I.U. enzyme activity per ml plasma of the patient suffering from the endotype.

Preferably, the endothelial microparticles are circulating endothelial microparticles.

An aspect of the invention relates to a method for diagnosing occurrence of a hypertension endotype (NOX5-dependent hypertension) in a human patient suffering from essential arterial hypertension, wherein said endotype is defined by an increased level of circulating NADPH oxidase 5 protein (NOX5) compared to the level of circulating NOX5 in a human patient not suffering from hypertension, the method comprising the steps of:
(a) obtaining a fluid sample from the human patient who suffers from essential arterial hypertension, selected from the group comprising plasma, blood and serum, wherein the fluid sample comprises endothelial microparticles;
(b) isolating the endothelial microparticles from the fluid sample provided in step (a); and
(c) measuring NOX5 in the endothelial microparticles of step (b) using a protein detection assay and determining the concentration of NOX5 in the fluid sample in pg NOX5 per ml fluid sample, wherein it is concluded that the human patient suffers from the hypertension endotype (NOX5-dependent hypertension) if the concentration of NOX5 as determined in step (c) is at least 160 pg NOX5 per ml of the fluid sample. The threshold level can also be defined as the NOX5 enzyme activity per volume, such as I.U. enzyme activity per ml plasma of the patient suffering from the endotype.

Typically, the endothelial microparticles are circulating endothelial microparticles.

An embodiment is the method for diagnosing occurrence of a hypertension endotype (NOX5-dependent hypertension) in a human patient suffering from essential arterial hypertension, wherein the fluid sample obtained from the human patient in step (a) is a plasma sample.

An embodiment is the method for diagnosing occurrence of a hypertension endotype (NOX5-dependent hypertension) in a human patient suffering from essential arterial hypertension, wherein the human patient suffers from hypertension as defined as a systolic blood pressure of at least 140 mmHg, a diastolic blood pressure of at least 90 mmHg, or use of an antihypertensive drug. An embodiment is the method for diagnosing occurrence of a hypertension endotype (NOX5-dependent hypertension) in a human patient suffering from essential arterial hypertension, wherein the human patient suffers from hypertension as defined as a systolic blood pressure of at least 135 mmHg, a diastolic blood pressure of at least 85 mmHg, or use of an antihypertensive drug.

An embodiment is the method for diagnosing occurrence of a hypertension endotype (NOX5-dependent hypertension) in a human patient suffering from essential arterial hypertension, wherein the human patient does not have a history or clinical evidence of any of: angina, myocardial infarction, congestive heart failure, peripheral vascular disease, inflammatory disease and any disease predisposing to vasculitis, and wherein the human patient does not have stage 4 or stage 5 chronic kidney disease.

An aspect of the invention relates to a method for treating NADPH oxidase 5 (NOX5)-dependent hypertension comprising administering one or more of the compounds sepiapterin, folic acid, L-citrulline, L-arginine and tetrahydrobiopterin to a human patient suffering from essential arterial hypertension, wherein the human patient has an NOX5 plasma concentration of at least 160 pg NOX5 per ml plasma.

An aspect of the invention relates to a method for treating NOX5-dependent hypertension comprising administering sepiapterin to a human patient suffering from essential arterial hypertension, wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype.

Also preferred is the method for treating NOX5-dependent hypertension, wherein the human patient has moderately increased albuminuria defined as albumin excretion rate of 20-200 mg per minute.

For some embodiments, for the method for treating NOX5-dependent hypertension, the human patient is diagnosed as suffering from NOX5-dependent hypertension with the method of detection of NOX5-dependent hypertension or the method of diagnosing of NOX5-dependent hypertension as herein described.

An embodiment is the method for treating NOX5-dependent hypertension, wherein the human patient is at least 53 years of age.

An embodiment is the method for treating NOX5-dependent hypertension, wherein the human patient is at least 57 years of age. Typically, the patient may also suffer from micro-albuminuria.

An embodiment is the method for treating NOX5-dependent hypertension, wherein the human patient has a plasma concentration of asymmetric dimethylarginine (ADMA) that is higher compared to the average plasma concentration of asymmetric dimethylarginine of a group of healthy human patients.

An embodiment is the method for treating NOX5-dependent hypertension, wherein the human patient has a plasma concentration of asymmetric dimethylarginine of at least 0.53 micromol per liter, preferably at least 0.58 micromol per liter, more preferably at least 0.63 micromol per liter.

An embodiment is the method for treating NOX5-dependent hypertension, wherein the human patient suffers from hypertension as defined as a systolic blood pressure of at least 140 mmHg, a diastolic blood pressure of at least 90 mmHg, or use of an antihypertensive drug. An embodiment is the method for treating NOX5-dependent hypertension, wherein the human patient suffers from hypertension as defined as a systolic blood pressure of at least 135 mmHg, a diastolic blood pressure of at least 85 mmHg, or use of an antihypertensive drug.

In embodiments, in the method for treating NOX5-dependent hypertension, the human patient does not have a history or clinical evidence of any of: angina, myocardial infarction, congestive heart failure, peripheral vascular disease, inflammatory disease and any disease predisposing to vasculitis, and wherein the human patient does not have stage 4 or stage 5 chronic kidney disease.

An aspect of the invention relates to a method for treating NOX5-dependent hypertension, the method for treating comprising administering an NOX5 inhibitor to a human patient suffering from essential arterial hypertension. Typically, the method comprises administering an NOX5 inhibitor to a human patient suffering from essential arterial hypertension, wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype.

An aspect of the invention relates to a method for treating NOX5-dependent hypertension, the method for treating comprising administering the NOX5 inhibitor 5,12-dihydroquinoxalino(2,3-B)quinoxaline (ML090) to a human patient suffering from essential arterial hypertension. Typically, the method comprises administering ML090 to a human patient suffering from essential arterial hypertension, wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

The invention further relates to a compound selected from the group consisting of sepiapterin, L-citrulline, L-arginine, tetrahydrobiopterin, folic acid and a NOX5 inhibitor, in particular a NOX5 inhibitor based on quinoxaline such as NOX5 inhibitor 5,12-dihydroquinoxalino(2,3-B)quinoxaline (ML090), for use in the treatment of a subject with essential arterial hypertension, in particular with NOX5-dependent hypertension. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient has moderately increased albuminuria defined as albumin excretion rate of 20-200 mg per minute.

An embodiment is the method for treating NOX5-dependent hypertension comprising administering an NOX5 inhibitor, such as a NOX5 inhibitor based on quinoxaline such as ML090, wherein the human patient is diagnosed as suffering from NOX5-dependent hypertension with the method of detecting NOX5-dependent hypertension, or with the method of diagnosing NOX5-dependent hypertension. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient is at least 53 years of age.

An embodiment is the method for treating NOX5-dependent hypertension comprising administering an NOX5 inhibitor, such as ML090, wherein the human patient is at least 57 years of age. In embodiments, the patient has micro-albuminuria. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient has a plasma concentration of asymmetric dimethylarginine that is higher compared to the average plasma concentration of asymmetric dimethylarginine of a group of healthy human patients. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient has a plasma concentration of asymmetric dimethylarginine of at least 0.53 micromol per liter, preferably at least 0.58 micromol per liter, more preferably at least 0.63 micromol per liter. Another suitable NOX5 inhibitor is setanaxib (2-(2-Chlorophenyl)-4-[3-(di-methylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient suffers from hypertension as defined as a systolic blood pressure of at least 140 mmHg, a diastolic blood pressure of at least 90 mmHg, or use of an antihypertensive drug.

An embodiment is the method for treating NOX5-dependent hypertension comprising administering an NOX5 inhibitor, such as ML090, wherein the human patient suffers from hypertension as defined as a systolic blood pressure of at least 135 mmHg, a diastolic blood pressure of at least 85 mmHg, or use of an antihypertensive drug. Another suitable NOX5 inhibitor is setanaxib (2-(2-Chlorophenyl)-4-[3-(dimethylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An embodiment is the method for treating NOX5-dependent hypertension comprising administering an NOX5 inhibitor, such as a NOX5 inhibitor based on quinoxaline such as ML090, wherein the human patient does not have a history or clinical evidence of any of: angina, myocardial infarction, congestive heart failure, peripheral vascular disease, inflammatory disease and any disease predisposing to vasculitis, and wherein the human patient does not have stage 4 or stage 5 chronic kidney disease. Another suitable NOX5 inhibitor is setanaxib (2-(2-Chlorophenyl)-4-[3-(dimethylamino)phenyl]-5-methyl-1H-pyrazolo[4,3-c]pyridine-3,6-dione). Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870.

An aspect of the invention relates to administering an effective amount of one or more of sepiapterin, folic acid, L-citrulline, L-arginine and tetrahydrobiopterin to a human patient to treat NADPH oxidase 5 (NOX5)-dependent hypertension.

An embodiment is the administering of an effective amount of one or more sepiapterin, folic acid, L-citrulline, L-arginine and tetrahydrobiopterin to a human patient to treat NOX5-dependent hypertension, wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An embodiment is the administering of an effective amount of sepiapterin to a human patient to treat NOX5-dependent hypertension, preferably wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An embodiment is the administering of an effective amount of one or more sepiapterin, folic acid, L-citrulline, L-arginine and tetrahydrobiopterin to a human patient to treat NOX5-dependent hypertension, wherein said human patient is diagnosed as suffering from NOX5-dependent hypertension with the method of the detection of a hypertension endotype (NOX5-dependent hypertension) in a human patient suffering from essential arterial hypertension.

An aspect of the invention relates to administering an effective amount of an NOX5 inhibitor to a human patient to treat NADPH oxidase 5 (NOX5)-dependent hypertension.

An aspect of the invention relates to administering an effective amount of a NOX5 inhibitor based on a quinoxaline to a human patient to treat NADPH oxidase 5 (NOX5)-dependent hypertension.

An aspect of the invention relates to administering an effective amount of NOX5 inhibitor 5,12-dihydroquinoxalino(2,3-B)quinoxaline (ML090) to a human patient to treat NADPH oxidase 5 (NOX5)-dependent hypertension.

An aspect of the invention relates to administering an effective amount of NOX5 inhibitor setanaxib (2-(2-Chlorophenyl)-4-[3-(di-methylamino)phenyl]-5-methyl-1H-pyrazolo[4,3-c]pyridine-3,6-dione) to a human patient to treat NOX5-dependent hypertension. In addition, NOX5 inhibitors suitable for inhibiting NOX5 in the patients suffering from the NOX5-dependent hypertension are for example perphenazine, ML171 and VAS2870.

An embodiment is the administering of an effective amount of an NOX5 inhibitor such as a NOX5 inhibitor based on quinoxaline such as 5,12-dihydroquinoxalino(2,3-B)quinoxaline or setanaxib (2-(2-Chlorophenyl)-4-[3-(di-methylamino)phenyl]-5-methyl-1H-pyrazolo[4,3-c]pyridine-3,6-dione) to a human patient to treat NOX5-dependent hypertension, wherein the human patient has an NOX5 plasma concentration of at least 160 pg NOX5 per ml plasma. Further NOX5 inhibitors suitable for inhibiting NOX5 in the patients suffering from the hypertension endotype (NOX5-dependent hypertension) are for example anti-human NOX5 antibodies, or any binding domain(s) thereof or any binding fragment(s) thereof endowed with the ability to inhibit NOX5 enzyme activity, or an siRNA suitable for gene silencing of the human Nox5 gene. In addition, NOX5 inhibitors suitable for inhibiting NOX5 in the patients suffering from the NOX5-dependent hypertension are for example perphenazine, ML171 and VAS2870. The threshold level can also be defined as the NOX5 enzyme activity per volume, such as I.U. enzyme activity per ml plasma of the patient suffering from the endotype (NOX5-dependent hypertension).

An embodiment is the administering of an effective amount of an NOX5 inhibitor or a NOX5 inhibitor based on quinoxaline such as 5,12-dihydroquinoxalino(2,3-B)quinoxaline or setanaxib (2-(2-Chlorophenyl)-4-[3-(di-methylamino)phenyl]-5-methyl-1H-pyrazolo[4,3-c]pyridine-3,6-dione) to a human patient to treat NOX5-dependent hypertension, wherein said human patient is diagnosed as suffering from NOX5-dependent hypertension with the method for diagnosing occurrence of a hypertension endotype (NOX5-dependent hypertension) in a human patient suffering from essential arterial hypertension. In addition, NOX5 inhibitors suitable for inhibiting NOX5 in the patients suffering from the NOX5-dependent hypertension are for example perphenazine, ML171 and VAS2870.

An aspect of the invention relates to a method for treating NADPH oxidase 5 (NOX5)-dependent hypertension comprising administering an effective amount one or more of the compounds sepiapterin, L-arginine, L-citrulline, folic acid and tetrahydrobiopterin to a human patient suffering from essential arterial hypertension, wherein the human patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An aspect of the invention relates to a method for treating NOX5-dependent hypertension comprising administering a compound selected from sepiapterin, folic acid, L-citrulline, L-arginine and tetrahydrobiopterin to a patient with essential arterial hypertension, characterised in that the patient with essential arterial hypertension has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An embodiment is the method for treating NOX5-dependent hypertension, wherein the essential arterial hypertension is NOX5-dependent hypertension.

An aspect of the invention relates to a method for treating NOX5-dependent hypertension comprising administering a compound selected from sepiapterin, folic acid, L-citrulline, L-arginine and tetrahydrobiopterin to a patient having treatment-resistant hypertension.

An embodiment is the method for treating NOX5-dependent hypertension comprising administering a compound selected from sepiapterin, folic acid, L-citrulline, L-arginine and tetrahydrobiopterin to a patient having treatment-resistant hypertension, wherein the patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An embodiment is the method for treating NOX5-dependent hypertension comprising administering a compound selected from sepiapterin, folic acid, L-citrulline, L-arginine and tetrahydrobiopterin to a patient having treatment-resistant hypertension, wherein the patient has an NOX5 plasma concentration of at least 160 pg NOX5 per ml plasma. The threshold level can also be defined as the NOX5 enzyme activity per volume, such as I.U. enzyme activity per ml plasma of the patient suffering from the endotype (NOX5-dependent hypertension).

An embodiment is the method for treating NOX5-dependent hypertension, wherein the compound is sepiapterin.

An embodiment is the method for treating NOX5-dependent hypertension, wherein the patient has moderately increased albuminuria defined as albumin excretion rate of 20-200 mg per minute.

An embodiment is the method for treating NOX5-dependent hypertension, wherein the patient is diagnosed as suffering from NOX5-dependent hypertension with the method of the detection or diagnosing of a hypertension endotype (NOX5-dependent hypertension) in a human patient suffering from essential arterial hypertension, the endotype characterized by a plasma level of NOX5 of at least 160 pg/ml. The threshold level can also be defined as the NOX5 enzyme activity per volume, such as I.U. enzyme activity per ml plasma of the patient suffering from the endotype (NOX5-dependent hypertension).

An embodiment is the method for treating NOX5-dependent hypertension, wherein the patient is at least 53 years of age.

An embodiment is the method for treating NOX5-dependent hypertension, wherein the patient is at least 57 years of age. Typically, the patient suffers from micro-albuminuria.

An embodiment is the method for treating NOX5-dependent hypertension, wherein the patient has a plasma concentration of asymmetric dimethylarginine that is higher compared to the average plasma concentration of asymmetric dimethylarginine of a group of healthy patients.

An embodiment is the method for treating NOX5-dependent hypertension, wherein the patient has a plasma concentration of asymmetric dimethylarginine of at least 0.53 micromol per liter, preferably at least 0.58 micromol per liter, more preferably at least 0.63 micromol per liter.

An embodiment is the method for treating NOX5-dependent hypertension or the method for the detection of the hypertension endotype (NOX5-dependent hypertension) characterized by a plasma level of NOX5 of at least 160 pg/ml in a human patient suffering from essential arterial hypertension, wherein the patient suffers from hypertension as defined as a systolic blood pressure of at least 140 mmHg, a diastolic blood pressure of at least 90 mmHg, or use of an antihypertensive drug. An embodiment is the method for treating NOX5-dependent hypertension or the method for the detection of the hypertension endotype (NOX5-dependent hypertension) characterized by a plasma level of NOX5 of at least 160 pg/ml in a human patient suffering from essential arterial hypertension, wherein the patient suffers from hypertension as defined as a systolic blood pressure of at least 135 mmHg, a diastolic blood pressure of at least 85 mmHg, or use of an antihypertensive drug. The threshold level can also be defined as the NOX5 enzyme activity per volume, such as I.U. enzyme activity per ml plasma of the patient suffering from the endotype (NOX5-dependent hypertension).

An embodiment is the method for treating NOX5-dependent hypertension or the method for the detection of the hypertension endotype (NOX5-dependent hypertension) characterized by a plasma level of NOX5 of at least 160 pg/ml in a human patient suffering from essential arterial hypertension, wherein the patient does not have a history or clinical evidence of any of: angina, myocardial infarction, congestive heart failure, peripheral vascular disease, inflammatory disease and any disease predisposing to vasculitis, and wherein the patient does not have stage 4 or stage 5 chronic kidney disease. The threshold level can also be defined as the NOX5 enzyme activity per volume, such as I.U. enzyme activity per ml plasma of the patient suffering from the endotype (NOX5-dependent hypertension).

An aspect of the invention relates to the use of a mouse with knocked-in human Nox5 gene to discover and develop therapeutics and methods for detection, for the use in NOX5-dependent hypertension in a patient.

An embodiment is the use of a mouse with knocked-in human Nox5 gene, wherein the mouse has an age of at least 68 weeks.

An embodiment is the use of a mouse with knocked-in human Nox5 gene, wherein the mouse is a 129/SV mouse. In particular, the mouse has a mixed genetic background, comprising 80% 129/SV. More in particular, the mouse has a mixed genetic background, consisting of 80% 129/SV and 20% C57B16.

An embodiment is the use of the mouse with knocked-in human Nox5 gene, wherein the knocked-in human Nox5 gene is regulated by promotor tie 2.

An embodiment is the use of the mouse with knocked-in human Nox5 gene, wherein human NOX5 is expressed in endothelial cells and white blood cells of the mouse.

In a further embodiment, the invention relates to a method as described above, wherein the predetermined threshold level is the level of NOX5 determined in a sample taken from a healthy subject using an identical method, the subject not having essential arterial hypertension. In an even more preferred embodiment, the threshold level is 160 pg of NOX5 per ml. In an even more preferred embodiment, the subject also has micro-albuminuria. The sample to be used in the method described herein may be a fluid or tissue sample, preferably the sample comprises vascular endothelial cells, even more preferably the sample comprises circulating endothelial microparticles.

In a further embodiment, the invention provides a method as described above wherein the level of NOX5 is determined by measuring the level of Nox5 messenger RNA.

In a further embodiment, the invention provides a method as described above, wherein the level of NOX5 is determined by measuring the level of uncoupled nitric oxide synthase (NOS).

In a further embodiment, the invention provides a method as described above, wherein the level of uncoupled NOS is determined by measuring the level of asymmetric dimethylarginine (ADMA).

In a further embodiment, the invention provides a method as described above, wherein the sample is selected from the group comprising plasma, blood and serum.

In a further embodiment, the invention provides a method as described above, wherein the sample comprises platelet rich plasma containing white blood cells.

In a further embodiment, the invention provides a method as described above, wherein the sample comprises platelet poor plasma.

The invention further relates to a compound selected from the group consisting of sepiapterin, L-citrulline, L-arginine, tetrahydrobiopterin, folic acid and a NOX5 inhibitor for use in the treatment of a subject with essential arterial hypertension.

In a further embodiment, the invention relates to a compound for use as described above wherein the subject was diagnosed with essential arterial hypertension using a method as described herein, prior to the treatment.

In a further embodiment, the invention relates to a compound for use as described above wherein the treatment comprises the administration of a compound selected from the group consisting of sepiapterin, L-citrulline, L-arginine, tetrahydrobiopterin, folic acid and a NOX5 inhibitor to the subject and wherein the compound is administered in such quantity that the level of the compound is normalized in the fluid or tissue from which the sample was taken.

In a further embodiment, the invention relates to a compound for use as described above wherein the treatment comprises a step of measuring the level of NOX5 as described herein.

In a further embodiment, the invention relates to the use of an aged NOX5 knock-in an animal model to discover and develop therapeutics and diagnostics for the use in NOX5- and uncoupled NOS-dependent essential arterial hypertension

EXAMPLES

Example 1: Study Design

Human subjects sample size was determined by G*Power software. For mice, we used a power analysis according to the formula $n=2 \times s2 \times (Za/2+Zb)2/D2$ (L. Sachs, Angewandte Statistik, Springer, 1983, Berlijn, Springer Verlag). Human subjects with history or clinical evidence of angina, myocardial infarction, congestive heart failure, peripheral vascular disease, inflammatory disease, or any disease predisposing to vasculitis were excluded. Causes of secondary hypertension were excluded by appropriate investigations. Patients with stage 4 and 5 chronic kidney disease (GFR<30 mL/min/1.73 $m^2$) were also excluded. Human samples were allocated to different group based on blood pressure and albuminuria values. Mice were allocated to experimental groups according to genotypes. Investigators were blinded to the experimental groups. Replicate experiments were successful. All experiments were reproduced at least three times with independent biological samples.

Example 2: In-Silico Methods

We extracted a molecular subnetwork from experimentally validated protein-protein interactions from the IID [19] database (interactome) using NOX family members and nitric oxide-cyclic GMP related proteins as seed nodes. This set of seeds comprises NOX1, NOX3, NOX4, NOX5, NOS1, NOS3, GUCYA1, GUCYA2, GUCYB1, PDE5A, PDE9A and PRKG1. We obtained the subnetwork induced by all first neighbours of the seed genes from the interactome. The induced subnetwork was then pruned according to the subnetwork-participation-degree (SPD), defined as the degree of the node (protein) inside the subnetwork normalized by the degree of the node in the full interactome. The SPD quantifies how enriched the interactions of a given protein are in a given subnetwork. This way, we emerged a weighted disease module, which is represented by a set of connected components and some single nodes. We selected an SPD cut-off corresponding to 80% of the cumulative sum of the percentage of the nodes as a cut-off value in the pruning step, as this includes most module-specific interactions while excluding most non-specific nodes. The final subnetwork consisted of 56 proteins and 83 protein-protein interactions.

Moreover, we applied the two top-ranked disease network module identification methods from the Module Identification DREAM Challenge [21] to the interactome. We selected these methods from two complementary categories of methods, global and local. The main difference between these two methods is that global methods exploit the global structure information of PPI networks, while the local methods considers only local neighbour information. The global modularity optimization method (M1) of the DREAM challenge bundled in the MONET tool and the agglomerative local method (L1) from SPICi tool [23] have been selected (as best-performers in their categories) and applied to find disease modules in the interactome. Note that M1 is an ensemble approach combining multiple module detection algorithms to avoid suboptimal partitions resulting from individual algorithms [22], which notably works without any seed nodes in this tool. The agglomerative L1 method clusters the network greedily, starting from automatically selected local seeds with high weighted degree. This algorithm improves local density of modules in the neighboring region of seed nodes.

Example 3: Human Study Participants

We designed the current study on the basis of a previous study in which we had enrolled consecutive outpatients with essential primary hypertension and a baseline estimated GFR≥30 mL/min/1.73 m² at Taipei Veterans General Hospital between April 2008 and December 2008 [93, 94]. Hypertension was defined as a systolic blood pressure 140 mmHg, a diastolic blood pressure ≥90 mmHg, or use of antihypertensive drugs. Subjects with history or clinical evidence of angina, myocardial infarction, congestive heart failure, peripheral vascular disease, inflammatory disease, or any disease predisposing to vasculitis were excluded. Causes of secondary hypertension were excluded by appropriate investigations. Patients with stage 4 and 5 chronic kidney disease (GFR<30 mL/min/1.73 m²) were also excluded. Medical history, including cardiovascular risk factors, previous and present cardiovascular events, and current medication regimen, was obtained during a personal interview and from medical files. Weight, height, and waist circumference were measured and body mass index (BMI) was calculated. Brachial blood pressure was measured by a physician with a mercury sphygmomanometer after patients sat for 15 minutes or longer. The average of 3 measurements was used for the analysis.

Example 4: Blood and Urine Measurements

Venous blood samples were collected from all patients after 8 hours of overnight fasting for measurement. The blood samples were centrifuged at 3000 rpm for 10 minutes immediately after collection, and the plasma samples were kept frozen at −70° C. until analysis. Each standard and plasma sample was analyzed twice, and the mean value was used in all subsequent analyses. The plasma high-sensitivity C-reactive protein (hs-CRP) level was determined using a latex-enhanced immuno-nephelometric assay (Dade Behring, Marburg, Germany). Plasma N-terminal pro b-type natriuretic peptide (NT-proBNP) was determined by a sandwich immunoassay (EIMA) with two antibodies (Cortez Diagnostics, Calabasas, Calif., USA). Plasma ADMA levels were measured by ADMA Fast ELISA kit (DLD Diagnostika GMBH, Hamburg, Germany). Overnight urine samples were obtained for measurement of the albumin excretion rate. Normo-albuminuria was defined as albumin excretion rate of less than 20 mg/min, moderately increased albuminuria (previously known as micro-albuminuria) was defined as albumin excretion rate of 20-200 mg/min, and severely increased albuminuria (previously known as macro-albuminuria) was defined as albumin excretion rate more than 200 mg/min.

Example 5: Endothelial Microparticles Extraction and Measurement of NOX5

CD144+ microparticles were isolated as described with modifications [95, 96]. Briefly, Dynabeads G (Invitrogen, Carlsbad, Calif.) were washed with PBS containing 0.1% BSA and then reconstituted with PBS. Anti-CD144 antibody (Santa Cruz Biotechnology, Dallas, Tex.) which specifically targets endothelial cells was mixed with prewashed Dynabeads G for 2 hours and then incubated with plasma samples at 1:200 dilution overnight at 4° C. After precipitation, Dynabeads G were washed with PBS and 1% Tween-20 three times. The purity of CD144+ MPs, determined by FACS analysis, was 70%±5.6%. With the use of FITC-conjugated beads as size references, the size of such particles was assessed to be <0.5 μm in diameter. Human NADPH oxidase 5 (NOX5) levels were measured using commercially available enzyme-linked immunosorbent assay (ELISA, Cusabio Technology LLC, Houston, Tex.) kit according to the manufacturer's instructions. Samples were stored at −70° C. from date of collection in 2008 until testing for NOX5 in 2014 (totally 50 samples were available). The intra-assay and inter-assay variation coefficients of the tests were <8% and <10%, respectively.

Example 6: Animals

Mice naturally do not express the NOX5 gene, therefore, we have generated and validated humanized NOX5 Knock-in (KI) mice as previously described [31]. The mice were 80% 129/SV/20% C571316 mice, as described [31]. Briefly, the model was developed using the hypoxanthine phosphoribosyl-transferase (Hprt) targeted transgenic approach under the control of the Tie2 promoter. Therefore, our NOX5 KI mice express the NOX5 in endothelial and white blood cells which mimic the physiological human expression of NOX5. Expression of NOX5 in the KI mice tissues was previously validated by quantitative real-time PCR and compared to Wild Type (WT) mice [31]. Age- and gender-matched groups of male and female mice (9-15 weeks old, n=19-20) and (68-87 weeks old, n=31-33) were used. All mice were allowed free access to water and food in a temperature-regulated room (22° C.) and placed in a 12 h light-dark cycle.

Example 7: Blood Pressure Recording (Telemetry)

NOX5 KI and WT Mice were anaesthetized with isoflurane (induction, 3-4%; maintenance, 1.5-2.5%) and echocardiography (ultrasound) was performed (FIG. 13). To implant the telemetry transmitters, 5 days after the ultrasound, mice were anaesthetized with the same protocol and preoperative analgesia was done by subcutaneous injection of 0.05 mg/kg buprenorphine repeated every 12 hours. Each mouse was placed on a heating pad (UNO temperature control unit, UNO Roestvaststaal BV) and body temperature was monitored using a rectal probe and maintained at 37.0° C. using a feedback-controlled infrared light. An incision in the skin overlying the carotid artery was made. Via this incision, in the subcutaneous space of the flank a pocket was created for inserting the telemetry transmitter (TA11PA-C10; Data Sciences, Inc., St. Paul, Minn.) to monitor blood pressure, heart rate, and motor activity. The left carotid artery was dissected free and 3 ligatures (5-0, silk) were placed: at the bifurcation of the internal and external carotid to close the vessel, at the heart to temporarily close the vessel and one in between to fixate the catheter. Via a small hole cut in the artery, the catheter was introduced and advanced into the aortic arch. Then, the pocket in the flank was filled with 3 mL prewarmed saline and the transmitter was placed in the pocket. The wound was then closed using a polysorb 5-0 suture. All surgical procedures were performed under aseptic conditions. Postoperative analgesia was done by subcutaneous injection of 0.05 mg/kg buprenorphine after 6 hr. and 5 mg/kg carprofen after 24 and 48 hr. Mice were allowed to recover for 7-14 days before starting the measurement. Mice were housed individually in a quiet room. Blood pressure was measured over a 72 h period [97-99], with 10 cycles of 75 sec. per hour. Radio signals from the transmitter were continuously monitored with a fully automated data-acquisition system (Dataquest A.R.T.; Data Sciences, Inc.). Mice were sacrificed by $CO_2/O_2$ inhalation and organs were taken out for further analysis. Organ and body weights are presented in FIG. 6.

Example 8: Myograph

After mice were sacrificed, thoracic aortae, femoral and saphenous arteries were dissected free from perivascular adipose tissue and mounted in a wire myograph (DMT, Aarhus, DK). The organ chamber was filled with Krebs-Ringer bicarbonate-buffered salt solution (KRB) that was continuously aerated with 95% $O_2$/5% $CO_2$ and maintained at 37° C. Passive stretch procedure was performed to mimic the physiologically relevant internal lumen diameter as previously described [100]. Arterial contractile and relaxing responses were recorded at lumen diameters corresponding to a distending pressure of 100 mmHg in thoracic aorta and femoral artery and at 90% of this diameter in the resistance-sized saphenous artery. This is justified because diastolic arterial blood pressure did not differ significantly between the aged KI and WT mice. In view of the comparable diameter-tension relationships, these diameters did not differ significantly between the two mouse strains (FIG. 14). The diameter tension relationships were constructed according to the law of Laplace for a cylindrical tube: P=T/R (with P for transmural pressure, T for wall tension and R for the lumen radius of the tube). Consequently, wall stiffness can be determined equally by recording 1) changes in tension in response to imposed changes in radius (wire myography) or 2) changes in radius in response to changes in transmural pressure (pressure myography) [101, 102]. Here we used the former approach because it has a higher throughput than the latter. Stress-strain relationships and even better "incremental elastic (Young's) modulus" (which require additional recording of wall thickness) only come into play to discriminate between structural and material property contributions to changes in arterial stiffness. Part of the isolated thoracic aorta was studied in the absence and part in the continuous presence of 10 μM indomethacin to inhibit production of prostaglandins that can act as endothelium-derived vasoactive factors in this vessel. The vessels were tested for their contractile response to 40 mM K+, concentration-response curves of phenylephrine (0.01 to 100 μM) and endothelin-1 (1-256 nM) followed by acetylcholine (Ach) (0.01 to 100 μM), PAPA/NO (0.01-10 μM) or Bay60-2770 (0.01-10 μM)-induced relaxations. The wall tension of the vessel segment was continuously recorded with LabChart Pro (ADInstruments, Oxford, UK).

Example 9: Measurement of Superoxide Formation: DHE Staining

Superoxide was measured in femoral arteries using the florescence dye dihydroethidium (DHE) (Thermo Scientific Technology, The Netherlands). Frozen femoral arteries cryo-sections were fixated in 4% paraformaldehyde (PFA) in PBS and then incubated with 2 μM DHE for 30 minutes at 37° C. After three washing steps with PBS, slices were incubated with DAPI (Sigma-Aldrich, The Netherlands) 2 pg/ml for 10 min. Sections were washed in PBS and then mounted using a Dako Fluorescence Mounting Medium (S3023, Agilent Technologies). Immunofluorescent signals were viewed using a Leica DM13000 B fluorescence microscope. Some arteries were pre-treated with 500 μM L-NAME for 30 min at 37° C. before performing the DHE staining.

Example 10: RNA Extraction, cDNA Synthesis and Quantitative Real-Time PCR

Thoracic aortae, femoral arteries and saphenous arteries were isolated from mice and immediately submerged in RNAlater solution (Thermo Fisher Scientific). RNA was extracted using RNeasy® Micro Kit (Qiagen) according to the manufacturer's protocol. cDNA was synthesized from 1 pg total RNA in 20 μl reactions using High Capacity cDNA Reverse Transcription Kit (Thermo Fisher Scientific). After synthesis, the cDNA was stored at −20° C.

RT-qPCR was performed on CFX96TM Real-Time PCR Detection System (Bio-Rad). All reactions were performed in triplicates in a total volume of 20 μl each using TaqMan® Universal PCR Master Mix (Applied Biosystems-Life Technologies) according to manufacturer's instructions. 3 μl cDNA was used as template and pre-designed TaqMan® primers of β-actin and Nox5 were used. The specific assay ID for the primers used are shown in Supplementary Table 1. The standard PCR conditions were as follows: 10 min at 95° C., followed by 15 s at 95° C. and 1 min at 60° C., 59 repeats. The amount of mRNA was normalized to the measured expression of β-actin mRNA.

Example 11: Statistical Analysis

All human and animal data are expressed as the mean±SEM for numeric variables and as the number (percentage) for categorical variables. Comparisons of continuous variables between the two mice groups were performed by unpaired two-tailed Student's t-test and among the three human groups by one-way analysis of variance (ANOVA) followed by Tukey's multiple comparisons test (post-hoc test). Comparisons of categorical variables among the human groups were assessed by a $\chi^2$ (chi square). Comparisons between the two mice groups, in telemetry data were done by two-way repeated measures ANOVA and in myograph by ordinary two-way ANOVA, followed by Sidak's multiple comparisons test. For the subgroup analysis of the NOX5 levels in human subjects, a frequency analysis was carried out, where the bin width is calculated using Sturges' rule [103]. To assess the modality of the data, the output frequencies were fitted with a single Gaussian and sum of two Gaussian distributions, and a two-tailed F-test with null hypothesis as Gaussian and alternative hypothesis as sum of two-Gaussians was performed. Additionally, the adjusted r-squared values were compared to select the best fitting distribution for the sample. Given the bimodal nature of the sample, the area under each Gaussian distribution was calculated using the formula "Amplitude*SD/0.3989" and subsequently the proportion of NOX5 mechanotype was reported as the ratio between the two distributions. Data were analyzed using GraphPad Prism Version 8.2 (GraphPad Software Inc., San Diego, Calif.). A p-value of less than 0.05 was considered to indicate statistical significance after multiple testing correction.

REFERENCES

1. Olsen M H, Angell S Y, Asma S, Boutouyrie P, Burger D, Chirinos J A, et al. A call to action and a lifecourse strategy to address the global burden of raised blood pressure on current and future generations: the Lancet Commission on hypertension. Lancet. 2016; 388(10060): 2665-712. Epub 2016/09/28. doi: 10.1016/S0140-6736 (16)31134-5. PubMed PMID: 27671667.
2. Oparil S, Acelajado M C, Bakris G L, Berlowitz D R, Cifkova R, Dominiczak A F, et al. Hypertension. Nat Rev Dis Primers. 2018; 4:18014. Epub 2018/03/23. doi: 10.1038/nrdp.2018.14. PubMed PMID: 29565029; PubMed Central PMCID: PMCPMC6477925.
3. Ogden L G, He J, Lydick E, Whelton P K. Long-term absolute benefit of lowering blood pressure in hypertensive patients according to the JNC V I risk stratification. Hypertension. 2000; 35(2):539-43. Epub 2000/02/19. doi: 10.1161/01.hyp.35.2.539. PubMed PMID: 10679494.

4. Gryglewski R J, Palmer R M, Moncada S. Superoxide anion is involved in the breakdown of endothelium-derived vascular relaxing factor. Nature. 1986; 320 (6061):454-6. Epub 1986/04/03. doi: 10.1038/320454a0. PubMed PMID: 3007998.
5. Kraja A T, Cook J P, Warren H R, Surendran P, Liu C, Evangelou E, et al. New Blood Pressure-Associated Loci Identified in Meta-Analyses of 475 000 Individuals. Circ Cardiovasc Genet. 2017; 10(5). Epub 2017/10/17. doi: 10.1161/CIRCGENETICS.117.001778. PubMed PMID: 29030403; PubMed Central PMCID: PMCPMC5776077.
6. Yogi A, Mercure C, Touyz J, Callera G E, Montezano A C, Aranha A B, et al. Renal redox-sensitive signaling, but not blood pressure, is attenuated by Nox1 knockout in angiotensin II-dependent chronic hypertension. Hypertension. 2008; 51(2):500-6. Epub 2008/01/16. doi: 10.1161/HYPERTENSIONAHA.107.103192. PubMed PMID: 18195161.
7. Murdoch C E, Alom-Ruiz S P, Wang M, Zhang M, Walker S, Yu B, et al. Role of endothelial Nox2 NADPH oxidase in angiotensin II-induced hypertension and vasomotor dysfunction. Basic Res Cardiol. 2011; 106(4):527-38. Epub 2011/04/30. doi: 10.1007/s00395-011-0179-7. PubMed PMID: 21528437; PubMed Central PMCID: PMCPMC3105229.
8. Sag C M, Schnelle M, Zhang J, Murdoch C E, Kossmann S, Protti A, et al. Distinct Regulatory Effects of Myeloid Cell and Endothelial Cell NAPDH Oxidase 2 on Blood Pressure. Circulation. 2017; 135(22):2163-77. Epub 2017/03/17. doi: 10.1161/CIRCULATIONAHA.116.023877. PubMed PMID: 28298457; PubMed Central PMCID: PMCPMC5444427.
9. Kleinschnitz C, Grund H, Wingler K, Armitage M E, Jones E, Mittal M, et al. Post-stroke inhibition of induced NADPH oxidase type 4 prevents oxidative stress and neurodegeneration. PLoS biology. 2010; 8(9). Epub 2010/09/30. doi: 10.1371/journal.pbio.1000479. PubMed PMID: 20877715.
10. Ray R, Murdoch C E, Wang M, Santos C X, Zhang M, Alom-Ruiz S, et al. Endothelial Nox4 NADPH oxidase enhances vasodilatation and reduces blood pressure in vivo. Arterioscler Thromb Vasc Biol. 2011; 31(6):1368-76. Epub 2011/03/19. doi: 10.1161/ATVBAHA.110.219238. PubMed PMID: 21415386.
11. Holterman C E, Thibodeau J F, Towaij C, Gutsol A, Montezano A C, Parks R J, et al. Nephropathy and elevated B P in mice with podocyte-specific NADPH oxidase 5 expression. J Am Soc Nephrol. 2014; 25(4): 784-97. doi: 10.1681/ASN.2013040371. PubMed PMID: 24262797; PubMed Central PMCID: PMCPMC3968494.
12. Jha J C, Banal C, Okabe J, Gray S P, Hettige T, Chow B S M, et al. NADPH Oxidase Nox5 Accelerates Renal Injury in Diabetic Nephropathy. Diabetes. 2017; 66(10): 2691-703. Epub 2017/07/28. doi: 10.2337/db16-1585. PubMed PMID: 28747378.
13. Jha J C, Dai A, Holterman C E, Cooper M E, Touyz R M, Kennedy C R, et al. Endothelial or vascular smooth muscle cell-specific expression of human NOX5 exacerbates renal inflammation, fibrosis and albuminuria in the Akita mouse. Diabetologia. 2019; 62(9):1712-26. Epub 2019/06/22. doi: 10.1007/s00125-019-4924-z. PubMed PMID: 31222503.
14. Montezano A C, De Lucca Camargo L, Persson P, Rios F J, Harvey A P, Anagnostopoulou A, et al. NADPH Oxidase 5 Is a Pro-Contractile Nox Isoform and a Point of Cross-Talk for Calcium and Redox Signaling-Implications in Vascular Function. J Am Heart Assoc. 2018; 7(12). Epub 2018/06/17. doi: 10.1161/JAHA.118.009388. PubMed PMID: 29907654; PubMed Central PMCID: PMCPMC6220544.
15. Barabasi A L, Gulbahce N, Loscalzo J. Network medicine: a network-based approach to human disease. Nat Rev Genet. 2011; 12(1):56-68. Epub 2010/12/18. doi: 10.1038/nrg2918. PubMed PMID: 21164525; PubMed Central PMCID: PMCPMC3140052.
16. Alcaraz N, List M, Batra R, Vandin F, Ditzel H J, Baumbach J. De novo pathway-based biomarker identification. Nucleic Acids Res. 2017; 45(16):e151. Epub 2017/09/22. doi: 10.1093/nar/gkx642. PubMed PMID: 28934488; PubMed Central PMCID: PMCPMC5766193.
17. Batra R, Alcaraz N, Gitzhofer K, Pauling J, Ditzel H J, Hellmuth M, et al. On the performance of de novo pathway enrichment. NPJ Syst Biol Appl. 2017; 3:6. Epub 2017/06/27. doi: 10.1038/s41540-017-0007-2. PubMed PMID: 28649433; PubMed Central PMCID: PMCPMC5445589.
18. Menche J, Sharma A, Kitsak M, Ghiassian S D, Vidal M, Loscalzo J, et al. Disease networks. Uncovering disease-disease relationships through the incomplete interactome. Science. 2015; 347(6224): 1257601. Epub 2015/02/24. doi: 10.1126/science.1257601. PubMed PMID: 25700523; PubMed Central PMCID: PMCPMC4435741.
19. Kotlyar M, Pastrello C, Malik Z, Jurisica I. IID 2018 update: context-specific physical protein-protein interactions in human, model organisms and domesticated species. Nucleic Acids Res. 2019; 47(D1):D581-D9. Epub 2018/11/09. doi: 10.1093/nar/gky1037. PubMed PMID: 30407591; PubMed Central PMCID: PMCPMC6323934.
20. Huttlin E L, Bruckner R J, Paulo J A, Cannon J R, Ting L, Battier K, et al. Architecture of the human interactome defines protein communities and disease networks. Nature. 2017; 545(7655):505-9. Epub 2017/05/18. doi: 10.1038/nature22366. PubMed PMID: 28514442; PubMed Central PMCID: PMCPMC5531611.
21. Choobdar S, Ahsen M E, Crawford J, Tomasoni M, Fang T, Lamparter D, et al. Assessment of network module identification across complex diseases. Nat Methods. 2019; 16(9):843-52. Epub 2019/09/01. doi: 10.1038/s41592-019-0509-5. PubMed PMID: 31471613; PubMed Central PMCID: PMCPMC6719725.
22. Arenas A, Fernandez A, Gómez S. Analysis of the structure of complex networks at different resolution levels. New Journal of Physics. 2008; 10(5):053039. doi: 10.1088/1367-2630/10/5/053039.
23. Jiang P, Singh M. SPICi: a fast clustering algorithm for large biological networks. Bioinformatics. 2010; 26(8): 1105-11. Epub 2010/02/27. doi: 10.1093/bioinformatics/btq078. PubMed PMID: 20185405; PubMed Central PMCID: PMCPMC2853685.
24. Dignat-George F, Boulanger C M. The many faces of endothelial microparticles. Arterioscler Thromb Vasc Biol. 2011; 31(1):27-33. Epub 2010/12/17. doi: 10.1161/ATVBAHA.110.218123. PubMed PMID: 21160065.
25. Aguirre-Plans J, Pinero J, Menche J, Sanz F, Furlong L I, Schmidt H, et al. Proximal Pathway Enrichment Analysis for Targeting Comorbid Diseases via Network Endopharmacology. Pharmaceuticals (Basel). 2018; 11(3). Epub 2018/06/23. doi: 10.3390/ph11030061. PubMed PMID: 29932108; PubMed Central PMCID: PMCPMC6160959.

26. Mazein A, Ostaszewski M, Kuperstein I, Watterson S, Le Novere N, Lefaudeux D, et al. Systems medicine disease maps: community-driven comprehensive representation of disease mechanisms. NPJ Syst Biol Appl. 2018; 4:21. Epub 2018/06/07. doi: 10.1038/s41540-018-0059-y. PubMed PMID: 29872544; PubMed Central PMCID: PMCPMC5984630.
27. Burns N S, Miller P W. Learning What We Didn't Know—The SPRINT Data Analysis Challenge. N Engl J Med. 2017; 376(23):2205-7. Epub 2017/04/27. doi: 10.1056/NEJMp1705323. PubMed PMID: 28445656.
28. Forstermann U, Munzel T. Endothelial nitric oxide synthase in vascular disease: from marvel to menace. Circulation. 2006; 113(13):1708-14. Epub 2006/04/06. doi: 10.1161/CIRCULATIONAHA.105.602532. PubMed PMID: 16585403.
29. Perticone F, Sciacqua A, Maio R, Perticone M, Maas R, Boger R H, et al. Asymmetric dimethylarginine, L-arginine, and endothelial dysfunction in essential primary hypertension. J Am Coll Cardiol. 2005; 46(3):518-23. Epub 2005/08/02. doi: 10.1016/j.jacc.2005.04.040. PubMed PMID: 16053968.
30. Sonmez A, Celebi G, Erdem G, Tapan S, Genc H, Tasci I, et al. Plasma apelin and ADMA Levels in patients with essential primary hypertension. Clin Exp Hypertens. 2010; 32(3):179-83. Epub 2010/05/28. doi: 10.3109/10641960903254505. PubMed PMID: 20504125.
31. Casas Al, Kleikers P W, Geuss E, Langhauser F, Adler T, Busch D H, et al. Calcium-dependent blood-brain barrier breakdown by NOX5 limits postreperfusion benefit in stroke. J Clin Invest. 2019; 130:1772-8. Epub 2019/03/19. doi: 10.1172/JC1124283. PubMed PMID: 30882367; PubMed Central PMCID: PMCPMC6436900.
32. Bubikat A, De Windt L J, Zetsche B, Fabritz L, Sickler H, Eckardt D, et al. Local atrial natriuretic peptide signaling prevents hypertensive cardiac hypertrophy in endothelial nitric-oxide synthase-deficient mice. J Biol Chem. 2005; 280(22):21594-9. Epub 2005/03/29. doi: 10.1074/jbc.M501103200. PubMed PMID: 15793309.
33. Godecke A, Decking U K, Ding Z, Hirchenhain J, Bidmon H J, Godecke S, et al. Coronary hemodynamics in endothelial NO synthase knockout mice. Circ Res. 1998; 82(2):186-94. Epub 1998/02/19. doi: 10.1161/01.res.82.2.186. PubMed PMID: 9468189.
34. Devereux R B, Pickering T G, Alderman M H, Chien S, Borer J S, Laragh J H. Left ventricular hypertrophy in hypertension. Prevalence and relationship to pathophysiologic variables. Hypertension. 1987; 9(2 Pt 2):1153-60. Epub 1987/02/01. doi: 10.1161/01.hyp.9.2_pt_2.ii53. PubMed PMID: 2879790.
35. Park J B, Schiffrin E L. Small artery remodeling is the most prevalent (earliest?) form of target organ damage in mild essential primary hypertension. J Hypertens. 2001; 19(5):921-30. Epub 2001/06/08. doi: 10.1097/00004872-200105000-00013. PubMed PMID: 11393676.
36. Cuspidi C, Sala C, Negri F, Mancia G, Morganti A, Italian Society of H. Prevalence of left-ventricular hypertrophy in hypertension: an updated review of echocardiographic studies. J Hum Hypertens. 2012; 26(6):343-9. Epub 2011/11/25. doi: 10.1038/jhh.2011.104. PubMed PMID: 22113443.
37. Bezie Y, Lamaziere J M, Laurent S, Challande P, Cunha R S, Bonnet J, et al. Fibronectin expression and aortic wall elastic modulus in spontaneously hypertensive rats. Arterioscler Thromb Vasc Biol. 1998; 18(7):1027-34. Epub 1998/07/22. doi: 10.1161/01.atv.18.7.1027. PubMed PMID: 9672062.
38. Hayoz D, Rutschmann B, Perret F, Niederberger M, Tardy Y, Mooser V, et al. Conduit artery compliance and distensibility are not necessarily reduced in hypertension. Hypertension. 1992; 20(1):1-6. Epub 1992/07/01. doi: 10.1161/01.hyp.20.1.1. PubMed PMID: 1618544.
39. Lacolley P, Ghodsi N, Glazer E, Challande P, Brissac A M, Safar M E, et al. Influence of graded changes in vasomotor tone on the carotid arterial mechanics in live spontaneously hypertensive rats. Br J Pharmacol. 1995; 115(7):1235-44. Epub 1995/08/01. doi: 10.1111/j.1476-5381.1995.tb15031.x. PubMed PMID: 7582551; PubMed Central PMCID: PMCPMC1908801.
40. Intengan H D, Schiffrin E L. Structure and mechanical properties of resistance arteries in hypertension: role of adhesion molecules and extracellular matrix determinants. Hypertension. 2000; 36(3):312-8. Epub 2000/09/16. doi: 10.1161/01.hyp.36.3.312. PubMed PMID: 10988257.
41. Bussy C, Boutouyrie P, Lacolley P, Challande P, Laurent S. Intrinsic stiffness of the carotid arterial wall material in essential hypertensives. Hypertension. 2000; 35(5):1049-54. Epub 2000/05/20. doi: 10.1161/01.hyp.35.5.1049. PubMed PMID: 10818063.
42. Laurent S, Girerd X, Mourad J J, Lacolley P, Beck L, Boutouyrie P, et al. Elastic modulus of the radial artery wall material is not increased in patients with essential primary hypertension. Arterioscler Thromb. 1994; 14(7): 1223-31. Epub 1994/07/01. doi: 10.1161/01.atv.14.7.1223. PubMed PMID: 8018679.
43. Laurent S, Hayoz D, Trazzi S, Boutouyrie P, Waeber B, Omboni S, et al. Isobaric compliance of the radial artery is increased in patients with essential primary hypertension. J Hypertens. 1993; 11(1):89-98. Epub 1993/01/01. doi: 10.1097/00004872-199301000-00013. PubMed PMID: 8382244.
44. Laurent S. Arterial wall hypertrophy and stiffness in essential hypertensive patients. Hypertension. 1995; 26(2):355-62. Epub 1995/08/01. doi: 10.1161/01.hyp.26.2.355. PubMed PMID: 7635546.
45. Furchgott R F, Zawadzki J V. The obligatory role of endothelial cells in the relaxation of arterial smooth muscle by acetylcholine. Nature. 1980; 288(5789):373-6. Epub 1980/11/27. doi: 10.1038/288373a0. PubMed PMID: 6253831.
46. Chennupati R, Lamers W H, Koehler S E, De Mey J G. Endotheliumdependent hyperpolarization-related relaxations diminish with age in murine saphenous arteries of both sexes. Br J Pharmacol. 2013; 169(7):1486-99. Epub 2013/03/16. doi: 10.1111/bph.12175. PubMed PMID: 23488619; PubMed Central PMCID: PMCPMC3724106.
47. Chennupati R, Meens M J, Marion V, Janssen B J, Lamers W H, De Mey J G, et al. Endothelial arginine resynthesis contributes to the maintenance of vasomotor function in male diabetic mice. PLoS One. 2014; 9(7): e102264. Epub 2014/07/18. doi: 10.1371/journal.pone.0102264. PubMed PMID: 25033204; PubMed Central PMCID: PMCPMC4102520.
48. Chennupati R, Meens M J, Janssen B J, van Dijk P, Hakvoort T B M, Lamers W H, et al. Deletion of endothelial arginase 1 does not improve vasomotor function in diabetic mice. Physiol Rep. 2018; 6(11):e13717. Epub 2018/06/12. doi: 10.14814/phy2.13717. PubMed PMID: 29890043; PubMed Central PMCID: PMCPMC5995309.
49. Ryan M J, Didion S P, Davis D R, Faraci F M, Sigmund C D. Endothelial dysfunction and blood pressure variability in selected inbred mouse strains. Arterioscler Thromb Vasc Biol. 2002; 22(1):42-8. Epub 2002/01/15. doi: 10.1161/hq0102.101098. PubMed PMID: 11788459.
50. Gebhart V, Reiss K, Kollau A, Mayer B, Gorren A C F. Site and mechanism of uncoupling of nitric-oxide synthase: Uncoupling by monomerization and other misconceptions. Nitric Oxide. 2019; 89:14-21. Epub 2019/04/26. doi: 10.1016/j.niox.2019.04.007. PubMed PMID: 31022534.
51. Mendes-Silverio C B, Leiria L O, Morganti R P, Anhe G F, Marcondes S, Monica F Z, et al. Activation of haem-oxidized soluble guanylyl cyclase with BAY 60-2770 in human platelets lead to overstimulation of the cyclic GMP signaling pathway. PLoS One. 2012; 7(11):e47223. Epub 2012/11/13. doi: 10.1371/journal.pone.0047223. PubMed PMID: 23144808; PubMed Central PMCID: PMCPMC3493568.
52. Stasch J P, Schmidt P M, Nedvetsky P I, Nedvetskaya T Y, H S A, Meurer S, et al. Targeting the heme-oxidized nitric oxide receptor for selective vasodilatation of diseased blood vessels. J Clin Invest. 2006; 116(9):2552-61. Epub 2006/09/07. doi: 10.1172/JCI28371. PubMed PMID: 16955146; PubMed Central PMCID: PMCPMC1555649.
53. Hrabie J A, Klose J R, Wink D A, Keefer L K. New nitric oxide-releasing zwitterions derived from polyamines. The Journal of Organic Chemistry. 1993; 58(6):1472-6. doi: 10.1021/jo00058a030.
54. Kietadisorn R, Juni R P, Moens A L. Tackling endothelial dysfunction by modulating NOS uncoupling: new insights into its pathogenesis and therapeutic possibilities. Am J Physiol Endocrinol Metab. 2012; 302(5):E481-95. Epub 2011/12/15. doi: 10.1152/ajpendo.00540.2011. PubMed PMID: 22167522.
55. Altenhofer S, Kleikers P W, Radermacher K A, Scheurer P, Rob Hermans J J, Schiffers P, et al. The NOX toolbox: validating the role of NADPH oxidases in physiology and disease. Cell Mol Life Sci. 2012; 69(14):2327-43. Epub 2012/06/01. doi: 10.1007/s00018-012-1010-9. PubMed PMID: 22648375; PubMed Central PMCID: PMCPMC3383958.
56. Altenhofer S, Radermacher K A, Kleikers P W, Wingler K, Schmidt H H. Evolution of NADPH Oxidase Inhibitors: Selectivity and Mechanisms for Target Engagement. Antioxid Redox Signal. 2015; 23(5):406-27. doi: 10.1089/ars.2013.5814. PubMed PMID: 24383718; PubMed Central PMCID: PMCPMC4543484.
57. Augsburger F, Filippova A, Rasti D, Seredenina T, Lam M, Maghzal G, et al. Pharmacological characterization of the seven human NOX isoforms and their inhibitors. Redox Biol. 2019; 26:101272. Epub 2019/07/23. doi: 10.1016/j.redox.2019.101272. PubMed PMID: 31330481; PubMed Central PMCID: PMCPMC6658998.
58. Dao V T, Elbatreek M H, Altenhofer S, Casas Al, Pachado M P, Neullens C T, et al. Isoform-selective NADPH oxidase inhibitor panel for pharmacological target validation. Free Radic Biol Med. 2019. Epub 2019/12/29. doi: 10.1016/j.freeradbiomed.2019.12.038. PubMed PMID: 31883469.
59. Frangos S, Buscombe J R. Why should we be concerned about a "g"? European Journal of Nuclear Medicine and Molecular Imaging. 2019; 46(2):519-. doi: 10.1007/s00259-018-4204-z.
60. Hornsten C, Weidung B, Littbrand H, Carlberg B, Nordstrom P, Lovheim H, et al. High blood pressure as a risk factor for incident stroke among very old people: a population-based cohort study. J Hypertens. 2016; 34(10):2059-65. Epub 2016/07/20. doi: 10.1097/HJH.0000000000001048. PubMed PMID: 27434102; PubMed Central PMCID: PMCPMC5398900.
61. Guzik T J, Chen W, Gongora M C, Guzik B, Lob H E, Mangalat D, et al. Calcium-dependent NOX5 nicotinamide adenine dinucleotide phosphate oxidase contributes to vascular oxidative stress in human coronary artery disease. J Am Coll Cardiol. 2008; 52(22):1803-9. Epub 2008/11/22. doi: 10.1016/j.jacc.2008.07.063. PubMed PMID: 19022160; PubMed Central PMCID: PMCPMC2593790.
62. Li H, Han X, Hu Z, Huang J, Chen J, Hixson J E, et al. Associations of NADPH oxidase-related genes with blood pressure changes and incident hypertension: The GenSalt Study. J Hum Hypertens. 2018; 32(4):287-93. Epub 2018/02/22. doi: 10.1038/s41371-018-0041-6. PubMed PMID: 29463833; PubMed Central PMCID: PMCPMC5889722.
63. Elbatreek M H, Pachado M P, Cuadrado A, Jandeleit-Dahm K, Schmidt H. Reactive Oxygen Comes of Age: Mechanism-Based Therapy of Diabetic End-Organ Damage. Trends Endocrinol Metab. 2019. Epub 2019/04/01. doi: 10.1016/j.tem.2019.02.006. PubMed PMID: 30928357.
64. Hermann M, Flammer A, Luscher T F. Nitric oxide in hypertension. J Clin Hypertens (Greenwich). 2006; 8(12 Suppl 4):17-29. Epub 2006/12/16. doi: 10.1111/j.1524-6175.2006.06032.x. PubMed PMID: 17170603.
65. Helbing T, Olivier C, Bode C, Moser M, Diehl P. Role of microparticles in endothelial dysfunction and arterial hypertension. World J Cardiol. 2014; 6(11):1135-9. Epub 2014/11/28. doi: 10.4330/wjc.v6.i11.1135. PubMed PMID: 25429325; PubMed Central PMCID: PMCPMC4244610.
66. Shantsila E. Endothelial microparticles: a universal marker of vascular health? J Hum Hypertens. 2009; 23(5):359-61. Epub 2008/11/21. doi: 10.1038/jhh.2008.138. PubMed PMID: 19020535.
67. Burger D, Turner M, Munkonda M N, Touyz R M. Endothelial Microparticle-Derived Reactive Oxygen Species: Role in Endothelial Signaling and Vascular Function. Oxid Med Cell Longev. 2016; 2016:5047954. Epub 2016/06/18. doi: 10.1155/2016/5047954. PubMed PMID: 27313830; PubMed Central PMCID: PMCPMC4893592.
68. Montezano A C, Burger D, Paravicini T M, Chignalia A Z, Yusuf H, Almasri M, et al. Nicotinamide adenine dinucleotide phosphate reduced oxidase 5 (Nox5) regulation by angiotensin II and endothelin-1 is mediated via calcium/calmodulin-dependent, rac-1-independent pathways in human endothelial cells. Circ Res. 2010; 106(8):1363-73. Epub 2010/03/27. doi: 10.1161/CIRCRESAHA.109.216036. PubMed PMID: 20339118; PubMed Central PMCID: PMCPMC3119893.
69. Yu P, Han W, Villar V A, Yang Y, Lu Q, Lee H, et al. Unique role of NADPH oxidase 5 in oxidative stress in human renal proximal tubule cells. Redox Biol. 2014; 2:570-9. Epub 2014/04/02. doi: 10.1016/j.redox.2014.01.020. PubMed PMID: 24688893; PubMed Central PMCID: PMCPMC3969603.
70. Hahn N E, Meischl C, Kawahara T, Musters R J, Verhoef V M, van der Velden J, et al. NOX5 expression is increased in intramyocardial blood vessels and cardiomyocytes after acute myocardial infarction in humans. Am J Pathol. 2012; 180(6):2222-9. Epub 2012/04/17. doi: 10.1016/j.ajpath.2012.02.018. PubMed PMID: 22503554.
71. Holterman C E, Thibodeau J F, Kennedy C R. NADPH oxidase 5 and renal disease. Curr Opin Nephrol Hyper- 72. Bouabout G, Ayme-Dietrich E, Jacob H, Champy M F, Birling M C, Pavlovic G, et al. Nox4 genetic inhibition in experimental hypertension and metabolic syndrome. Arch Cardiovasc Dis. 2018; 111(1):41-52. Epub 2017/11/09. doi: 10.1016/j.acvd.2017.03.011. PubMed PMID: 29113787.
73. Schroder K, Zhang M, Benkhoff S, Mieth A, Pliquett R, Kosowski J, et al. Nox4 is a protective reactive oxygen species generating vascular NADPH oxidase. Circ Res. 2012; 110(9):1217-25. Epub 2012/03/30. doi: 10.1161/CIRCRESAHA.112.267054. PubMed PMID: 22456182.
74. Veith C, Kraut S, Wilhelm J, Sommer N, Quanz K, Seeger W, et al. NADPH oxidase 4 is not involved in hypoxia-induced pulmonary hypertension. Pulm Circ. 2016; 6(3):397-400. Epub 2016/09/30. doi: 10.1086/687756. PubMed PMID: 27683617; PubMed Central PMCID: PMCPMC5019094.
75. Brandes R P, Takac I, Schroder K. No superoxide—no stress?: Nox4, the good NADPH oxidase! Arterioscler Thromb Vasc Biol. 2011; 31(6):1255-7. Epub 2011/05/20. doi: 10.1161/ATVBAHA.111.226894. PubMed PMID: 21593458.
76. Miura H, Bosnjak J J, Ning G, Saito T, Miura M, Gutterman D D. Role for hydrogen peroxide in flow-induced dilation of human coronary arterioles. Circ Res. 2003; 92(2):e31-40. Epub 2003/02/08. doi: 10.1161/01.res.0000054200.44505.ab. PubMed PMID: 12574154.
77. Leurgans T M, Bloksgaard M, Brewer J R, Bagatolli L A, Fredgart M H, Rosenstand K, et al. Endothelin-1 shifts the mediator of bradykinin-induced relaxation from NO to $H_2O_2$ in resistance arteries from patients with cardiovascular disease. Br J Pharmacol. 2016; 173(10):1653-64. Epub 2016/02/26. doi: 10.1111/bph.13467. PubMed PMID: 26914408; PubMed Central PMCID: PMCPMC4842913.
78. Shimokawa H. Hydrogen peroxide as an endothelium-derived hyperpolarizing factor. Pflugers Arch. 2010; 459 (6):915-22. Epub 2010/02/09. doi: 10.1007/s00424-010-0790-8. PubMed PMID: 20140449.
79. Landmesser U, Dikalov S, Price S R, McCann L, Fukai T, Holland S M, et al. Oxidation of tetrahydrobiopterin leads to uncoupling of endothelial cell nitric oxide synthase in hypertension. J Clin Invest. 2003; 111(8):1201-9. Epub 2003/04/17. doi: 10.1172/JCI14172. PubMed PMID: 12697739; PubMed Central PMCID: PMCPMC152929.
80. Dumitrescu C, Biondi R, Xia Y, Cardounel A J, Druhan L J, Ambrosio G, et al. Myocardial ischemia results in tetrahydrobiopterin ($BH_4$) oxidation with impaired endothelial function ameliorated by BI-14. Proc Natl Acad Sci USA. 2007; 104(38):15081-6. Epub 2007/09/13. doi: 10.1073/pnas.0702986104. PubMed PMID: 17848522; PubMed Central PMCID: PMCPMC1986616.
81. Mitchell B M, Dorrance A M, Webb R C. GTP cyclohydrolase 1 inhibition attenuates vasodilation and increases blood pressure in rats. Am J Physiol Heart Circ Physiol. 2003; 285(5):H2165-70. Epub 2003/07/12. doi: 10.1152/ajpheart.00253.2003. PubMed PMID: 12855421.
82. Pi X, Xie L, Portbury A L, Kumar S, Lockyer P, Li X, et al. NADPH oxidase-generated reactive oxygen species are required for stromal cell-derived factor-1alphastimulated angiogenesis. Arterioscler Thromb Vasc Biol. 2014; 34(9):2023-32. Epub 2014/07/06. doi: 10.1161/ATVBAHA.114.303733. PubMed PMID: 24990230; PubMed Central PMCID: PMCPMC4149803.
83. Barton M, Cosentino F, Brandes R P, Moreau P, Shaw S, Luscher T F. Anatomic heterogeneity of vascular aging: role of nitric oxide and endothelin. Hypertension. 1997; 30(4):817-24. Epub 1997/10/23. doi: 10.1161/01.hyp.30.4.817. PubMed PMID: 9336378.
84. Matz R L, de Sotomayor M A, Schott C, Stoclet J C, Andriantsitohaina R. Vascular bed heterogeneity in age-related endothelial dysfunction with respect to NO and eicosanoids. Br J Pharmacol. 2000; 131(2):303-11. Epub 2000/09/19. doi: 10.1038/sj.bjp.0703568. PubMed PMID: 10991924; PubMed Central PMCID: PMCPMC1572322.
85. Wang S, Xu J, Song P, Wu Y, Zhang J, Chul Choi H, et al. Acute inhibition of guanosine triphosphate cyclohydrolase 1 uncouples endothelial nitric oxide synthase and elevates blood pressure. Hypertension. 2008; 52(3):484-90. Epub 2008/07/23. doi: 10.1161/HYPERTENSIONAHA.108.112094. PubMed PMID: 18645049; PubMed Central PMCID: PMCPMC3523107.
86. Podjarny E, Hasdan G, Bernheim J, Rashid G, Green J, Korzets Z, et al. Effect of chronic tetrahydrobiopterin supplementation on blood pressure and proteinuria in 5/6 nephrectomized rats. Nephrol Dial Transplant. 2004; 19(9):2223-7. Epub 2004/07/15. doi: 10.1093/ndt/gfh383. PubMed PMID: 15252157.
87. Sundberg J P, Berndt A, Sundberg B A, Silva K A, Kennedy V, Bronson R, et al. The mouse as a model for understanding chronic diseases of aging: the histopathologic basis of aging in inbred mice. Pathobiol Aging Age Relat Dis. 2011; 1. Epub 2011/01/01. doi: 10.3402/pba.v1i0.7179. PubMed PMID: 22953031; PubMed Central PMCID: PMCPMC3417678.
88. Porkert M, Sher S, Reddy U, Cheema F, Niessner C, Kolm P, et al. Tetrahydrobiopterin: a novel antihypertensive therapy. J Hum Hypertens. 2008; 22(6):401-7. Epub 2008/03/07. doi: 10.1038/sj.jhh.1002329. PubMed PMID: 18322548.
89. McRae M P. High-dose folic acid supplementation effects on endothelial function and blood pressure in hypertensive patients: a meta-analysis of randomized controlled clinical trials. J Chiropr Med. 2009; 8(1):15-24. Epub 2009/08/04. doi: 10.1016/j.jcm.2008.09.001. PubMed PMID: 19646382; PubMed Central PMCID: PMCPMC2697578.
90. Kong X, Huang X, Zhao M, Xu B, Xu R, Song Y, et al. Platelet Count Affects Efficacy of Folic Acid in Preventing First Stroke. J Am Coll Cardiol. 2018; 71(19):2136-46. Epub 2018/05/12. doi: 10.1016/j.jacc.2018.02.072. PubMed PMID: 29747834.
91. Huo Y, Li J, Qin X, Huang Y, Wang X, Gottesman R F, et al. Efficacy of folic acid therapy in primary prevention of stroke among adults with hypertension in China: the CSPPT randomized clinical trial. JAMA. 2015; 313(13):1325-35. Epub 2015/03/17. doi: 10.1001/jama.2015.2274. PubMed PMID: 25771069.
92. Wang W W, Wang X S, Zhang Z R, He J C, Xie C L. A Meta-Analysis of Folic Acid in Combination with Anti-Hypertension Drugs in Patients with Hypertension and Hyperhomocysteinemia. Front Pharmacol. 2017; 8:585. Epub 2017/09/16. doi: 10.3389/fphar.2017.00585. PubMed PMID: 28912716; PubMed Central PMCID: PMCPMC5584015.
93. Hsu C Y, Huang P H, Chiang C H, Leu H B, Huang C C, Chen J W, et al. Increased circulating endothelial apoptotic microparticle to endothelial progenitor cell ratio is associated with subsequent decline in glomerular filtration rate in hypertensive patients. PLoS One. 2013;

8(7):e68644. Epub 2013/07/23. doi: 10.1371/journal.pone.0068644. PubMed PMID: 23874701; PubMed Central PMCID: PMCPMC3709900.
94. Huang P H, Huang S S, Chen Y H, Lin C P, Chiang K H, Chen J S, et al. Increased circulating CD31+/annexin V+ apoptotic microparticles and decreased circulating endothelial progenitor cell levels in hypertensive patients with microalbuminuria. J Hypertens. 2010; 28(8):1655-65. Epub 2010/06/04. doi: 10.1097/HJH.0b013e32833a4d0a. PubMed PMID: 20520578.
95. Shang F, Wang S C, Hsu C Y, Miao Y, Martin M, Yin Y, et al. MicroRNA-92a Mediates Endothelial Dysfunction in CKD. J Am Soc Nephrol. 2017; 28(11):3251-61. Epub 2017/07/12. doi: 10.1681/ASN.2016111215. PubMed PMID: 28696247; PubMed Central PMCID: PMCPMC5661278.
96. Chen Z, Wen L, Martin M, Hsu C Y, Fang L, Lin F M, et al. Oxidative stress activates endothelial innate immunity via sterol regulatory element binding protein 2 (SREBP2) transactivation of microRNA-92a. Circulation. 2015; 131(9):805-14. Epub 2015/01/01. doi: 10.1161/CIRCULATIONAHA.114.013675. PubMed PMID: 25550450; PubMed Central PMCID: PMCPMC4351177.
97. Wang Y, Thorin E, Luo H, Tremblay J, Lavoie J L, Wu Z, et al. EPHB4 Protein Expression in Vascular Smooth Muscle Cells Regulates Their Contractility, and EPHB4 Deletion Leads to Hypotension in Mice. J Biol Chem. 2015; 290(22):14235-44. Epub 2015/04/24. doi: 10.1074/jbc.M114.621615. PubMed PMID: 25903126; PubMed Central PMCID: PMCPMC4447992.
98. Xu P, Costa-Goncalves A C, Todiras M, Rabelo L A, Sampaio W O, Moura M M, et al. Endothelial dysfunction and elevated blood pressure in MAS gene-deleted mice. Hypertension. 2008; 51(2):574-80. Epub 2008/01/09. doi: 10.1161/HYPERTENSIONAHA. 107.102764. PubMed PMID: 18180400.
99. Shirey-Rice J K, Klar R, Fentress H M, Redmon S N, Sabb T R, Krueger J J, et al. Norepinephrine transporter variant A457P knock-in mice display key features of human postural orthostatic tachycardia syndrome. Dis Model Mech. 2013; 6(4):1001-11. Epub 2013/04/13. doi: 10.1242/dmm.012203. PubMed PMID: 23580201; PubMed Central PMCID: PMCPMC3701219.
100. Lazor R, Feihl F, Waeber B, Kucera P, Perret C. Endothelin-1 does not mediate the endothelium-dependent hypoxic contractions of small pulmonary arteries in rats. Chest. 1996; 110(1):189-97. Epub 1996/07/01. doi: 10.1378/chest.110.1.189. PubMed PMID: 8681627.
101. Bloksgaard M, Leurgans T M, Spronck B, Heusinkveld M H G, Thorsted B, Rosenstand K, et al. Imaging and modeling of acute pressure-induced changes of collagen and elastin microarchitectures in pig and human resistance arteries. Am J Physiol Heart Circ Physiol. 2017; 313(1):H164-H78. Epub 2017/04/23. doi: 10.1152/ajpheart.00110.2017. PubMed PMID: 28432057.
102. Pourageaud F, De Mey J G. Structural properties of rat mesenteric small arteries after 4-wk exposure to elevated or reduced blood flow. Am J Physiol. 1997; 273(4):H1699-706. Epub 1997/11/15. doi: 10.1152/ajpheart.1997.273.4.H1699. PubMed PMID: 9362233.
103. Scott D W. Sturges' rule. Wire computational statistics. 2009; 1(3):303-6. doi: https://doi.org/10.1002/wics.35.
104. Robert M. Carey, M D, FAHA, David A. Calhoun, M D, FAHA, George L. Bakris, et al. Resistant Hypertension: Detection, Evaluation, and Management: A Scientific Statement From the American Heart Association. Hypertension. 2018 November; 72(5): e53-e90. doi: 10.1161/HYP.0000000000000084. PMID: 30354828.

The invention claimed is:

1. A method for treating essential hypertension in a subject, comprising administering one or more of the compounds sepiapterin, folic acid, L citrulline, L arginine and tetrahydrobiopterin to said subject, wherein said subject is a human patient suffering from essential arterial hypertension and having an NOX5 endothelial microparticles plasma concentration of at least 160 pg NOX5 per ml plasma as determined by a method comprising the steps of:
(a) obtaining a fluid sample from the human patient who suffers from essential arterial hypertension, selected from the group comprising plasma, blood and serum, wherein the fluid sample comprises circulating endothelial microparticles;
(b) isolating the endothelial microparticles from the fluid sample provided in step (a), wherein the circulating endothelial microparticles comprise CD144+ endothelial microparticles; and
(c) measuring NOX5 in the endothelial microparticles of step (b) by performing an ELISA protein detection assay and determining the concentration of NOX5 in the fluid sample comprising the isolated endothelial microparticles, in pg NOX5 per fluid sample,
wherein a concentration of at least 160 pg NOX5 per ml of the plasma fluid sample as measured in (c) is indicative of essential arterial hypertension.

2. The method for treatment according to claim 1, wherein the human patient suffers from hypertension as defined as a systolic blood pressure of at least 140 mmHg, a diastolic blood pressure of at least 90 mmHg.

3. The method for treating according to claim 1, wherein the human patient has moderately increased albuminuria defined as albumin excretion rate of 20-200 mg per minute.

4. The method for treating according to claim 1, wherein the human patient is at least 53 years of age or at least 57 years of age.

5. The method for treating according to claim 1, wherein the human patient has a plasma concentration of asymmetric dimethylarginine that is higher compared to the average plasma concentration of asymmetric dimethylarginine of a group of healthy human subjects.

6. The method for treating according to claim 1, wherein the human patient has a plasma concentration of asymmetric dimethylarginine of at least 0.53 micromol per liter.

7. The method for treating according to claim 1, wherein the human patient does not have a history or clinical evidence of any of: angina, myocardial infarction, congestive heart failure, peripheral vascular disease, inflammatory disease and any disease predisposing to vasculitis, and wherein the human patient does not have stage 4 or stage 5 chronic kidney disease.

* * * * *